US010653670B2

(12) United States Patent
Duncan et al.

(10) Patent No.: US 10,653,670 B2
(45) Date of Patent: *May 19, 2020

(54) USE OF INDOLE COMPOUNDS FOR FAT REDUCTION AND SKIN AND SOFT TISSUE TIGHTENING

(71) Applicant: Alevere Medical Corporation, Fort Collins, CO (US)

(72) Inventors: Diane Duncan, Fort Collins, CO (US); Tim Kamerzell, Overland Park, KS (US); Mark Palmer, Dewsbury (GB)

(73) Assignee: Alevere Medical Corporation, Fort Collins, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/283,985

(22) Filed: Feb. 25, 2019

(65) Prior Publication Data

US 2019/0290613 A1 Sep. 26, 2019

Related U.S. Application Data

(63) Continuation of application No. 15/807,081, filed on Nov. 8, 2017, now Pat. No. 10,258,605, which is a
(Continued)

(51) Int. Cl.
*A61K 31/404* (2006.01)
*A61K 31/4045* (2006.01)
(Continued)

(52) U.S. Cl.
CPC .......... *A61K 31/404* (2013.01); *A61K 9/0019* (2013.01); *A61K 31/405* (2013.01);
(Continued)

(58) Field of Classification Search
CPC .............. A61K 2300/00; A61K 31/404; A61K 31/405; A61K 31/4184; A61K 31/437;
(Continued)

(56) References Cited

U.S. PATENT DOCUMENTS

| 4,588,724 A | 5/1986 | Greenway, III et al. |
| 10,258,605 B2 | 4/2019 | Duncan et al. |

(Continued)

FOREIGN PATENT DOCUMENTS

| WO | WO-2004/062389 A1 | 7/2004 |
| WO | WO-2005/009370 A2 | 2/2005 |

(Continued)

OTHER PUBLICATIONS

Partial Supplementary Search Report from European Patent Office dated Sep. 21, 2016 for European Patent Application No. 13878099.4 (International Patent Application PCT/US2013/048368). (7 pages).
Chang, H.-P. et al. "Suppression of inflammation-associated factors by indole-3-carbinol in mice fed high-fat diets and in isolated, co-cultured macrophages and adipocytes," *Intl. J. Obesity* (2011) vol. 35, No. 12, pp. 1530-1538.
(Continued)

*Primary Examiner* — Savitha M Rao
(74) *Attorney, Agent, or Firm* — Dechert LLP

(57) ABSTRACT

The present invention relates to indole compounds and compositions and uses thereof, including uses of the indole compounds and compositions for the reduction or removal of localized fat deposits and/or tightening of skin and soft tissue laxity in subjects. The indole compounds can be employed, for example, in the cosmetic sector or for producing pharmaceutical products.

20 Claims, 59 Drawing Sheets

Related U.S. Application Data continuation of application No. 14/772,602, filed as application No. PCT/US2013/048368 on Jun. 27, 2013, now abandoned.

(60) Provisional application No. 61/780,792, filed on Mar. 13, 2013.

(51) Int. Cl.
*A61K 31/405* (2006.01)
*A61K 31/4184* (2006.01)
*A61K 31/437* (2006.01)
*A61K 9/00* (2006.01)
*A61K 45/06* (2006.01)

(52) U.S. Cl.
CPC ...... *A61K 31/4045* (2013.01); *A61K 31/4184* (2013.01); *A61K 31/437* (2013.01); *A61K 45/06* (2013.01)

(58) Field of Classification Search
CPC ... A61K 31/4045; A61K 45/06; A61K 9/0019
See application file for complete search history.

(56) References Cited

U.S. PATENT DOCUMENTS

2005/0288354 A1  12/2005  Arnold et al.
2010/0234295 A1   9/2010  Chen

FOREIGN PATENT DOCUMENTS

| WO | WO-2005/030756 A1 | 4/2005 |
| WO | WO-2011/163389 A2 | 12/2011 |
| WO | WO-2012/108622 A1 | 8/2012 |
| WO | WO-2014/143125 A1 | 9/2014 |

OTHER PUBLICATIONS

Caruso, M. K. et al. "An evaluation of mesotherapy solutions for inducing lipolysis and treating cellulite," *J. Plastic, Reconstructive and Aesthetic Surgery* (2008) vol. 61, No. 11, pp. 1321-1324.

International Search Report and Written Opinion for International Patent Application PCT/US2013/048368 dated Aug. 13, 2013. (9 pages).

Chang, H.-P. et al. "Antiobesity activities of indole-3-carbinol in high-fat-diet-induced obese mice," *Nutrition* (2011) vol. 27, No. 4, pp. 463-470.

USE OF INDOLE COMPOUNDS FOR FAT REDUCTION AND SKIN AND SOFT TISSUE TIGHTENING

CROSS-REFERENCE TO RELATED APPLICATIONS

This application is a continuation of U.S. patent application Ser. No. 15/807,081, filed Nov. 8, 2017, which is a continuation of U.S. patent application Ser. No. 14/772,602, filed Sep. 3, 2015, which is the national stage of International (PCT) Patent Application Serial No. PCT/US13/048368, filed Jun. 27, 2013 which claims priority to U.S. Provisional Patent Application No. 61/780,792, filed Mar. 13, 2013, the contents of each application are hereby incorporated by reference in their entirety.

TECHNICAL FIELD

The present invention relates to indole compounds, compositions, and uses thereof, including uses of the indole compounds and compositions for the reduction or removal of localized fat deposits and/or tightening of skin and soft tissue laxity in subjects. The indole compounds can be employed, for example, in the cosmetic sector or for producing pharmaceutical products.

BACKGROUND

Liposuction is one of the most popular cosmetic surgery procedures currently available. It involves the surgical removal of fat deposits using suction, optionally assisted by solutions to assist in fat removal. Liposuction, also known as lipoplasty or suction lipectomy, reduces fat through an incision in the skin through which a cannula is inserted. Tumescent fluid is injected into the treatment region, then the cannula is inserted. The cannula is connected to a suction source and the unwanted fat is aspirated through the cannula and discarded. Liposuction is performed under general or local anesthesia, depending on the amount and location of the fat to be reduced.

The use of liposuction and/or other surgical methods of fat removal are associated with significant adverse events including temporary bruising, swelling, numbness or hypersensitivity, soreness and burning sensation, risk of infection, and pigmentation changes. Other more serious complications include the formation of fat clots or blood clots, which can migrate to the lungs and cause death; excessive fluid loss, which can lead to shock; fluid accumulation that must be drained; fluid overload leading to congestive heart failure; friction burns or other damage to the skin or nerves; and perforation injury to the vital organs. Additionally, liposuction requires a recovery time of up to 1-2 weeks. Moreover, because surgical procedures such as liposuction require local and occasionally general anesthesia, significant anesthesia-related risks are associated with surgical fat removal.

In 1959, phosphatidylcholine (hereinafter "PC") was isolated and used intravenously in Odessa, Russia, for the treatment of fat embolism. PC has also been used in treating xanthelasmas in Europe and in South America. An injectable form of PC (LIPOSTABIL®, Sanofi-Aventis, Brigewater, N.J.) has been indicated for treatment of fat embolisms, coronary artery plaque, and fat tissue.

PC is often an ingredient in injectable fat reducing formulas. When isolated, it is produced as a powder. When reconstituted, it is quite viscous and must be mixed with a detergent, such as sodium deoxycholate (hereinafter "DC"), to solubilize it sufficiently to create an injectable form. DC is a bile salt that can function to make the PC soluble in water or other biocompatible solvents; otherwise, the PC can precipitate out of solution. DC has been described as having a "detergent" effect on fat dissolution in a porcine in vitro study and has nonspecific effects on both adipose and muscle cells. Other pharmaceuticals, such as FUNGIZONE® (Bristol Myers Squibb, New York, N.Y.) (an injectable form of amphotericin B), are commonly combined with bile salts to enhance their solubility and make them compatible with intravenous delivery.

While formulations of DC without PC ("DC formulations") and formulations of PC combined with DC ("PC/DC formulations") have been shown to achieve a level of fat reduction, substantial unresolved problems remain with the use of such formulations and methods of use, as reported in Duncan et al. (Duncan D. Injection lipolysis for body contouring, p 59-70. *Body Contouring*, ed. Schiffman and DiGiuseppe, Springer 2010, Berlin.).

While meeting with some success, prior techniques and compositions have met with certain limitations, such as skin loss, drainage of liquefied necrotic fat, excessive fibrosis, injections into muscle causing weakness, nodules, or adhesions with limitation of range of motion, numbness, paresthesias, and marginal mandibular nerve palsy. Therefore it would be desirable to have a method of reducing localized fat deposits that does not require surgery or prolonged recovery time and has fewer adverse side effects than currently available methods.

SUMMARY

The present invention relates to indole compounds, compositions, and uses thereof, including uses of the indole compounds and compositions for the reduction or removal of localized fat deposits and/or tightening of skin and soft tissue laxity in subjects.

The present disclosure provides, in some embodiments, a method for non-surgical reduction or removal of one or more localized fat deposits in a subject having localized fat accumulation comprising administering to a target site in the fat deposit a composition comprising a compound of Formula (I):

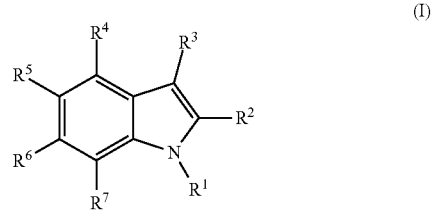

wherein $R^1$ is hydrogen, $C_{1-6}$ alkyl, hydroxyl, or —$(CH_2)_x$—$CONH_2$;

$R^2$, $R^3$, $R^4$, $R^5$, $R^6$, and $R^7$ are independently selected from hydrogen, $C_{1-6}$alkyl, $C_{1-6}$alkoxy, amino, substituted amino, halogen, heteroaryl, substituted heteroaryl, —$(CH_2)_x$—C(O)—$OC_{1-6}$ alkyl, —$(CH_2)_x$—OH, —$(CH_2)_x$—CN, —$OCH_2C_6H_5$, —$OCOCH_3$, —$(CH_2)_x$—$CONH_2$, —CHO, —$(CH_2)_x$—COOH, —$(CH_2)_x$—$COOC_{1-6}$ alkyl, —$(CH_2)_y$—CO—COOH, and —$(CH_2)_y$—C(H)(OH)—COOH; or any two adjacent $R^4$, $R^5$, $R^6$, and $R^7$, together with the atoms they attach to, form a five to seven-membered carbocyclic ring; or $R^2$ and $R^3$, together with the atoms they attach to, form an unsubstituted or substituted five to seven-membered heterocyclyl ring;

x is a number from zero to six; and y is a number from zero to six;

or a pharmaceutically acceptable salt thereof.

The present disclosure provides, in some embodiments, a method for reducing a subcutaneous fat deposit in a subject having subcutaneous fat deposit comprising administering to a target site in the subcutaneous fat deposit a composition comprising a compound of Formula (I):

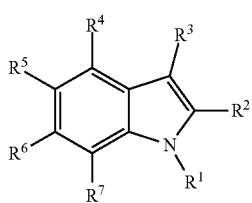

(I)

wherein $R^1$ is hydrogen, $C_{1-6}$ alkyl, hydroxyl, or —$(CH_2)_x$—$CONH_2$;

$R^2$, $R^3$, $R^4$, $R^5$, $R^6$, and $R^7$ are independently selected from hydrogen, $C_{1-6}$alkyl, $C_{1-6}$alkoxy, amino, substituted amino, halogen, heteroaryl, substituted heteroaryl, —$(CH_2)_x$—$C(O)$—$OC_{1-6}$ alkyl, —$(CH_2)_x$—OH, —$(CH_2)_x$—CN, —$OCH_2C_6H_5$, —$OCOCH_3$, —$(CH_2)_x$—$CONH_2$, —CHO, —$(CH_2)_x$—COOH, —$(CH_2)_x$—$COOC_{1-6}$ alkyl, —$(CH_2)_y$—CO—COOH, and —$(CH_2)_y$—C(H)(OH)—COOH; or any two adjacent $R^4$, $R^5$, $R^6$, and $R^7$, together with the atoms they attach to, form a five to seven-membered carbocyclic ring; or $R^2$ and $R^3$, together with the atoms they attach to, form an unsubstituted or substituted five to seven-membered heterocyclyl ring;

x is a number from zero to six; and y is a number from zero to six;

or a pharmaceutically acceptable salt thereof.

The present disclosure provides, in some embodiments, a method for treating an adipose tissue disorder or an adipose tissue tumor in a subject comprising locally administering to the subject a composition comprising a compound of Formula (I):

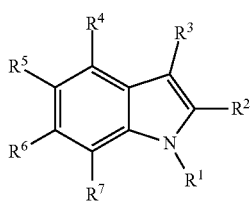

(I)

wherein $R^1$ is hydrogen, $C_{1-6}$ alkyl, hydroxyl, or —$(CH_2)_x$—$CONH_2$;

$R^2$, $R^3$, $R^4$, $R^5$, $R^6$, and $R^7$ are independently selected from hydrogen, $C_{1-6}$alkyl, $C_{1-6}$alkoxy, amino, substituted amino, halogen, heteroaryl, substituted heteroaryl, —$(CH_2)_x$—$C(O)$—$OC_{1-6}$ alkyl, —$(CH_2)_x$—OH, —$(CH_2)_x$—CN, —$OCH_2C_6H_5$, —$OCOCH_3$, —$(CH_2)_x$—$CONH_2$, —CHO, —$(CH_2)_x$—COOH, —$(CH_2)_x$—$COOC_{1-6}$ alkyl, —$(CH_2)_y$—CO—COOH, and —$(CH_2)_y$—C(H)(OH)—COOH; or any two adjacent $R^4$, $R^5$, $R^6$, and $R^7$, together with the atoms they attach to, form a five to seven-membered carbocyclic ring; or $R^2$ and $R^3$, together with the atoms they attach to, form an unsubstituted or substituted five to seven-membered heterocyclyl ring;

x is a number from zero to six; and y is a number from zero to six;

or a pharmaceutically acceptable salt thereof.

The present disclosure provides, in some embodiments, a method for decreasing submental fat deposit under a skin area in a subject comprising administering to a target site in the fat deposit a composition comprising a compound of Formula (I):

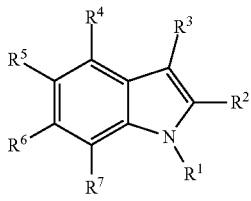

(I)

wherein $R^1$ is hydrogen, $C_{1-6}$ alkyl, hydroxyl, or —$(CH_2)_x$—$CONH_2$;

$R^2$, $R^3$, $R^4$, $R^5$, $R^6$, and $R^7$ are independently selected from hydrogen, $C_{1-6}$alkyl, $C_{1-6}$alkoxy, amino, substituted amino, halogen, heteroaryl, substituted heteroaryl, —$(CH_2)_x$—$C(O)$—$OC_{1-6}$ alkyl, —$(CH_2)_x$—OH, —$(CH_2)_x$—CN, —$OCH_2C_6H_5$, —$OCOCH_3$, —$(CH_2)_x$—$CONH_2$, —CHO, —$(CH_2)_x$—COOH, —$(CH_2)_x$—$COOC_{1-6}$ alkyl, —$(CH_2)_y$—CO—COOH, and —$(CH_2)_y$—C(H)(OH)—COOH; or any two adjacent $R^4$, $R^5$, $R^6$, and $R^7$, together with the atoms they attach to, form a five to seven-membered carbocyclic ring; or $R^2$ and $R^3$, together with the atoms they attach to, form an unsubstituted or substituted five to seven-membered heterocyclyl ring;

x is a number from zero to six; and y is a number from zero to six;

or a pharmaceutically acceptable salt thereof.

The present disclosure provides, in some embodiments, a method for preventing or reducing a skin condition (including method of tightening skin and/or lax subcutaneous tissue) associated with aging in a subject comprising locally administering to the subject a composition comprising a compound of Formula (I):

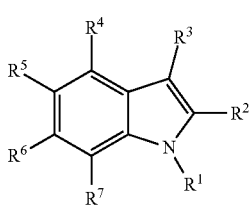

(I)

wherein

R$^1$ is hydrogen, C$_{1-6}$ alkyl, hydroxyl, or —(CH$_2$)$_x$—CONH$_2$;

R$^2$, R$^3$, R$^4$, R$^5$, R$^6$, and R$^7$ are independently selected from hydrogen, C$_{1-6}$alkyl, C$_{1-6}$alkoxy, amino, substituted amino, halogen, heteroaryl, substituted heteroaryl, —(CH$_2$)$_x$—C(O)—OC$_{1-6}$ alkyl, —(CH$_2$)$_x$—OH, —(CH$_2$)$_x$—CN, —OCH$_2$C$_6$H$_5$, —OCOCH$_3$, —(CH$_2$)$_x$—CONH$_2$, —CHO, —(CH$_2$)$_x$—COOH, —(CH$_2$)$_x$—COOC$_{1-6}$ alkyl, —(CH$_2$)$_y$—CO—COOH, and —(CH$_2$)$_y$—C(H)(OH)—COOH; or any two adjacent R$^4$, R$^5$, R$^6$, and R$^7$, together with the atoms they attach to, form a five to seven-membered carbocyclic ring; or R$^2$ and R$^3$, together with the atoms they attach to, form an unsubstituted or substituted five to seven-membered heterocyclyl ring;

x is a number from zero to six; and y is a number from zero to six;

or a pharmaceutically acceptable salt thereof.

The present disclosure provides, in some embodiments, a method for treating sleep apnea in a subject comprising locally administering a composition comprising a compound of Formula (I), wherein the sleep apnea is caused by a fat deposit around a trachea in the subject and the administration of the composition is to the fat deposit around the trachea, and wherein Formula (I) is:

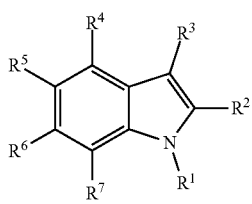

(I)

wherein

R$^1$ is hydrogen, C$_{1-6}$ alkyl, hydroxyl, or —(CH$_2$)$_x$—CONH$_2$;

R$^2$, R$^3$, R$^4$, R$^5$, R$^6$, and R$^7$ are independently selected from hydrogen, C$_{1-6}$alkyl, C$_{1-6}$alkoxy, amino, substituted amino, halogen, heteroaryl, substituted heteroaryl, —(CH$_2$)$_x$—C(O)—OC$_{1-6}$ alkyl, —(CH$_2$)$_x$—OH, —(CH$_2$)$_x$—CN, —OCH$_2$C$_6$H$_5$, —OCOCH$_3$, —(CH$_2$)$_x$—CONH$_2$, —CHO, —(CH$_2$)$_x$—COOH, —(CH$_2$)$_x$—COOC$_{1-6}$ alkyl, —(CH$_2$)$_y$—CO—COOH, and —(CH$_2$)$_y$—C(H)(OH)—COOH; or any two adjacent R$^4$, R$^5$, R$^6$, and R$^7$, together with the atoms they attach to, form a five to seven-membered carbocyclic ring; or R$^2$ and R$^3$, together with the atoms they attach to, form an unsubstituted or substituted five to seven-membered heterocyclyl ring;

x is a number from zero to six; and y is a number from zero to six;

or a pharmaceutically acceptable salt thereof.

In some embodiments of any of the above methods, the compound is of Formula (II):

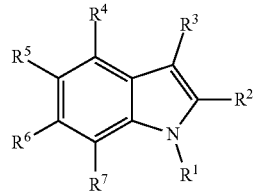

(II)

wherein

R$^1$ is hydrogen, C$_{1-6}$ alkyl, or hydroxy;

R$^2$, R$^3$, R$^4$, R$^5$, R$^6$, and R$^7$ are independently selected from hydrogen, C$_{1-6}$alkyl, C$_{1-6}$alkoxy, amino, substituted amino, halogen, —(CH$_2$)$_x$—C(O)—OC$_{1-6}$ alkyl, —(CH$_2$)$_x$—OH, —(CH$_2$)$_x$—CN, —OCH$_2$C$_6$H$_5$, —CHO, —(CH$_2$)$_x$—COOH, —(CH$_2$)$_x$—COOC$_{1-6}$ alkyl, —(CH$_2$)$_y$—CO—COOH, and —(CH$_2$)$_y$—C(H)(OH)—COOH; or any two adjacent R$^4$, R$^5$, R$^6$, and R$^7$, together with the atoms they attach to, form a five to seven-membered carbocyclic ring;

x is a number from zero to six; and y is a number from zero to six;

or a pharmaceutically acceptable salt thereof.

In some embodiments of any of the above methods, the compound is of Formula (III):

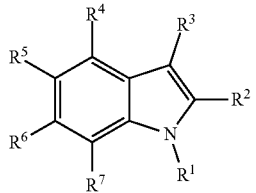

(III)

wherein

R$^1$ is hydrogen, C$_{1-6}$ alkyl, or hydroxy;

R$^2$, R$^3$, R$^4$, R$^5$, R$^6$, and R$^7$ are independently selected from hydrogen, C$_{1-6}$alkyl, C$_{1-6}$alkoxy, amino, substituted amino, halogen, —(CH$_2$)$_x$—C(O)—OC$_{1-6}$ alkyl, —(CH$_2$)$_x$—OH, —(CH$_2$)$_x$—CN, —OCH$_2$C$_6$H$_5$, —CHO, —(CH$_2$)$_x$—COOH, —(CH$_2$)$_x$—COOC$_{1-6}$ alkyl, —(CH$_2$)$_y$—CO—COOH, and —(CH$_2$)$_y$—C(H)(OH)—COOH; or any two adjacent R$^4$, R$^5$, R$^6$, and R$^7$, together with the atoms they attach to, form a five to seven-membered carbocyclic ring;

x is a number from zero to six; and y is a number from zero to six;

or a pharmaceutically acceptable salt thereof;

provided that at least one of R$^2$, R$^3$, R$^4$, R$^5$, R$^6$, and R$^7$ is bromo.

In some embodiments of any of the above methods, the compound is of Formula (IV):

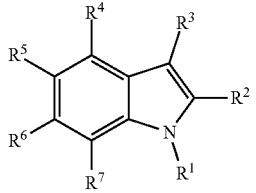

(IV)

wherein

R$^1$ is hydrogen, C$_{1-6}$ alkyl, or hydroxy;

R$^2$, R$^3$, R$^4$, R$^5$, R$^6$, and R$^7$ are independently selected from hydrogen, C$_{1-6}$alkyl, C$_{1-6}$alkoxy, amino, substituted amino, halogen, —(CH$_2$)$_x$—C(O)—OC$_{1-6}$ alkyl, —(CH$_2$)$_x$—OH, —(CH$_2$)$_x$—CN, —OCH$_2$C$_6$H$_5$, —CHO, —(CH$_2$)$_x$—COOH, —(CH$_2$)$_x$—COOC$_{1-6}$ alkyl, —(CH$_2$)$_y$—CO—COOH, and —(CH$_2$)$_y$—C(H)(OH)—COOH; or any two adjacent R$^4$, R$^5$, R$^6$, and R$^7$, together with the atoms they attach to, form a five to seven-membered carbocyclic ring;

x is a number from zero to six; and y is a number from zero to six;

or a pharmaceutically acceptable salt thereof;

provided that at least one of R$^2$, R$^3$, R$^4$, R$^5$, R$^6$, and R$^7$ is -CHO or —(CH$_2$)$_x$—COOH.

In some embodiments of any of the above methods, the compound is of Formula (V):

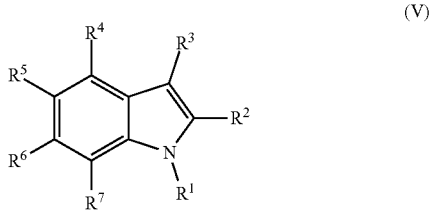

(V)

wherein

R$^1$ is hydrogen or C$_{1-6}$ alkyl;

R$^2$, R$^3$, R$^4$, R$^5$, R$^6$, and R$^7$ are independently selected from hydrogen, C$_{1-6}$alkyl, C$_{1-6}$alkoxy, —OCH$_2$C$_6$H$_5$, halogen, —CHO, —(CH$_2$)$_x$—COOH; and x is a number from zero to six;

or a pharmaceutically acceptable salt thereof.

In some embodiments of any of the above methods, the compound is of Formula (VI):

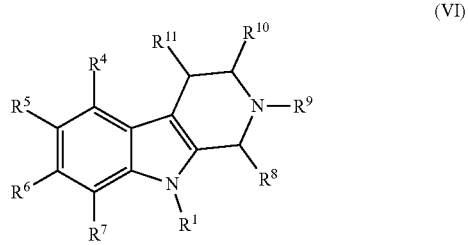

(VI)

wherein

R$^1$ is hydrogen or C$_{1-6}$ alkyl;

R$^4$, R$^5$, R$^6$, and R$^7$ are independently selected from hydrogen, C$_{1-6}$alkyl, C$_{1-6}$alkoxy, amino, substituted amino, halogen, heteroaryl, substituted heteroaryl, —(CH$_2$)$_x$—C(O)—OC$_{1-6}$ alkyl, —(CH$_2$)$_x$—OH, —(CH$_2$)$_x$—CN, —OCH$_2$C$_6$H$_5$, —OCOCH$_3$, —(CH$_2$)$_x$—CONH$_2$, —CHO, —(CH$_2$)$_x$—COOH, —(CH$_2$)$_x$—COOC$_{1-6}$ alkyl, —(CH$_2$)$_y$—CO—COOH, and —(CH$_2$)$_y$—C(H)(OH)—COOH;

R$^8$, R$^{10}$, and R$^{11}$ are independently selected from hydrogen, halogen, —(CH$_2$)$_x$—C(O)—OC$_{1-6}$ alkyl, —(CH$_2$)$_x$—OH, —(CH$_2$)$_x$—CN, —OCH$_2$C$_6$H$_5$, —OCOCH$_3$, —(CH$_2$)$_x$—CONH$_2$, —CHO, —(CH$_2$)$_x$—COOH, —(CH$_2$)$_x$—COOC$_{1-6}$ alkyl, —(CH$_2$)$_y$—CO—COOH, —(CH$_2$)$_y$—C(H)(OH)—COOH, phenyl, and substituted phenyl; wherein the substituted phenyl is substituted with 1-4 substituents selected from hydroxyl, C$_{1-6}$alkoxy, and C$_{1-6}$alkyl;

R$^9$ is hydrogen or C$_{1-6}$ alkyl;

x is a number from zero to six; and y is a number from zero to six;

or a pharmaceutically acceptable salt thereof.

In some embodiments, the compound is selected from Compounds 2, 10, 29, 38, 40, 41, 43, and 44. In some embodiments, the compound is Compound 2. In some embodiments, the compound is Compound 43. In some embodiments, the administering step is by injection, transdermal pump, transdermal patch, or a subdermal depot. In some embodiments, the administering step is by subcutaneous injection. In some embodiments, the subject is a mammal. In some embodiments, the subject is a human. In some embodiments, the method further comprises administering to the subject a second therapeutic agent.

In some embodiments, the compound of Formula (I) is a compound selected from those species described or exemplified in the detailed description below.

In a further aspect, the present disclosure provides a composition comprising a compound of Formula (I) or a pharmaceutically acceptable salt, solvate, or hydrate thereof. The compositions may further comprise a pharmaceutically acceptable excipient (such as pharmaceutically acceptable excipients suitable for injection). The present disclosure also provides a composition comprising a compound of Formula (I) or a pharmaceutically acceptable salt thereof for use as a medicament.

The present disclosure also provides a composition comprising a compound of Formula (I) or a pharmaceutically acceptable salt thereof and a pharmaceutically acceptable excipient, wherein the composition is suitable for local administration, such as injection (such as subcutaneous injection, intradermal injection, or intramuscular injection), transdermal pump, transdermal patch, or subdermal depot.

In another aspect, the present disclosure provides a composition comprising a compound of Formula (I) or a pharmaceutically acceptable salt thereof for use in therapy.

The present disclosure provides, in some embodiments, a composition comprising a compound of Formula (I) for non-surgical reduction or removal of one or more localized fat deposits in a subject. The present disclosure provides, in some embodiments, a composition comprising a compound of Formula (I) for reducing a subcutaneous fat deposit in a subject. The present disclosure provides, in some embodiments, a composition comprising a compound of Formula (I) for treating an adipose tissue disorder or an adipose tissue tumor in a subject. The present disclosure provides, in some embodiments, a composition comprising a compound of Formula (I) for decreasing submental fat deposit under a skin area in a subject. The present disclosure provides in some embodiments, a composition comprising a compound of Formula (I) for preventing or reducing a skin condition (including method of tightening skin and lax subcutaneous tissue) associated with aging in a subject. The present disclosure provides, in some embodiments, a composition comprising a compound of Formula (I) for the treatment or improvement of skin and soft tissue laxity due to aging, weight loss, genetic determinants or other disorder. The present disclosure provides, in some embodiments, a composition comprising a compound of Formula (I) for treating sleep apnea in a subject.

The present disclosure provides, in some embodiments, a composition comprising a compound of Formula (I) for the manufacture of a medicament for non-surgical reduction or removal of one or more localized fat deposits in a subject.

The present disclosure provides, in some embodiments, a composition comprising a compound of Formula (I) for the manufacture of a medicament for reducing a subcutaneous fat deposit in a subject. The present disclosure provides, in some embodiments, a composition comprising a compound of Formula (I) for the manufacture of a medicament for treating an adipose tissue disorder or an adipose tissue tumor in a subject. The present disclosure provides, in some embodiments, a composition comprising a compound of Formula (I) for the manufacture of a medicament for decreasing submental fat deposit under a skin area in a subject. The present disclosure provides in some embodiments, a composition comprising a compound of Formula (I) for the manufacture of a medicament for preventing or reducing a skin condition (including method of tightening skin and lax subcutaneous tissue) associated with aging in a subject. The present disclosure provides, in some embodiments, a composition comprising a compound of Formula (I) for the manufacture of a medicament for the treatment or improvement of skin and soft tissue laxity due to aging, weight loss, genetic determinants or other disorder. The present disclosure provides, in some embodiments, a composition comprising a compound of Formula (I) for the manufacture of a medicament for treating sleep apnea in a subject.

The present disclosure provides a kit for the reduction or removal of localized fat deposits and/or skin and soft tissue tightening in a subject. The present disclosure provides a kit comprising a container, wherein the container comprises a composition comprising a compound of Formula (I). The present disclosure provides a syringe comprising a composition comprising a compound of Formula (I). The present disclosure provides a unit dose comprising an amount of a composition comprising a compound of Formula (I).

Additional embodiments, features, and advantages of the invention will be apparent from the following detailed description and through practice of the invention.

For the sake of brevity, the disclosures of the publications cited in this specification, including patents, are herein incorporated by reference.

DEFINITIONS

Figure 1:
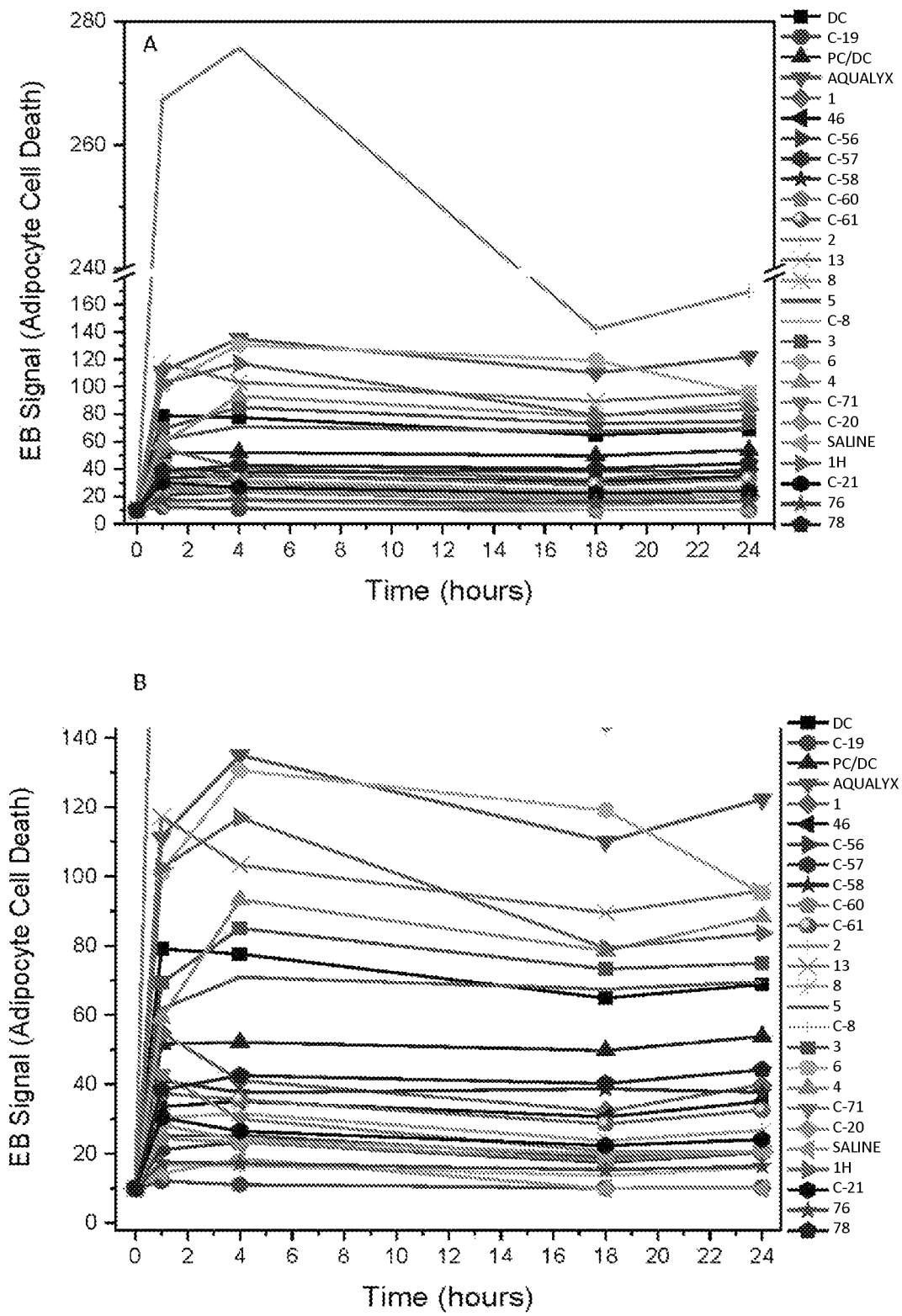
FIG. 1. (A) Change in Ethidium Bromide Fluorescence (EB) Intensity as a function of incubation time. Approximately 1.5-2 million adipocyte cells/ml were incubated for varying amounts of time in the presence of test compounds. (B) Magnified portion of FIG. 1A highlighting the diverse range of activity.

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), neopentyl (($CH_3)_3CCH_2$—), and n-hexyl ($CH_3(CH_2)_5$—).

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

"Amino" refers to the group —$NH_2$.

"Substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Carbaldehyde" and "carboxaldehyde" refer to the group —CHO.

"Halogen" refers to fluoro, chloro, bromo, and iodo.

The terms "carbocyclic ring", "carbocycle" or "carbocyclic ring system" denote a ring or ring system wherein the atoms forming the ring backbone are selected only from carbon. Unless otherwise indicated, a carbocyclic ring can be a saturated, partially unsaturated, or fully unsaturated ring. When a fully unsaturated carbocyclic ring satisfies Huckel's rule, then the ring is also called an "aromatic ring". "Saturated carbocyclic" refers to a ring having a backbone consisting of carbon atoms linked to one another by single bonds; unless otherwise specified, the remaining carbon valences are occupied by hydrogen atoms.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, benzimidazolyl, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxyl ester, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, sulfonylamino, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

Examples of heteroaryls include, but are not limited to, benzimidazole, pyrrole, imidazole, pyrazole, pyridine, pyrazine, pyrimidine, pyridazine, indolizine, isoindole, indole, purine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, piperidine, piperazine, phthalimide, 4,5,6,7-tetrahydrobenzo[b]thiophene, thiazole, thiophene, benzo[b]thiophene, and the like.

"Heterocycle," "heterocyclic," "heterocycloalkyl" or "heterocyclyl" refers to a saturated or partially unsaturated group having a single ring or multiple condensed rings, including fused, bridged, or spiro ring systems, and having from 3 to 20 ring atoms, including 1 to 10 hetero atoms. These ring atoms are selected from the group consisting of carbon, nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for N-oxide, —S(O)—, or —SO$_2$— moieties.

Examples of heterocycles include, but are not limited to, azetidine, dihydroindole, indazole, quinolizine, imidazolidine, imidazoline, piperidine, piperazine, indoline, 1,2,3,4-tetrahydroisoquinoline, thiazolidine, morpholinyl, thiomorpholinyl (also referred to as thiamorpholinyl), 1,1-dioxothiomorpholinyl, piperidinyl, pyrrolidine, tetrahydrofuranyl, and the like.

Where a heteroaryl or heterocyclyl group is "substituted," unless otherwise constrained by the definition for the heteroaryl or heterocyclic substituent, such heteroaryl or heterocyclic groups can be substituted with 1 to 5, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, azido, cyano, halogen, hydroxyl, oxo, thioketo, carboxyl, carboxyl ester, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, sulfonylamino, —SO-alkyl, —SO-substituted alkyl, —SO-aryl, —SO-heteroaryl, —SO-heterocyclyl, —SO$_2$-alkyl, —SO$_2$-substituted alkyl, —SO$_2$-aryl, —SO$_2$-heteroaryl, and —SO$_2$-heterocyclyl.

The term "substituted," when used to modify a specified group or radical, can mean that one or more hydrogen atoms of the specified group or radical are each, independently of one another, replaced with the same or different substituent groups.

In a certain embodiment, a group that is substituted has 1, 2, 3, or 4 substituents, 1, 2, or 3 substituents, 1 or 2 substituents, or 1 substituent.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a subject, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to the subject. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH-ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

As used herein, an "effective dosage" or "effective amount" of drug, compound, or pharmaceutical composition is an amount sufficient to effect beneficial or desired results. An effective dosage can be administered in one or more administrations. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during or after administration of the other treatment modality to the individual.

An "individual" or a "subject" is a mammal, more preferably a human. Mammals also include, but are not limited to, farm animals, sport animals, pets (such as cats, dogs, horses), primates, mice and rats.

As used herein and in the appended claims, the singular forms "a," "an," and "the" include plural reference unless the context clearly indicates otherwise.

Reference to "about" a value or parameter herein includes (and describes) embodiments that are directed to that value or parameter per se. For example, description referring to "about X" includes description of "X."

It is understood that aspect and variations of the invention described herein include "consisting" and/or "consisting essentially of" aspects and variations.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, 4$^{th}$ edition, New York: Oxford University Press, 2002, pp. 360-361, 1084-1085; Smith and March, March's Advanced Organic Chemistry: Reactions, Mechanisms, and Structure, 5$^{th}$ edition, Wiley-Interscience, 2001.

The nomenclature used herein to name the subject compounds is illustrated in the Examples herein. This nomenclature has generally been derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

DETAILED DESCRIPTION

The present invention provides methods and lypolytic indole compounds for reducing fat and/or tightening skin and lax soft tissue. Tissue specificity is an important consideration for developing lipolytic agents. Compounds that are not tissue-specific may have significant effect on neighboring tissues, for example necrosis of blood vessels, eccrine, glands, the reticular layer of the dermis, and demyelination of peripheral nerves, leading to side effects such as skin loss, itching, numbness, paresthesia, or even mandibular nerve palsy. It was surprisingly found that indole-based compounds are effective in killing adipocytes selectively and while in the meantime less toxic to muscle cells, nerve cells, and dermal cells. These compounds are therefore particularly suitable for fat reduction in vivo.

It was further surprisingly found that these indole compounds may have specific functional profiles in terms of potency, cell specificity, and cell killing characteristics (for example apoptotic, cytolytic, and/or pyroptotic), and that such functional profiles make them particularly suitable for fat reduction, skin and soft tissue tightening, and/or other applications discussed herein. A tailored treatment can therefore be developed depending on the amount of fat to be removed, the amount of anticipated post-treatment tissue laxity or firmness, as well as the effect on the skin surface area.

For example, in some embodiments, the indole compounds are apoptotic and non-inflammatory. It was previously shown that injection of currently available lipolysis drugs, such as deoxycholate or phosphatidylcholine combined with deoxycholate, produce significant side effects such as prominent and immediate swelling, bruising, pain, and inflammation. Fat-reducing injections that cause little or no swelling, bruising, or pain would therefore be particularly advantageous in many instances and would allow patients undergo more than one treatments in the desired region without severe sequelae. Examples of such desirable treatment regions include, for example, abdomen, thighs, flanks, and any other regions with significant adiposity.

In some embodiments, the indole compounds are cytolytic and inflammatory. The cytolytic effect, i.e., cell membrane rupture in soft tissue is most likely to cause significant inflammation. While this mechanism may lead to swelling and possibly bruising, the inflammation may lead to soft tissue tightening, skin surface area reduction, and the production of tissue firmness in the case of previous laxity. This is particularly useful when removing fat in areas involving skin laxity. For example, the degree of pendulous overhang of a region (such as a jowl or a "bat wing" of the arm) can be improved. An area which previously drooped below a normal axis can be lifted, with restoration of a normal contour.

In some embodiments, the indole compounds are pyroptotic, i.e., having a combined effect of apoptosis and cytolysis. Such compounds are particularly useful when both fat reduction and improvement and skin laxity are desirable.

Thus, the present invention in one aspect provides compositions suitable for reducing or removing localized fat deposits and/or tightening skin. In another aspect, there are provided methods for reducing or removing localized fat deposit and/or tightening skin. Also provided are kits, unit doses, and articles of manufacture useful for methods described herein.

Methods of the Present Invention

The present disclosure provides methods for using an indole compound. The methods include, but are not limited to, a method for non-surgical reduction of one or more localized fat deposits; a method for reducing a subcutaneous fat deposit; a method for treating an adipose tissue disorder or an adipose tissue tumor; a method for decreasing submental fat deposit under a skin area; a method of preventing or reducing a skin condition associated with aging; and a method for treating obstructive sleep apnea. The methods are described in more detail below.

The present disclosure provides methods for non-surgical reduction or removal of one or more localized fat deposits in a subject having localized fat accumulation comprising administering to a target site in the fat deposit a composition comprising an indole compound (such as a compound of Formula (I)). In some embodiments, the method comprises administering a compound of any one of Formula (II), (III), (IV), (V) and (VI) or any one of Compounds 2, 10, 29, 38, 40, 41, 43, and 44. In some embodiments, there is provided a method for non-surgical reduction or removal of one or more localized fat deposits in a subject having localized fat accumulation comprising administering to a target site in the fat deposit a composition comprising a compound of Formula (II). In some embodiments, there is provided a method for non-surgical reduction or removal of one or more localized fat deposits in a subject having localized fat accumulation comprising administering to a target site in the fat deposit a composition comprising a compound of Formula (III). In some embodiments, there is provided a method for non-surgical reduction or removal of one or more localized fat deposits in a subject having localized fat accumulation comprising administering to a target site in the fat deposit a composition comprising a compound of Formula (IV). In some embodiments, there is provided a method for non-surgical reduction or removal of one or more localized fat deposits in a subject having localized fat accumulation comprising administering to a target site in the fat deposit a composition comprising a compound of Formula (V). In some embodiments, there is provided a method for non-surgical reduction or removal of one or more localized fat deposits in a subject having localized fat accumulation comprising administering to a target site in the fat deposit a composition comprising a compound of Formula (VI). In some embodiments, there is provided a method for non-surgical reduction or removal of one or more localized fat deposits in a subject having localized fat accumulation comprising administering to a target site in the fat deposit a composition comprising compound 2. In some embodiments, there is provided a method for non-surgical reduction or removal of one or more localized fat deposits in a subject having localized fat accumulation comprising administering to a target site in the fat deposit a composition comprising compound 10. In some embodiments, there is provided a method for non-surgical reduction or removal of one or more localized fat deposits in a subject having localized fat accumulation comprising administering to a target site in the fat deposit a composition comprising compound 29. In some embodiments, there is provided a method for non-surgical reduction or removal of one or more localized fat deposits in a subject having localized fat accumulation comprising administering to a target site in the fat deposit a composition comprising compound 38. In some embodiments, there is provided a method for non-surgical reduction or removal of one or more localized fat deposits in a subject having localized fat accumulation comprising administering to a target site in the fat deposit a composition comprising compound 40. In some embodiments, there is provided a method for non-surgical reduction or removal of one or more localized fat deposits in a subject having localized fat accumulation comprising administering to a target site in the fat deposit a composition comprising compound 41. In some embodiments, there is provided a method for non-surgical reduction or removal of one or more localized fat deposits in a subject having localized fat accumulation comprising administering to a target site in the fat deposit a composition comprising compound 43. In some embodiments, there is provided a method for non-surgical reduction or removal of one or more localized fat deposits in a subject having localized fat accumulation comprising administering to a target site in the fat deposit a composition comprising compound 44. In some embodiments, the method is not used in conjunction with liposuction, lipoplasty, suction lipectomy, or ultrasonification. In some embodiments, the method herein is used in conjunction with liposuction, lipoplasty, or suction lipectonmy, or ultrasonification.

The present disclosure also provides a method for reducing a subcutaneous fat deposit in a subject having subcutaneous fat deposit comprising administering to a target site in the subcutaneous fat deposit a composition comprising an indole compound (such as a compound of Formula (I)). In some embodiments, the method comprises administering a compound of any one of Formula (II), (III), (IV), (V) and (VI) or any one of Compounds 2, 10, 29, 38, 40, 41, 43, and 44. In some embodiments, there is provided a method for reducing a subcutaneous fat deposit in a subject having subcutaneous fat deposit comprising administering to a target site in the subcutaneous fat deposit a composition comprising a compound of Formula (II). In some embodiments, there is provided a method for reducing a subcutaneous fat deposit in a subject having subcutaneous fat deposit comprising administering to a target site in the subcutaneous fat deposit a composition comprising a compound of Formula (III). In some embodiments, there is provided a method for reducing a subcutaneous fat deposit in a subject having subcutaneous fat deposit comprising administering to a target site in the subcutaneous fat deposit a composition comprising a compound of Formula (IV). In some embodiments, there is provided a method for reducing a subcutaneous fat deposit in a subject having subcutaneous fat deposit comprising administering to a target site in the subcutaneous fat deposit a composition comprising a compound of Formula (V). In some embodiments, there is provided a method for reducing a subcutaneous fat deposit in a subject having subcutaneous fat deposit comprising administering to a target site in the subcutaneous fat deposit a composition comprising a compound of Formula (VI). In some embodiments, there is provided a method for reducing a subcutaneous fat deposit in a subject having subcutaneous fat deposit comprising administering to a target site in the subcutaneous fat deposit a composition comprising compound 2. In some embodiments, there is provided a method for reducing a subcutaneous fat deposit in a subject having subcutaneous fat deposit comprising administering to a target site in the subcutaneous fat deposit a composition comprising compound 10. In some embodiments, there is provided a method for reducing a subcutaneous fat deposit in a subject having subcutaneous fat deposit comprising administering to a target site in the subcutaneous fat deposit a composition comprising compound 29. In some embodiments, there is provided a method for reducing a subcutaneous fat deposit in a subject having subcutaneous fat deposit comprising administering to a target site in the subcutaneous fat deposit a composition comprising compound 38. In some embodiments, there is provided a method for reducing a subcutaneous fat deposit in a subject having subcutaneous fat deposit comprising administering to a target site in the subcutaneous fat deposit a composition comprising compound 40. In some embodiments, there is provided a method for reducing a subcutaneous fat deposit in a subject having subcutaneous fat deposit comprising administering to a target site in the subcutaneous fat deposit a composition comprising compound 41. In some embodiments, there is provided a method for reducing a subcutaneous fat deposit in a subject having subcutaneous fat deposit comprising administering to a target site in the subcutaneous fat deposit a composition comprising compound 43. In some embodiments, there is provided a method for reducing a subcutaneous fat deposit in a subject having subcutaneous fat deposit comprising administering to a target site in the subcutaneous fat deposit a composition comprising compound 44. The methods described herein, in some embodiments, are useful for one or more of the following: 1) killing fat cells in a localized region; 2) dissolving fat in the localized region; and/or 3) for cosmetic purposes.

Adipose tissue (or body fat, or fat deposit, or fat) is loose connective tissue containing adipocytes. Adipose tissue can be found, for example, at the skin (subcutaneous fat), around internal organs (visceral fat), in bone marrow (yellow bone marrow) and in breast tissue. The present methods can be used for reducing fat deposit in any of these adipose tissues. The fat to be reduced or removed can be of varying hardness, depending on its contents. In certain embodiments, the fat deposit is soft fat. In certain embodiments, the fat deposit is fibrotic fat. While adipocytes are one component of the fatty layer, there are many different cell types in the hypodermis. About 18% of these cells are adipocytes. There is also a fibroseptal network—the collagenous framework in which the adipocytes reside. This layer is also known as the stromal vascular fraction. The present methods can be used for reducing the fibroseptal network.

The compositions and methods can be used to treat any adipose condition in a subject. Adipose conditions include, for example, disorders such as metabolic syndrome, obesity, fat redistribution syndrome, eyelid fat herniation, lipoma, herniation, cellulite, lipodystrophy (including buffalo hump lipodystrophy), dorsocervical fat, visceral adiposity, breast enlargement, hyperadiposity, diffused body fat around trunk and arms, fat deposits associated with cellulite, Dercum's disease, Madelung's neck, lipedema, piezogenic nodules, Launois Cleret syndrome, and xanthelasma.

The present disclosure also provides for a method for treating an adipose tissue disorder or an adipose tissue tumor in a subject comprising locally administering to the subject a composition comprising an indole compound (such as a compound of Formula (I)). In some embodiments, the method comprises administering a compound of any one of Formula (II), (III), (IV), (V) and (VI) or any one of Compounds 2, 10, 29, 38, 40, 41, 43, and 44. In some embodiments, there is provided a method for treating an adipose tissue disorder or an adipose tissue tumor in a subject comprising locally administering to the subject a composition comprising a compound of Formula (II). In some embodiments, there is provided a method for treating an adipose tissue disorder or an adipose tissue tumor in a subject comprising locally administering to the subject a composition comprising a compound of Formula (III). In some embodiments, there is provided a method for treating an adipose tissue disorder or an adipose tissue tumor in a subject comprising locally administering to the subject a composition comprising a compound of Formula (IV). In some embodiments, there is provided a method for treating an adipose tissue disorder or an adipose tissue tumor in a subject comprising locally administering to the subject a composition comprising a compound of Formula (V). In some embodiments, there is provided a method for treating an adipose tissue disorder or an adipose tissue tumor in a subject comprising locally administering to the subject a composition comprising a compound of Formula (VI). In some embodiments, there is provided a method for treating an adipose tissue disorder or an adipose tissue tumor in a subject comprising locally administering to the subject a composition comprising compound 2. In some embodiments, there is provided a method for treating an adipose tissue disorder or an adipose tissue tumor in a subject comprising locally administering to the subject a composition comprising compound 10. In some embodiments, there is provided a method for treating an adipose tissue disorder or an adipose tissue tumor in a subject comprising locally administering to the subject a composition comprising compound 29. In some embodiments, there is provided a method for treating an adipose tissue disorder or an adipose tissue tumor in a subject comprising locally administering to the subject a composition comprising compound 38. In some embodiments, there is provided a method for treating an adipose tissue disorder or an adipose tissue tumor in a subject comprising locally administering to the subject a composition comprising compound 40. In some embodiments, there is provided a method for treating an adipose tissue disorder or an adipose tissue tumor in a subject comprising locally administering to the subject a composition comprising compound 41. In some embodiments, there is provided a method for treating an adipose tissue disorder or an adipose tissue tumor in a subject comprising locally administering to the subject a composition comprising compound 43. In some embodiments, there is provided a method for treating an adipose tissue disorder or an adipose tissue tumor in a subject comprising locally administering to the subject a composition comprising compound 44. In some embodiments, the method is for cosmetic purposes.

Adipose tissue disorders include, for example, disorders such as metabolic syndrome, familial lipomatosis, lipoma, Dercum's disease, Madelung's neck, lipedema, piezogenic nodule, xanthelasma, lipodystrophy, and cellulite. Adipose tissue disorders show, in contrast to the food-related obesity-correlated lipohypertrophy, tissue conditions or identities which can be pathologically differentiated unambiguously and which can be described by histological parameters of scarring and inflammation, but also by connective tissue encapsulations and by changes in the histological adipose tissue morphology itself.

A lipoma is an adipose tissue tumor, which is benign, slow-growing, usually spherical, possibly pedunculated (=I.

pendulum) or even villous (=I. arborescens, for example of the synovial villi) mesenchymal tumors composed of enlarged-adipose tissue cells, such as in a subcutaneous cell tissue, possibly with central ossification (=I. ossificans), becoming mucoid (=I. myxomatodes) or calcifying (=I. petrificans), also with increased connective tissue and capsule formation (=I. fibrosum), neoangiogenesis (=I. teleangiectodes), rarely showing malignant degeneration (=I. sarcomatodes, liposarcoma). A lipoma can be categorized as pathological because they grow and their connective tissue envelope may be painful per se, as well as the compression derived therefrom on blood vessels, which may cause neuralgia.

In some embodiments, the compositions can be used to treat an adipose condition, adipose tissue disorder, lipodystrophy, or adipose tissue tumor in various areas of a subject. For example, the compositions can be used to reduce or remove fat deposits localized under the eyes, in the lower face and jowls, under chin, under arm, buttock, calf, back, thigh, ankle, stomach, cheek, brow, "love-handles", ankles, lips, or trachea of a subject. In some embodiments, the compositions can be used to treat omental adipocyte hypertrophy. In some embodiments, areas of laxity with adjacent fat can be treated, such as the vagina, urethra, and uvula, with the compositions.

The total volume, unit dose and number of treatments administered may vary depending on the amount of fat in a target site, the location of the target site, type of fat composition, the degree of tissue laxity, and desired results. In general, the greater the amount of fat being treated, the greater the dose that is administered. The type of compound used will depend on the relative degree of fatty hypertrophy versus tissue laxity. The compositions and unit dosages herein may be administered to a subject as part of a treatment regimen or as an individual treatment session.

In some embodiments according to any one of the methods described herein, the method further includes a step of ascertaining the effectiveness of the method. In some embodiments, the effectiveness is determined by a physical measurement, such as MRI, high resolution ultrasound, or caliper. In some embodiments, the localized fat is reduced by at least 1%, 2%, 3%, 4%, 5%, 6%, 7%, 8%, 9%, or 10% of the volume, or by at least 1%, 2%, 3%, 4%, 5%, 6%, 7%, 8%, 9%, or 10% of its thickness, as determined by MRI or by caliper measurement. The % of the volume reduction can be determined by subtracting the volume after treatment (volume after treatment: Vf) and that of the baseline (initial volume or volume before treatment: Vi), divided by Vi and multiplied by 100. Similarly the % of the thickness reduction can be determined by subtracting the thickness after treatment (thickness after treatment: Tf) and that of the baseline (initial volume or volume before treatment: Ti), divided by Ti and multiplied by 100. As an example to determine percentage reduction in volume, if Vi is 6346.8 cc, Vf is 5376.6 cc, then the volume is reduced by 18%. Similarly to determine percentage reduction in thickness, if Ti is 17.2 mm, Tf is 14.1 mm, then the thickness is reduced by 15%.

The present disclosure provides for a method for decreasing submental fat deposit under a skin area in a subject comprising administering to a target site in the fat deposit a composition comprising an indole compound (such as a compound of Formula (I)). In some embodiments, the method comprises administering a compound of any one of Formula (II), (III), (IV), (V) and (VI) or any one of Compounds 2, 10, 29, 38, 40, 41, 43, and 44. In some embodiments, there is provided a method for decreasing submental fat deposit under a skin area in a subject comprising administering to a target site in the fat deposit a composition comprising a compound of Formula (II). In some embodiments, there is provided a method for decreasing submental fat deposit under a skin area in a subject comprising administering to a target site in the fat deposit a composition comprising a compound of Formula (III). In some embodiments, there is provided a method for decreasing submental fat deposit under a skin area in a subject comprising administering to a target site in the fat deposit a composition comprising a compound of Formula (IV). In some embodiments, there is provided a method for decreasing submental fat deposit under a skin area in a subject comprising administering to a target site in the fat deposit a composition comprising a compound of Formula (V). In some embodiments, there is provided a method for decreasing submental fat deposit under a skin area in a subject comprising administering to a target site in the fat deposit a composition comprising a compound of Formula (VI). In some embodiments, there is provided a method for decreasing submental fat deposit under a skin area in a subject comprising administering to a target site in the fat deposit a composition comprising compound 2. In some embodiments, there is provided a method for decreasing submental fat deposit under a skin area in a subject comprising administering to a target site in the fat deposit a composition comprising compound 10. In some embodiments, there is provided a method for decreasing submental fat deposit under a skin area in a subject comprising administering to a target site in the fat deposit a composition comprising compound 29. In some embodiments, there is provided a method for decreasing submental fat deposit under a skin area in a subject comprising administering to a target site in the fat deposit a composition comprising compound 38. In some embodiments, there is provided a method for decreasing submental fat deposit under a skin area in a subject comprising administering to a target site in the fat deposit a composition comprising compound 40. In some embodiments, there is provided a method for decreasing submental fat deposit under a skin area in a subject comprising administering to a target site in the fat deposit a composition comprising compound 41. In some embodiments, there is provided a method for decreasing submental fat deposit under a skin area in a subject comprising administering to a target site in the fat deposit a composition comprising compound 43. In some embodiments, there is provided a method for decreasing submental fat deposit under a skin area in a subject comprising administering to a target site in the fat deposit a composition comprising compound 44.

The methods described herein, in some embodiments, are useful for one or more of the following: 1) enhancing facial aesthetics through reduction of submental fat; and/or 2) decreasing submental fat deposit under a skin area in a subject, for enhancing the cosmetic appearance of a subject, or for providing a facial cosmetic benefit to a subject.

In some embodiments, the submental fat deposit treated by the methods of the present disclosure is cosmetically unappealing but is non-pathological and the reduction of it is to improve the appearance of the subject. In certain embodiments, the result is reduction of the appearance of a double chin. In some embodiments, the method is non-surgical and does not include liposuction.

In some embodiments, the method can further include a step of ascertaining the effectiveness of the method. In some embodiments, the effectiveness is determined by a physical measurement, such as MRI, high resolution ultrasound, or caliper. A thickness and/or volume of the submental fat deposit can be measured with magnetic resonance imaging (MRI), high resolution ultrasound, or by a caliper. The thicknesses and/or volumes of the submental fat deposit can be compared before and after the treatment to assess the effectiveness of the treatment. In some embodiments, the thickness and/or volume is reduced by at least about 10%, or by at least about 15%, 20%, 25%, 30%, 35%, 40%, 45%, or 50%.

The reduction of submental fat can enhance the facial appearance of said subject. In some embodiments, the enhanced facial appearance is due to the reduction of prominence of a double chin. In some embodiments, the effectiveness of the treatment can be assessed by visual inspection for a reduction of prominence of a double chin or lack of a double chin. The lessening of the double chin appearance may be determined by the improvement in the degree of the submental convexity of the area under the chin.

The present disclosure provides for a method for preventing or reducing a skin condition associated with aging in a subject comprising locally administering to the subject a composition comprising an indole compound (such as a compound of Formula (I)). The present disclosure also provides for a method for the treatment or improvement of skin and soft tissue laxity due to aging, weight loss, genetic determinants or other disorder. In some embodiments, the method comprises administering a compound of any one of Formula (II), (III), (IV), (V) and (VI) or any one of Compounds 2, 10, 29, 38, 40, 41, 43, and 44. In some embodiments, there is provided a method for preventing or reducing a skin condition associated with aging in a subject comprising locally administering to the subject a composition comprising a compound of Formula (II). In some embodiments, there is provided a method for preventing or reducing a skin condition associated with aging in a subject comprising locally administering to the subject a composition comprising a compound of Formula (III). In some embodiments, there is provided a method for preventing or reducing a skin condition associated with aging in a subject comprising locally administering to the subject a composition comprising a compound of Formula (VI). In some embodiments, there is provided a method for preventing or reducing a skin condition associated with aging in a subject comprising locally administering to the subject a composition comprising a compound of Formula (V). In some embodiments, there is provided a method for preventing or reducing a skin condition associated with aging in a subject comprising locally administering to the subject a composition comprising a compound of Formula (VI). In some embodiments, there is provided a method for preventing or reducing a skin condition associated with aging in a subject comprising locally administering to the subject a composition comprising compound 2. In some embodiments, there is provided a method for preventing or reducing a skin condition associated with aging in a subject comprising locally administering to the subject a composition comprising compound 10. In some embodiments, there is provided a method for preventing or reducing a skin condition associated with aging in a subject comprising locally administering to the subject a composition comprising compound 29. In some embodiments, there is provided a method for preventing or reducing a skin condition associated with aging in a subject comprising locally administering to the subject a composition comprising compound 38. In some embodiments, there is provided a method for preventing or reducing a skin condition associated with aging in a subject comprising locally administering to the subject a composition comprising compound 40. In some embodiments, there is provided a method for preventing or reducing a skin condition associated with aging in a subject comprising locally administering to the subject a composition comprising compound 41. In some embodiments, there is provided a method for preventing or reducing a skin condition associated with aging in a subject comprising locally administering to the subject a composition comprising compound 43. In some embodiments, there is provided a method for preventing or reducing a skin condition associated with aging in a subject comprising locally administering to the subject a composition comprising compound 44. For example, skin conditions associated with aging include loose skin, irregularities of the skin, and wrinkles.

The methods described herein, in some embodiments, are useful for one or more of the following: 1) rejuvenating skin; 2) skin and subcutaneous tissue tightening; 3) causing skin and soft tissue retraction in a body region containing fat deposits, such as localized fat, cellulite, or a postlipoplasty deformity; 4) alleviating skin conditions, including cellulite, rippling, divots (skin contour irregularities following lipoplasty), and protuberances; 5) removing localized excess skin; and/or 6) firming the skin and soft tissue.

In some embodiments, the compositions are administered locally to a target area to create an inflammatory response causing subcutaneous collagen deposition with subsequent soft tissue retraction. The formation of a scar results in skin and soft tissue tightening especially in areas where the skin is under little or no tension and provides little resistance to fibroseptal contraction. Such treatment may be relevant in a number of clinical scenarios such as, for example, commonly performed fat treatments, including, but not limited to, large volume liposuction. The latter may be associated with post-liposuction, or weight loss induced skin and soft tissue laxity. Thus, in some embodiments, a composition comprising a therapeutically effective amount of an indole compound may be administered to a liposuction site after completion of the liposuction procedure. In some embodiments, the indole compound is a compound of Formula (I). In some embodiments, the method comprises administering a compound of any one of Formula (II), (III), (IV), (V) and (VI) or any one of Compounds 2, 10, 29, 38, 40, 41, 43, and 44. In some embodiments, there is provided a method for local administration to a target area to create an inflammatory response causing subcutaneous collagen deposition with subsequent soft tissue retraction of a compound of Formula (II). In some embodiments, there is provided a method for local administration to a target area to create an inflammatory response causing subcutaneous collagen deposition with subsequent soft tissue retraction of a compound of Formula (III). In some embodiments, there is provided a method for local administration to a target area to create an inflammatory response causing subcutaneous collagen deposition with subsequent soft tissue retraction of a compound of Formula (IV). In some embodiments, there is provided a method for local administration to a target area to create an inflammatory response causing subcutaneous collagen deposition with subsequent soft tissue retraction of a compound of Formula (V). In some embodiments, there is provided a method for local administration to a target area to create an inflammatory response causing subcutaneous collagen deposition with subsequent soft tissue retraction of a compound of Formula (VI). In some embodiments, there is provided a method for local administration to a target area to create an inflammatory response causing subcutaneous collagen deposition with subsequent soft tissue retraction of compound 2. In some embodiments, there is provided a method for local administration to a target area to create an inflammatory response causing subcutaneous collagen deposition with subsequent soft tissue retraction of compound 10. In some embodiments, there is provided a method for local administration to a target area to create an inflammatory response causing subcutaneous collagen deposition with subsequent soft tissue retraction of compound 29. In some embodiments, there is provided a method for local administration to a target area to create an inflammatory response causing subcutaneous collagen deposition with subsequent soft tissue retraction of compound 38. In some embodiments, there is provided a method for local administration to a target area to create an inflammatory response causing subcutaneous collagen deposition with subsequent soft tissue retraction of compound 40. In some embodiments, there is provided a method for local administration to a target area to create an inflammatory response causing subcutaneous collagen deposition with subsequent soft tissue retraction of compound 41. In some embodiments, there is provided a method for local administration to a target area to create an inflammatory response causing subcutaneous collagen deposition with subsequent soft tissue retraction of compound 43. In some embodiments, there is provided a method for local administration to a target area to create an inflammatory response causing subcutaneous collagen deposition with subsequent soft tissue retraction of compound 44.

In some embodiments, the target area is an area under eye, under chin, under arm, buttock, calf, back, thigh, stomach, cheek, brow, or any other skin regions showing aging, wrinkles, loose skin or skin irregularity.

In some embodiments, the method can further include a step of ascertaining the effectiveness of the method. The present disclosure also provides a method for ascertaining the effectiveness of a therapy for preventing or reducing a skin condition associated with aging in a subject, comprising comparing the skin condition of the subject before therapy with the skin condition of the subject after therapy, wherein smooth skin retraction without rippling, crease, or local indentation in the subject after therapy indicates effective therapy. The comparison can be done by visual inspection or patient satisfaction surveys. Other methods of ascertaining the effectiveness of the method include high resolution ultrasound, MRI dermatological wrinkle scale, Canfield Vectra 3D® imaging system, and calipers. High resolution ultrasound can be used to measure the thickness of a fatty deposit at certain sites. MRI is currently the "gold standard" in measuring the depth and width of subcutaneous fat deposits in a given region. Canfield Vectra 3D® imaging system is a mathematical way of determine smoothness of skin. The system uses a quadratic equation to determine positive and negative variations to form a computer-generated ideal of smooth curved surface for a given photographed region. The "smoothness index" is a way to measure the pre-treatment variation from the ideal surface. After treatment, another 3D photo is taken. The treatment region is identified, and the equation can be used to determine the change/improvement in surface contour irregularity.

The present disclosure provides for a method for treating obstructive sleep apnea comprising locally administering to the subject a composition comprising an indole compound (such as a compound of Formula (I)). In some embodiments, the method comprises administering a compound of any one of Formula (II), (III), (IV), (V) and (VI) or any one of Compounds 2, 10, 29, 38, 40, 41, 43, and 44. In some embodiments, there is provided a method for a method for treating obstructive sleep apnea comprising locally administering to the subject a composition comprising a compound of Formula (II). In some embodiments, there is provided a method for a method for treating obstructive sleep apnea comprising locally administering to the subject a composition comprising a compound of Formula (III). In some embodiments, there is provided a method for a method for treating obstructive sleep apnea comprising locally administering to the subject a composition comprising a compound of Formula (IV). In some embodiments, there is provided a method for a method for treating obstructive sleep apnea comprising locally administering to the subject a composition comprising a compound of Formula (V). In some embodiments, there is provided a method for a method for treating obstructive sleep apnea comprising locally administering to the subject a composition comprising a compound of Formula (VI). In some embodiments, there is provided a method for a method for treating obstructive sleep apnea comprising locally administering to the subject a composition comprising compound 2. In some embodiments, there is provided a method for a method for treating obstructive sleep apnea comprising locally administering to the subject a composition comprising compound 10. In some embodiments, there is provided a method for a method for treating obstructive sleep apnea comprising locally administering to the subject a composition comprising compound 29. In some embodiments, there is provided a method for a method for treating obstructive sleep apnea comprising locally administering to the subject a composition comprising compound 38. In some embodiments, there is provided a method for a method for treating obstructive sleep apnea comprising locally administering to the subject a composition comprising compound 40. In some embodiments, there is provided a method for a method for treating obstructive sleep apnea comprising locally administering to the subject a composition comprising compound 41. In some embodiments, there is provided a method for a method for treating obstructive sleep apnea comprising locally administering to the subject a composition comprising compound 43. In some embodiments, there is provided a method for a method for treating obstructive sleep apnea comprising locally administering to the subject a composition comprising compound 44. Obstructive sleep apnea is characterized by repetitive pauses in breathing during sleep due to the obstruction and/or collapse of an upper airway (throat), usually accompanied by a reduction in blood oxygen saturation, and followed by an awakening to breathe. It is a dangerous (sometimes life threatening) condition that often affects obese people. Obese people have a large amount of fat around their trachea, and this fat may cause their airway to collapse when their muscles relax during sleep. In some embodiments, the compositions are used to treat obstructive sleep apnea by reducing fat around the trachea. In such embodiments, the composition is administered locally (e.g., via injection) to a target site of fat around the trachea in a therapeutically effective amount.

In the above methods, in some embodiments, the subject being treated is a mammal. Such mammal can be a human or an animal such as a primate (e.g., a monkey, chimpanzee, etc.), a domesticated animal (e.g., a dog, cat, horse, etc.), farm animal (e.g., goat, sheep, pig, cattle, etc.), or laboratory animal (e.g., mouse, rat, etc.). In some embodiments, a subject being treated is a human, a horse, a dog, or a cat. In some embodiments, a subject can be a male or female human. A subject can be a human of any age, such as young age, adolescent age, adult age, middle age, or old age. In some embodiments, the subject can be an age of 1-4, 5-9, 10-19, 20-29, 30-39, 40-49, 50-59, 60-69, 70-79, 80-89, or 90-100 years.

In some embodiments, a subject is overweight or obese. In some embodiments, a subject is of normal weight or underweight. Overweight or obesity can be assessed, for example, by BMI (body mass index). A method for calculating BMI includes dividing a person's body weight in kilograms by their height in meters squared (weight [kg]/height $[m]^2$). A BMI of 30 or more is considered obese; a BMI between 25 to 29.9 is considered overweight; a BMI between 18.5 to 24.9 is considered normal weight; a BMI under 18.5 is considered underweight. In some embodiments, a subject has a BMI over about 30, such as about 30 to about 50. In some embodiments, a subject has a BMI of about 25 to about 29.9. In some embodiments, a subject has a BMI under about 25.

In some embodiments, the subject has a fat deposit. In some embodiments, the subject has skin and soft tissue laxity. In some embodiments, the subject has a fat deposit and skin and soft tissue laxity.

A "target site" used herein refers to an area of the body at which the composition is applied. The target site can be located at the fat deposit and/or the skin area to be affected. The target site can be at different levels of the skin, such as epidermis, dermis, or hypodermis. The target site can be intradermal (within or between layers of skin).

In some embodiments, the compound is administered locally. "Local administration" used herein refers to administration of a substance to an area where the action of the substance is desired. Sometimes, administration of the substance is directly to the area where the action of the substance is desired. In some embodiments, the compositions are administered via a localized injection. However, other means of administering the compositions are also contemplated. For example, the compositions may be administered via a transdermal pump, a transdermal patch, or a subdermal depot. In some embodiments, the compositions are administered topically.

In some embodiments, the composition is administered transdermally or subcutaneously, via e.g., a subcutaneous injection using a syringe to a target site. In some embodiments, the composition is administered by injection at hypodermis level, injection into the superficial level to mid-layer of subcutaneous fat, mid-layer or deep layer of subcutaneous fat, or injection into the lipodystrophic region. The compositions may be administered at the same, adjacent, or nearby target sites at various intervals, dosages, volumes, as disclosed herein.

In some embodiments, a target site can be, for example, 0.1 cm×0.1 cm, to about 5 cm×5 cm before the procedure. In some embodiments, the target site can be 0.1 cm×0.1 cm, 0.5 cm×0.5 cm, 1 cm×1 cm, 2 cm×2 cm, 3 cm×3 cm, 4 cm×4 cm, or 5 cm×5 cm.

The compositions may be administered once or multiple times into the target site. In some embodiments, the compositions are administered at least 1, 2, 3, 4, 5, 6, 7, 8, 9, or 10 times to a target site. More than one administration can occur in a single week, month, year, 2-5 years, or 5-10 years. In some embodiments, the subject is given 1-100, 2-50, 3-30, 4-20, or 5-10 injections at a target site. This number of injections can occur over a period of 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, or 10 years. In some embodiments, the compositions are administered weekly or 1-8 weeks apart.

In some embodiments, the subject is given 1 to 10 injections with intervals of 1 to 12 weeks; or 2 to 8 injections with intervals of 2 to 10 weeks; or 2 to 6 injections with intervals of 2 to 8 weeks. In some embodiments, the subject is given 2 to 4 injections with intervals of 4 to 8 weeks.

The compositions can be administered at various levels below the dermis. In some embodiments, the compositions can be administered with a 2-15 mm injection depth. In some embodiments, the injection depth is 2-4, 4-6, 6-8, 8-10, 10-12, or 12-15 mm. In some embodiments, the injection depth is 4-10, 6-10, 2-8, or 6-8 mm.

The compositions can be administered anywhere within the fatty layer. Because some of the compositions have certain dispersion when injected in a depot manner, in some embodiments, the compositions are administered with multilevel depots. For example, one administration could be immediately under the skin in the superficial hypodermis; and another administration could be halfway through the hypodermis; and another administration could be deep, just above the fascia. The present disclosure provides a multi-level injection approach, using needles of different lengths.

The dose can depend on the following factors—the amount of fat present, the desired effect desire, and the concentration of the drug. In some embodiments, a solution for injection comprises about 1-100 mg/ml of the indole composition. In some embodiments, a solution for injection comprises about 1-5, 6-10, 11-15, or 16-20 mg/ml of the indole composition. In some embodiments, a solution for injection comprises about 21-30, 31-40, 41-50, 51-60, 61-70, 71-80, 81-90, or 91-100 mg/ml of the indole composition. In some embodiments, a solution for injection comprises about 8-12 or 10 mg/ml of the indole composition.

In some embodiments, the volume for each injection is about 0.1 ml to about 0.5 ml. In some embodiments, the total of an indole compound administered is between about 50 mg to about 100 mg, or from about 60 mg, 70 mg to about 90 mg, 80 mg, without limitation.

In some embodiments, the method comprises local injection to the target site, through a plurality of injection sites on the skin area, a composition comprising an effective amount of an indole compound, wherein the effective amount is from about 0.01 mg to about 10 mg per injection site. In some embodiments, the effective amount is at least about 0.5, 1, 2, 3, 4, 5, 6, 7, 8, 9, or 10 mg per injection site. In some embodiments, the effective amount if no more than about 0.5, 1, 2, 3, 4, 5, 6, 7, 8, 9, or 10 mg per injection site.

In some embodiments, the plurality of injection sites is substantially evenly distributed on the skin area. The term "substantially evenly" as used here, refers to injection sites in an area where there are substantially the same number of injection sites per unit of area. In one aspect, a number is substantially the same as another number is they are with about 5% or 10%, or 15% or 20%, or 25% difference.

In some embodiments, each injection site is from about 0.8 cm to about 1.2 cm distant from an adjacent injection site. In some embodiments, each injection site is from about 0.9 cm to about 1.1 cm distant from an adjacent injection site. In some embodiments, each injection site is about 1 cm distant from an adjacent injection site.

In some embodiments, the plurality of injection sites comprises at least 20 injection sites, or alternatively at least 25, 30, 35, 40, 45, 50, 55, 60, 70, 80, 90, 100, 150, 200, 250, 300, 350, 400, 450, or 500 injection sites. In some embodiments, the plurality of injection sites has of no more than about 100, 90, 80, 70, 60, 50, 45, 40, 35, 30, or 25 injection sites. In some embodiments, the plurality of injection sites has from about 40 to about 60 injection sites, or about 50 injection sites.

In some embodiments, each injection site receives from about 0.1 ml to about 0.5 ml of the composition. In some embodiments, each injection site receives from about 0.1 ml to about 0.25 ml, or alternatively from about 0.26 to about 0.5, or from about 0.2 to about 0.4 ml of the composition.

In some embodiments, the method utilizes a grid comprising a plurality of injection sites, each of which is from about 0.8 cm to about 1.5 cm distant from an adjacent injection site of the grid; and injecting, with a suitable needle, through each of the plurality of injection sites, into about half way into the target site, an effective amount of a composition comprising from about 0.5% to about 1% (w/w) of an indole compound, wherein each injection constitutes delivery of from about 0.1 ml to about 0.3 ml of the composition.

In some embodiments, the grid comprises at least 20 injection sites, or at least 25, 30, 35, 40, 45, 50, 55, 60, 70, 80, 90, or 100 injection sites. In some embodiments, the grid comprises no more than about 100, 90, 80, 70, 60, 50, 45, 40, 35, 30, or 25 injection sites. In some embodiments, the grid comprises from about 40 to about 60 injection sites, or about 50 injection sites.

An alternative pattern would be a multi-level injection, using an under-the-skin type delivery. These would be performed from a single entry site, and would be executed in a ray-type distribution, similar to liposuction. The value of treating multiple levels of adiposity has been recently shown, so a better and more uniform response can be obtained with this method. Also, drugs with poor dispersion can be better delivered to the target tissue this way.

In some embodiments, the method further comprises pretreating the area around the injection sites with a local anesthetic. Various anesthetics individually or in combination may be included in the composition such as: ropivacaine, articaine, benzocaine bupivacaine, chloroprocaine, etidocaine, hexylcaine, lontocaine, lidocatine, levobuivaciaine, mepivacaine, prilocaine, procaine, and tetracaine. In some embodiments, co-administration of an anesthetic either the composition can reduce the number of injections Indole Compounds and Compositions The present disclosure provides various indole compounds and compositions which are useful for the methods disclosed herein. An indole compound is a compound comprising an indole core. An indole core is shown below:

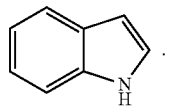

Formula (I)

The present disclosure provides a compound of Formula (I) and compositions comprising a compound of Formula (I):

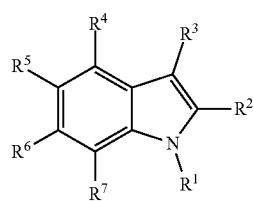

(I)

wherein
$R^1$ is hydrogen, $C_{1-6}$ alkyl, hydroxyl, or —$(CH_2)_x$—$CONH_2$;
$R^2$, $R^3$, $R^4$, $R^5$, $R^6$, and $R^7$ are independently selected from hydrogen, $C_{1-6}$alkyl, $C_{1-6}$alkoxy, amino, substituted amino, halogen, heteroaryl, substituted heteroaryl, —$(CH_2)_x$—$C(O)$—$OC_{1-6}$ alkyl, —$(CH_2)_x$—OH, —$(CH_2)_x$—CN, —$OCH_2C_6H_5$, —$OCOCH_3$, —$(CH_2)_x$—$CONH_2$, —CHO, —$(CH_2)_x$—COOH, —$(CH_2)_x$—$COOC_{1-6}$ alkyl, —$(CH_2)_y$—CO—COOH, and —$(CH_2)_y$—C(H)(OH)—COOH; or any two adjacent $R^4$, $R^5$, $R^6$, and $R^7$, together with the atoms they attach to, form a five to seven-membered carbocyclic ring; or $R^2$ and $R^3$, together with the atoms they attach to, form an unsubstituted or substituted five to seven-membered heterocyclyl ring;

x is a number from zero to six; and
y is a number from zero to six;
or a pharmaceutically acceptable salt thereof.

In some embodiments of Formula (I), $R^1$ is hydrogen. In some embodiments, $R^1$ is $C_{1-6}$ alkyl. In some embodiments, $R^1$ is methyl. In some embodiments, $R^1$ is hydroxy. In some embodiments, $R^1$ is —$(CH_2)_x$—$CONH_2$, wherein x is a number from zero to six. In some embodiments, $R^1$ is —$(CH_2)CONH_2$.

In some embodiments of Formula (I), at least one of $R^2$, $R^3$, $R^4$, $R^5$, $R^6$, and $R^7$ is selected from halogen, —CHO, and —$(CH_2)_x$—COOH.

In some embodiments of Formula (I), at least one of $R^2$, $R^3$, $R^4$, $R^5$, $R^6$, and $R^7$ is a halogen. In some embodiments, at least one of $R^2$, $R^3$, $R^4$, $R^5$, $R^6$, and $R^7$ is bromo. In some embodiments, $R^2$ is bromo. In some embodiments, $R^3$ is bromo. In some embodiments, $R^4$ is bromo. In some embodiments, $R^5$ is bromo. In some embodiments, $R^6$ is bromo. In some embodiments, $R^7$ is bromo.

In some embodiments of Formula (I), at least one of $R^2$, $R^3$, $R^4$, $R^5$, $R^6$, and $R^7$ is —CHO. In some embodiments, $R^2$ is —CHO. In some embodiments, $R^3$ is —CHO. In some embodiments, $R^4$ is —CHO. In some embodiments, $R^5$ is —CHO. In some embodiments, $R^6$ is —CHO. In some embodiments, $R^7$ is —CHO.

In some embodiments of Formula (I), at least one of $R^2$, $R^3$, $R^4$, $R^5$, $R^6$, and $R^7$ is —$(CH_2)_x$—COOH. In some embodiments, $R^2$ is —$(CH_2)_x$—COOH. In some embodiments, $R^3$ is —$(CH_2)_x$—COOH. In some embodiments, $R^4$ is —$(CH_2)_x$—COOH. In some embodiments, $R^5$ is —$(CH_2)_x$—COOH. In some embodiments, $R^6$ is —$(CH_2)_x$—COOH. In some embodiments, $R^7$ is —$(CH_2)_x$—COOH. In some embodiments, x is one to three. In some embodiments, x is one.

In some embodiments of Formula (I), at least one of $R^2$, $R^3$, $R^4$, $R^5$, $R^6$, and $R^7$ is heteroaryl or substituted heteroaryl. In some embodiments, at least one of $R^2$, $R^3$, $R^4$, $R^5$, $R^6$, and $R^7$ is benzimidazole or substituted benzimidazole. In some embodiments, one of $R^2$ and $R^3$ is benzimidazole or substituted benzimidazole. In some embodiments, the benzimidazole is substituted with $C_{1-6}$alkyl, halogen, —COOH, or —CHO.

In some embodiments of Formula (I), at least one of $R^2$, $R^3$, $R^4$, $R^5$, $R^6$, and $R^7$ is —$OCH_2C_6H_5$. In some embodiments, at least one of $R^2$, $R^3$, $R^4$, $R^5$, $R^6$, and $R^7$ is —$OCOCH_3$. In some embodiments, at least one of $R^2$, $R^3$, $R^4$, $R^5$, $R^6$, and $R^7$ is —$(CH_2)_x$—$CONH_2$. In some embodiments, at least one of $R^2$, $R^3$, $R^4$, $R^5$, $R^6$, and $R^7$ is —$(CH_2)_x$—$COOC_{1-6}$ alkyl.

In some embodiments of Formula (I), one of $R^2$, $R^3$, $R^4$, $R^5$, $R^6$, and $R^7$ is halogen, and the rest are hydrogen. In some embodiments, the halogen is bromo.

In some embodiments of Formula (I), one of $R^2$, $R^3$, $R^4$, $R^5$, $R^6$, and $R^7$ is halogen; and one of $R^2$, $R^3$, $R^4$, $R^5$, $R^6$, and $R^7$ is —CHO or —$(CH_2)_x$—COOH. In some embodiments, one of $R^2$, $R^3$, $R^4$, $R^5$, $R^6$, and $R^7$ is bromo; and one of $R^2$, $R^3$, $R^4$, $R^5$, $R^6$, and $R^7$ is —CHO or —$(CH_2)_x$—COOH. In some embodiments, one of $R^2$, $R^3$, $R^4$, $R^5$, $R^6$, and $R^7$ is bromo; and one of $R^2$, $R^3$, $R^4$, $R^5$, $R^6$, and $R^7$ is —$(CH_2)_x$—COOH. In some embodiments, one of $R^2$, $R^3$, $R^4$, $R^5$, $R^6$, and $R^7$ is bromo; and one of $R^2$, $R^3$, $R^4$, $R^5$, $R^6$, and $R^7$ is —$(CH_2)_x$—COOH.

In some embodiments of Formula (I), one of $R^2$, $R^3$, $R^4$, $R^5$, $R^6$, and $R^7$ is halogen; one of $R^2$, $R^3$, $R^4$, $R^5$, $R^6$, and $R^7$ is —CHO or —$(CH_2)_x$—COOH; and the rest are hydrogen. In some embodiments, one of $R^2$, $R^3$, $R^4$, $R^5$, $R^6$, and $R^7$ is bromo; one of $R^2$, $R^3$, $R^4$, $R^5$, $R^6$, and $R^7$ is —CHO or —$(CH_2)_x$—COOH; and the rest are hydrogen. In some embodiments, one of $R^2$, $R^3$, $R^4$, $R^5$, $R^6$, and $R^7$ is bromo; one of $R^2$, $R^3$, $R^4$, $R^5$, $R^6$, and $R^7$ is —$(CH_2)_x$—COOH; and the rest are hydrogen. In some embodiments, one of $R^2$, $R^3$, $R^4$, $R^5$, $R^6$, and $R^7$ is bromo; one of $R^2$, $R^3$, $R^4$, $R^5$, $R^6$, and $R^7$ is —$(CH_2)_x$—COOH; and the rest are hydrogen.

In some embodiments of Formula (I), one of $R^2$, $R^3$, $R^4$, $R^5$, $R^6$, and $R^7$ is —CHO or —$(CH_2)_x$—COOH, and the rest are hydrogen. In some embodiments, one of $R^2$, $R^3$, $R^4$, $R^5$, $R^6$, and $R^7$ is —CHO and the rest are hydrogen. In some embodiments, one of $R^2$, $R^3$, $R^4$, $R^5$, $R^6$, and $R^7$ is —$(CH_2)_x$—COOH and the rest are hydrogen.

In some embodiments of Formula (I), one of $R^2$, $R^3$, $R^4$, $R^5$, $R^6$, and $R^7$ is —CHO or —$(CH_2)_x$—COOH; and one of $R^2$, $R^3$, $R^4$, $R^5$, $R^6$, and $R^7$ is halogen or —$OCH_2C_6H_5$. In some embodiments, one of $R^2$, $R^3$, $R^4$, $R^5$, $R^6$, and $R^7$ is —CHO; and one of $R^2$, $R^3$, $R^4$, $R^5$, $R^6$, and $R^7$ is halogen or —$OCH_2C_6H_5$. In some embodiments, one of $R^2$, $R^3$, $R^4$, $R^5$, $R^6$, and $R^7$ is —$(CH_2)_x$—COOH; and one of $R^2$, $R^3$, $R^4$, $R^5$, $R^6$, and $R^7$ is halogen or —$OCH_2C_6H_5$.

In some embodiments of Formula (I), one of $R^2$, $R^3$, $R^4$, $R^5$, $R^6$, and $R^7$ is —CHO or —$(CH_2)_x$—COOH; one of $R^2$, $R^3$, $R^4$, $R^5$, $R^6$, and $R^7$ is halogen or —$OCH_2C_6H_5$; and the rest are hydrogen. In some embodiments, one of $R^2$, $R^3$, $R^4$, $R^5$, $R^6$, and $R^7$ is —CHO; one of $R^2$, $R^3$, $R^4$, $R^5$, $R^6$, and $R^7$ is halogen or —$OCH_2C_6H_5$; and the rest are hydrogen. In some embodiments, one of $R^2$, $R^3$, $R^4$, $R^5$, $R^6$, and $R^7$ is —$(CH_2)_x$—COOH; one of $R^2$, $R^3$, $R^4$, $R^5$, $R^6$, and $R^7$ is halogen or —$OCH_2C_6H_5$; and the rest are hydrogen.

In some embodiments of Formula (I), $R^2$ and $R^3$, together with the atoms they attach to, form a substituted six-membered heterocyclyl ring. In some embodiments, $R^2$ and $R^3$, together with the atoms they attach to, form a substituted six-membered heterocyclyl ring containing one nitrogen. In some embodiments, $R^2$ and $R^3$, together with the atoms they attach to, form

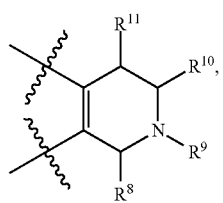

$R^8$, wherein $R^8$, $R^{10}$, and $R^{11}$ are independently selected from hydrogen, halogen, —$(CH_2)_x$—C(O)—$OC_{1-6}$ alkyl,
—$(CH_2)_x$—OH, —$(CH_2)_x$—CN, —$OCH_2C_6H_5$, —$OCOCH_3$, —$(CH_2)_x$—$CONH_2$, —CHO, —$(CH_2)_x$—COOH, —$(CH_2)_y$—CO—COOH, —$(CH_2)_y$—C(H)(OH)—COOH, phenyl, and substituted phenyl; wherein the substituted phenyl is substituted with 1-4 substituents selected from hydroxyl, $C_{1-6}$alkoxy, and $C_{1-6}$alkyl; and $R^9$ is hydrogen or $C_{1-6}$ alkyl.

In some embodiments of Formula (I), $R^2$ is selected from halogen, —CHO, and —$(CH_2)_x$—COOH and $R^1$ and $R^3$ are hydrogen. In some embodiments, $R^3$ is selected from halogen, —CHO, and —$(CH_2)_x$—COOH and $R^1$, $R^2$, and $R^4$ are hydrogen. In some embodiments, $R^4$ is selected from halogen, —CHO, and —$(CH_2)_x$—COOH and $R^3$, $R^5$, and $R^6$ are hydrogen. In some embodiments, $R^5$ is selected from halogen, —CHO, and —$(CH_2)_x$—COOH and $R^4$, $R^6$, and $R^7$ are hydrogen. In some embodiments, $R^6$ is selected from halogen, —CHO, and —$(CH_2)_x$—COOH and $R^4$, $R^5$, and $R^7$ are hydrogen. In some embodiments, $R^7$ is selected from halogen, —CHO, and —$(CH_2)_x$—COOH and $R^1$ and $R^6$ are hydrogen.

In some embodiments of Formula (I), $R^2$, $R^3$, $R^4$, $R^5$, $R^6$, and $R^7$ are hydrogen.

In some embodiments of Formula (I), $R^2$ is hydrogen. In some embodiments of Formula (I), $R^2$ is —CHO. In some embodiments of Formula (I), $R^2$ is —$(CH_2)_x$—COOH. In some embodiments of Formula (I), $R^2$ is —$(CH_2)_x$—$COOC_{1-6}$ alkyl. In some embodiments of Formula (I), $R^2$ is halogen. In some embodiments of Formula (II), $R^2$ is bromo. In some embodiments of Formula (I), $R^2$ is —$(CH_2)_y$—CO—COOH or —$(CH_2)_y$—C(H)(OH)—COOH. In some embodiments of Formula (I), $R^2$ is —$OCH_2C_6H_5$. In some embodiments of Formula (I), $R^2$ is —$(CH_2)_x$—OH or —$(CH_2)_x$—CN. In some embodiments of Formula (I), $R^2$ is heteroaryl or substituted heteroaryl. In some embodiments of Formula (I), $R^2$ is —$OCOCH_3$ or —$(CH_2)_x$—$CONH_2$. In some embodiments of Formula (I), $R^2$ is $C_{1-6}$alkyl, $C_{1-6}$alkoxy, amino, or substituted amino. In some embodiments of Formula (I), $R^2$ is —$(CH_2)_x$—C(O)—$OC_{1-6}$ alkyl.

In some embodiments of Formula (I), $R^3$ is hydrogen. In some embodiments of Formula (I), $R^3$ is —CHO. In some embodiments of Formula (I), $R^3$ is —$(CH_2)_x$—COOH. In some embodiments of Formula (I), $R^3$ is —$(CH_2)_x$—$COOC_{1-6}$ alkyl. In some embodiments of Formula (I), $R^3$ is halogen. In some embodiments of Formula (I), $R^3$ is bromo. In some embodiments of Formula (I), $R^3$ is —$(CH_2)_y$—CO—COOH or —$(CH_2)_y$—C(H)(OH)—COOH. In some embodiments of Formula (I), $R^3$ is —$OCH_2C_6H_5$. In some embodiments of Formula (I), $R^3$ is —$(CH_2)_x$—OH or —$(CH_2)_x$—CN. In some embodiments of Formula (I), $R^3$ is heteroaryl or substituted heteroaryl. In some embodiments of Formula (I), $R^3$ is —$OCOCH_3$ or —$(CH_2)_x$—$CONH_2$. In some embodiments of Formula (I), $R^3$ is $C_{1-6}$alkyl, $C_{1-6}$alkoxy, amino, or substituted amino. In some embodiments of Formula (I), $R^3$ is —$(CH_2)_x$—C(O)—$OC_{1-6}$ alkyl.

In some embodiments of Formula (I), $R^2$ and $R^3$, together with the atoms they attach to, form an unsubstituted five to seven-membered heterocyclyl ring. In some embodiments, $R^2$ and $R^3$, together with the atoms they attach to, form a substituted five to seven-membered heterocyclyl ring. In some embodiments, $R^2$ and $R^3$, together with the atoms they attach to, form a five-membered heterocyclyl ring. In some embodiments, $R^2$ and $R^3$, together with the atoms they attach to, form a six-membered heterocyclyl ring. In some embodiments, $R^2$ and $R^3$, together with the atoms they attach to, form a seven-membered heterocyclyl ring.

In some embodiments of Formula (I), $R^4$ is hydrogen. In some embodiments of Formula (I), $R^4$ is —CHO. In some embodiments of Formula (I), $R^4$ is —$(CH_2)_x$—COOH. In some embodiments of Formula (I), $R^4$ is —$(CH_2)_x$—COOC$_{1-6}$ alkyl. In some embodiments of Formula (I), $R^4$ is halogen. In some embodiments of Formula (I), $R^4$ is bromo. In some embodiments of Formula (I), $R^4$ is —$(CH_2)_y$—CO—COOH or —$(CH_2)_y$—C(H)(OH)—COOH. In some embodiments of Formula (I), $R^4$ is —$OCH_2C_6H_5$. In some embodiments of Formula (I), $R^4$ is —$(CH_2)_x$—OH or —$(CH_2)_x$—CN. In some embodiments of Formula (I), $R^4$ is heteroaryl or substituted heteroaryl. In some embodiments of Formula (I), $R^4$ is —$OCOCH_3$ or —$(CH_2)_x$—$CONH_2$. In some embodiments of Formula (I), $R^4$ is $C_{1-6}$alkyl, $C_{1-6}$alkoxy, amino, or substituted amino. In some embodiments of Formula (I), $R^4$ is —$(CH_2)_x$—C(O)—$OC_{1-6}$ alkyl.

In some embodiments of Formula (I), $R^5$ is hydrogen. In some embodiments of Formula (I), $R^5$ is —CHO. In some embodiments of Formula (I), $R^5$ is —$(CH_2)_x$—COOH. In some embodiments of Formula (I), $R^5$ is —$(CH_2)_x$—COOC$_{1-6}$ alkyl. In some embodiments of Formula (I), $R^5$ is halogen. In some embodiments of Formula (I), $R^5$ is bromo. In some embodiments of Formula (I), $R^5$ is —$(CH_2)_y$—CO—COOH or —$(CH_2)_y$—C(H)(OH)—COOH. In some embodiments of Formula (I), $R^5$ is —$OCH_2C_6H_5$. In some embodiments of Formula (I), $R^5$ is —$(CH_2)_x$—OH or —$(CH_2)_x$—CN. In some embodiments of Formula (I), $R^5$ is heteroaryl or substituted heteroaryl. In some embodiments of Formula (I), $R^5$ is —$OCOCH_3$ or —$(CH_2)_x$—$CONH_2$. In some embodiments of Formula (I), $R^5$ is $C_{1-6}$alkyl, $C_{1-6}$alkoxy, amino, or substituted amino. In some embodiments of Formula (I), $R^5$ is —$(CH_2)_x$—C(O)—$OC_{1-6}$ alkyl.

In some embodiments of Formula (I), $R^6$ is hydrogen. In some embodiments of Formula (I), $R^6$ is —CHO. In some embodiments of Formula (I), $R^6$ is —$(CH_2)_x$—COOH. In some embodiments of Formula (I), $R^6$ is —$(CH_2)_x$—COOC$_{1-6}$ alkyl. In some embodiments of Formula (I), $R^6$ is halogen. In some embodiments of Formula (I), $R^6$ is bromo. In some embodiments of Formula (I), $R^6$ is —$(CH_2)_y$—CO—COOH or —$(CH_2)_y$—C(H)(OH)—COOH. In some embodiments of Formula (I), $R^6$ is —$OCH_2C_6H_5$. In some embodiments of Formula (I), $R^6$ is —$(CH_2)_x$—OH or —$(CH_2)_x$—CN. In some embodiments of Formula (I), $R^6$ is heteroaryl or substituted heteroaryl. In some embodiments of Formula (I), $R^6$ is —$OCOCH_3$ or —$(CH_2)_x$—$CONH_2$. In some embodiments of Formula (I), $R^6$ is $C_{1-6}$alkyl, $C_{1-6}$alkoxy, amino, or substituted amino. In some embodiments of Formula (I), $R^6$ is —$(CH_2)_x$—C(O)—$OC_{1-6}$ alkyl.

In some embodiments of Formula (I), $R^7$ is hydrogen. In some embodiments of Formula (I), $R^7$ is —CHO. In some embodiments of Formula (I), $R^7$ is —$(CH_2)_x$—COOH. In some embodiments of Formula (I), $R^7$ is —$(CH_2)_x$—COOC$_{1-6}$ alkyl. In some embodiments of Formula (I), $R^7$ is halogen. In some embodiments of Formula (I), $R^7$ is bromo. In some embodiments of Formula (I), $R^7$ is —$(CH_2)_y$—CO—COOH or —$(CH_2)_y$—C(H)(OH)—COOH. In some embodiments of Formula (I), $R^7$ is —$OCH_2C_6H_5$. In some embodiments of Formula (I), $R^7$ is —$(CH_2)_x$—OH or —$(CH_2)_x$—CN. In some embodiments of Formula (I), $R^7$ is heteroaryl or substituted heteroaryl. In some embodiments of Formula (I), $R^7$ is —$OCOCH_3$ or —$(CH_2)_x$—$CONH_2$. In some embodiments of Formula (I), $R^7$ is $C_{1-6}$alkyl, $C_{1-6}$alkoxy, amino, or substituted amino. In some embodiments of Formula (I), $R^7$ is —$(CH_2)_x$—C(O)—$OC_{1-6}$ alkyl.

In some embodiments of Formula (I), $R^6$ and $R^7$, together with the atoms they attach to, form a five to seven-membered carbocyclic ring. In some embodiments, $R^6$ and $R^7$, together with the atoms they attach to, form a five-membered carbocyclic ring.

In some embodiments of Formula (I), $R^5$ and $R^6$, together with the atoms they attach to, form a five to seven-membered carbocyclic ring. In some embodiments, $R^5$ and $R^6$, together with the atoms they attach to, form a five-membered carbocyclic ring.

In some embodiments of Formula (I), $R^4$ and $R^5$, together with the atoms they attach to, form a five to seven-membered carbocyclic ring. In some embodiments, $R^4$ and $R^5$, together with the atoms they attach to, form a five-membered carbocyclic ring.

Formula (II)

The present disclosure provides a compound of Formula (II) and compositions comprising a compound of Formula (II):

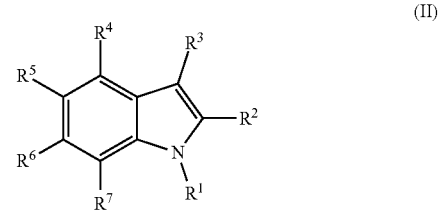

(II)

wherein $R^1$ is hydrogen, $C_{1-6}$ alkyl, or hydroxy;

$R^2$, $R^3$, $R^4$, $R^5$, $R^6$, and $R^7$ are independently selected from hydrogen, $C_{1-6}$alkyl, $C_{1-6}$alkoxy, amino, substituted amino, halogen, —$(CH_2)_x$—C(O)—$OC_{1-6}$ alkyl, —$(CH_2)_x$—OH, —$(CH_2)_x$—CN, —$OCH_2C_6H_5$, —CHO, —$(CH_2)_x$—COOH, —$(CH_2)_x$—COOC$_{1-6}$ alkyl, —$(CH_2)_y$—CO—COOH, and —$(CH_2)_y$—C(H)(OH)—COOH; or any two adjacent $R^4$, $R^5$, $R^6$, and $R^7$, together with the atoms they attach to, form a five to seven-membered carbocyclic ring;

x is a number from zero to six; and y is a number from zero to six;

or a pharmaceutically acceptable salt thereof.

In some embodiments of Formula (II), $R^1$ is hydrogen. In some embodiments, $R^1$ is $C_{1-6}$ alkyl. In some embodiments, $R^1$ is methyl. In some embodiments, $R^1$ is hydroxy.

In some embodiments of Formula (II), at least one of $R^2$, $R^3$, $R^4$, $R^5$, $R^6$, and $R^7$ is selected from halogen, —CHO, and —$(CH_2)_x$—COOH.

In some embodiments of Formula (II), at least one of $R^2$, $R^3$, $R^4$, $R^5$, $R^6$, and $R^7$ is a halogen. In some embodiments, at least one of $R^2$, $R^3$, $R^4$, $R^5$, $R^6$, and $R^7$ is bromo. In some embodiments, $R^2$ is bromo. In some embodiments, $R^3$ is bromo. In some embodiments, $R^4$ is bromo. In some embodiments, $R^5$ is bromo. In some embodiments, $R^6$ is bromo. In some embodiments, $R^7$ is bromo.

In some embodiments of Formula (II), at least one of $R^2$, $R^3$, $R^4$, $R^5$, $R^6$, and $R^7$ is —CHO. In some embodiments, $R^2$ is —CHO. In some embodiments, $R^3$ is —CHO. In some embodiments, $R^4$ is —CHO. In some embodiments, $R^5$ is —CHO. In some embodiments, $R^6$ is —CHO. In some embodiments, $R^7$ is —CHO.

In some embodiments of Formula (II), at least one of $R^2$, $R^3$, $R^4$, $R^5$, $R^6$, and $R^7$ is —$(CH_2)_x$—COOH. In some embodiments, $R^2$ is —$(CH_2)_x$—COOH. In some embodiments, $R^3$ is —$(CH_2)_x$—COOH. In some embodiments, $R^4$ is —$(CH_2)_x$—COOH. In some embodiments, $R^5$ is —$(CH_2)_x$—COOH. In some embodiments, $R^6$ is —$(CH_2)_x$—COOH.

In some embodiments, $R^7$ is —$(CH_2)_x$—COOH. In some embodiments, x is one to three. In some embodiments, x is one.

In some embodiments of Formula (II), at least one of $R^2$, $R^3$, $R^4$, $R^5$, $R^6$, and $R^7$ is —$OCH_2C_6H_5$. In some embodiments, at least one of $R^2$, $R^3$, $R^4$, $R^5$, $R^6$, and $R^7$ is —$(CH_2)_x$—$COOC_{1-6}$alkyl.

In some embodiments of Formula (II), one of $R^2$, $R^3$, $R^4$, $R^5$, $R^6$, and $R^7$ is halogen, and the rest are hydrogen. In some embodiments, the halogen is bromo.

In some embodiments of Formula (II), one of $R^2$, $R^3$, $R^4$, $R^5$, $R^6$, and $R^7$ is halogen; and one of $R^2$, $R^3$, $R^4$, $R^5$, $R^6$, and $R^7$ is —CHO or —$(CH_2)_x$—COOH. In some embodiments, one of $R^2$, $R^3$, $R^4$, $R^5$, $R^6$, and $R^7$ is bromo; and one of $R^2$, $R^3$, $R^4$, $R^5$, $R^6$, and $R^7$ is —CHO or —$(CH_2)_x$—COOH. In some embodiments, one of $R^2$, $R^3$, $R^4$, $R^5$, $R^6$, and $R^7$ is bromo; and one of $R^2$, $R^3$, $R^4$, $R^5$, $R^6$, and $R^7$ is —$(CH_2)_x$—COOH. In some embodiments, one of $R^2$, $R^3$, $R^4$, $R^5$, $R^6$, and $R^7$ is bromo; and one of $R^2$, $R^3$, $R^4$, $R^5$, $R^6$, and $R^7$ is —$(CH_2)_x$—COOH.

In some embodiments of Formula (II), one of $R^2$, $R^3$, $R^4$, $R^5$, $R^6$, and $R^7$ is halogen; one of $R^2$, $R^3$, $R^4$, $R^5$, $R^6$, and $R^7$ is —CHO or —$(CH_2)_x$—COOH; and the rest are hydrogen. In some embodiments, one of $R^2$, $R^3$, $R^4$, $R^5$, $R^6$, and $R^7$ is bromo; one of $R^2$, $R^3$, $R^4$, $R^5$, $R^6$, and $R^7$ is —CHO or —$(CH_2)_x$—COOH; and the rest are hydrogen. In some embodiments, one of $R^2$, $R^3$, $R^4$, $R^5$, $R^6$, and $R^7$ is bromo; one of $R^2$, $R^3$, $R^4$, $R^5$, $R^6$, and $R^7$ is —$(CH_2)_x$—COOH; and the rest are hydrogen. In some embodiments, one of $R^2$, $R^3$, $R^4$, $R^5$, $R^6$, and $R^7$ is bromo; one of $R^2$, $R^3$, $R^4$, $R^5$, $R^6$, and $R^7$ is —$(CH_2)_x$—COOH; and the rest are hydrogen.

In some embodiments of Formula (II), one of $R^2$, $R^3$, $R^4$, $R^5$, $R^6$, and $R^7$ is —CHO or —$(CH_2)_x$—COOH, and the rest are hydrogen. In some embodiments, one of $R^2$, $R^3$, $R^4$, $R^5$, $R^6$, and $R^7$ is —CHO and the rest are hydrogen. In some embodiments, one of $R^2$, $R^3$, $R^4$, $R^5$, $R^6$, and $R^7$ is —$(CH_2)_x$—COOH and the rest are hydrogen.

In some embodiments of Formula (II), one of $R^2$, $R^3$, $R^4$, $R^5$, $R^6$, and $R^7$ is —CHO or —$(CH_2)_x$—COOH; and one of $R^2$, $R^3$, $R^4$, $R^5$, $R^6$, and $R^7$ is halogen or —$OCH_2C_6H_5$. In some embodiments, one of $R^2$, $R^3$, $R^4$, $R^5$, $R^6$, and $R^7$ is —CHO; and one of $R^2$, $R^3$, $R^4$, $R^5$, $R^6$, and $R^7$ is halogen or —$OCH_2C_6H_5$. In some embodiments, one of $R^2$, $R^3$, $R^4$, $R^5$, $R^6$, and $R^7$ is —$(CH_2)_x$—COOH; and one of $R^2$, $R^3$, $R^4$, $R^5$, $R^6$, and $R^7$ is halogen or —$OCH_2C_6H_5$.

In some embodiments of Formula (II), one of $R^2$, $R^3$, $R^4$, $R^5$, $R^6$, and $R^7$ is —CHO or —$(CH_2)_x$—COOH; one of $R^2$, $R^3$, $R^4$, $R^5$, $R^6$, and $R^7$ is halogen or —$OCH_2C_6H_5$; and the rest are hydrogen. In some embodiments, one of $R^2$, $R^3$, $R^4$, $R^5$, $R^6$, and $R^7$ is —CHO; one of $R^2$, $R^3$, $R^4$, $R^5$, $R^6$, and $R^7$ is halogen or —$OCH_2C_6H_5$; and the rest are hydrogen. In some embodiments, one of $R^2$, $R^3$, $R^4$, $R^5$, $R^6$, and $R^7$ is —$(CH_2)_x$—COOH; one of $R^2$, $R^3$, $R^4$, $R^5$, $R^6$, and $R^7$ is halogen or —$OCH_2C_6H_5$; and the rest are hydrogen.

In some embodiments of Formula (II), $R^2$ is selected from halogen, —CHO, and —$(CH_2)_x$—COOH and $R^1$ and $R^3$ are hydrogen. In some embodiments, $R^3$ is selected from halogen, —CHO, and —$(CH_2)_x$—COOH and $R^1$, $R^2$, and $R^4$ are hydrogen. In some embodiments, $R^4$ is selected from halogen, —CHO, and —$(CH_2)_x$—COOH and $R^3$, $R^5$, and $R^6$ are hydrogen. In some embodiments, $R^5$ is selected from halogen, —CHO, and —$(CH_2)_x$—COOH and $R^4$, $R^6$, and $R^7$ are hydrogen. In some embodiments, $R^6$ is selected from halogen, —CHO, and —$(CH_2)_x$—COOH and $R^4$, $R^5$, and $R^7$ are hydrogen. In some embodiments, $R^7$ is selected from halogen, —CHO, and —$(CH_2)_x$—COOH and $R^1$ and $R^6$ are hydrogen.

In some embodiments of Formula (II), $R^2$, $R^3$, $R^4$, $R^5$, $R^6$, and $R^7$ are hydrogen.

In some embodiments of Formula (II), $R^2$ is hydrogen. In some embodiments of Formula (II), $R^2$ is —CHO. In some embodiments of Formula (II), $R^2$ is —$(CH_2)_x$—COOH. In some embodiments of Formula (II), $R^2$ is —$(CH_2)_x$—$COOC_{1-6}$ alkyl. In some embodiments of Formula (II), $R^2$ is halogen. In some embodiments of Formula (II), $R^2$ is bromo. In some embodiments of Formula (II), $R^2$ is —$(CH_2)_y$—CO—COOH or —$(CH_2)_y$—C(H)(OH)—COOH. In some embodiments of Formula (II), $R^2$ is —$OCH_2C_6H_5$. In some embodiments of Formula (II), $R^2$ is —$(CH_2)_x$—OH or —$(CH_2)_x$—CN. In some embodiments of Formula (II), $R^2$ is $C_{1-6}$alkyl, $C_{1-6}$alkoxy, amino, or substituted amino. In some embodiments of Formula (II), $R^2$ is —$(CH_2)_x$—C(O)—$OC_{1-6}$ alkyl.

In some embodiments of Formula (II), $R^3$ is hydrogen. In some embodiments of Formula (II), $R^3$ is —CHO. In some embodiments of Formula (II), $R^3$ is —$(CH_2)_x$—COOH. In some embodiments of Formula (II), $R^3$ is —$(CH_2)_x$—$COOC_{1-6}$ alkyl. In some embodiments of Formula (II), R is halogen. In some embodiments of Formula (II), $R^3$ is bromo. In some embodiments of Formula (II), $R^3$ is —$(CH_2)_y$—CO—COOH or —$(CH_2)_y$—C(H)(OH)—COOH. In some embodiments of Formula (II), $R^3$ is —$OCH_2C_6H_5$. In some embodiments of Formula (II), $R^3$ is —$(CH_2)_x$—OH or —$(CH_2)_x$—CN. In some embodiments of Formula (II), $R^3$ is $C_{1-6}$alkyl, $C_{1-6}$alkoxy, amino, or substituted amino. In some embodiments of Formula (II), $R^3$ is —$(CH_2)_x$—C(O)—$OC_{1-6}$ alkyl.

In some embodiments of Formula (II), $R^4$ is hydrogen. In some embodiments of Formula (II), $R^4$ is —CHO. In some embodiments of Formula (II), $R^4$ is —$(CH_2)_x$—COOH. In some embodiments of Formula (II), $R^4$ is —$(CH_2)_x$—$COOC_{1-6}$ alkyl. In some embodiments of Formula (II), $R^4$ is halogen. In some embodiments of Formula (II), $R^4$ is bromo. In some embodiments of Formula (II), $R^4$ is —$(CH_2)_y$—CO—COOH or —$(CH_2)_y$—C(H)(OH)—COOH. In some embodiments of Formula (II), $R^4$ is —$OCH_2C_6H_5$. In some embodiments of Formula (II), $R^4$ is —$(CH_2)_x$—OH or —$(CH_2)_x$—CN. In some embodiments of Formula (II), $R^4$ is $C_{1-6}$alkyl, $C_{1-6}$alkoxy, amino, or substituted amino. In some embodiments of Formula (II), $R^4$ is —$(CH_2)_x$—C(O)—$OC_{1-6}$ alkyl.

In some embodiments of Formula (II), $R^5$ is hydrogen. In some embodiments of Formula (II), $R^5$ is —CHO. In some embodiments of Formula (II), $R^5$ is —$(CH_2)_x$—COOH. In some embodiments of Formula (II), $R^5$ is —$(CH_2)_x$—$COOC_{1-6}$ alkyl. In some embodiments of Formula (II), $R^5$ is halogen. In some embodiments of Formula (II), $R^5$ is bromo. In some embodiments of Formula (II), $R^5$ is —$(CH_2)_y$—CO—COOH or —$(CH_2)_y$—C(H)(OH)—COOH. In some embodiments of Formula (II), $R^5$ is —$OCH_2C_6H_5$. In some embodiments of Formula (II), $R^5$ is —$(CH_2)_x$—OH or —$(CH_2)_x$—CN. In some embodiments of Formula (II), $R^5$ is $C_{1-6}$alkyl, $C_{1-6}$alkoxy, amino, or substituted amino. In some embodiments of Formula (II), $R^5$ is —$(CH_2)_x$—C(O)—$OC_{1-6}$ alkyl.

In some embodiments of Formula (II), $R^6$ is hydrogen. In some embodiments of Formula (II), $R^6$ is —CHO. In some embodiments of Formula (II), $R^6$ is —$(CH_2)_x$—COOH. In some embodiments of Formula (II), $R^6$ is —$(CH_2)_x$—$COOC_{1-6}$ alkyl. In some embodiments of Formula (II), $R^6$ is halogen. In some embodiments of Formula (II), $R^6$ is bromo. In some embodiments of Formula (II), $R^6$ is —$(CH_2)_y$—CO—COOH or —$(CH_2)_y$—C(H)(OH)—COOH. In some embodiments of Formula (II), $R^6$ is —$OCH_2C_6H_5$. In some embodiments of Formula (II), $R^6$ is —$(CH_2)_x$—OH or —$(CH_2)_x$—CN. In some embodiments of Formula (II), $R^6$ is $C_{1-6}$alkyl, $C_{1-6}$alkoxy, amino, or substituted amino. In some embodiments of Formula (II), $R^6$ is —$(CH_2)_x$—C(O)—$OC_{1-6}$ alkyl.

In some embodiments of Formula (II), $R^7$ is hydrogen. In some embodiments of Formula (II), $R^7$ is —CHO. In some embodiments of Formula (II), $R^7$ is —$(CH_2)_x$—COOH. In some embodiments of Formula (II), $R^7$ is —$(CH_2)_x$—$COOC_{1-6}$ alkyl. In some embodiments of Formula (II), $R^7$ is halogen. In some embodiments of Formula (II), $R^7$ is bromo. In some embodiments of Formula (II), $R^7$ is —$(CH_2)_y$—CO—COOH or —$(CH_2)_y$—C(H)(OH)—COOH. In some embodiments of Formula (II), $R^7$ is —$OCH_2C_6H_5$. In some embodiments of Formula (II), $R^7$ is —$(CH_2)_x$—OH or —$(CH_2)_x$—CN. In some embodiments of Formula (II), $R^7$ is $C_{1-6}$alkyl, $C_{1-6}$alkoxy, amino, or substituted amino. In some embodiments of Formula (II), $R^7$ is —$(CH_2)_x$—C(O)—$OC_{1-6}$ alkyl.

In some embodiments of Formula (II), $R^6$ and $R^7$, together with the atoms they attach to, form a five to seven-membered carbocyclic ring. In some embodiments, $R^6$ and $R^7$, together with the atoms they attach to, form a five-membered carbocyclic ring.

In some embodiments of Formula (II), $R^5$ and $R^6$, together with the atoms they attach to, form a five to seven-membered carbocyclic ring. In some embodiments, $R^5$ and $R^6$, together with the atoms they attach to, form a five-membered carbocyclic ring.

In some embodiments of Formula (II), $R^4$ and $R^5$, together with the atoms they attach to, form a five to seven-membered carbocyclic ring. In some embodiments, $R^4$ and $R^5$, together with the atoms they attach to, form a five-membered carbocyclic ring.

Formula (III)

The present disclosure provides a compound of Formula (III) and compositions comprising a compound of Formula (III):

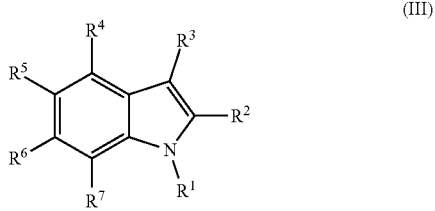

wherein
$R^1$ is hydrogen, $C_{1-6}$ alkyl, or hydroxy;
$R^2$, $R^3$, $R^4$, $R^5$, $R^6$, and $R^7$ are independently selected from hydrogen, $C_{1-6}$alkyl, $C_{1-6}$alkoxy, amino, substituted amino, halogen, —$(CH_2)_x$—C(O)—$OC_{1-6}$ alkyl, —$(CH_2)_x$—OH, —$(CH_2)_x$—CN, —$OCH_2C_6H_5$, —CHO, —$(CH_2)_x$—COOH, —$(CH_2)_x$—$COOC_{1-6}$ alkyl, —$(CH_2)_y$—CO—COOH, and —$(CH_2)_y$—C(H)(OH)—COOH; or
any two adjacent $R^4$, $R^5$, $R^6$, and $R^7$, together with the atoms they attach to, form a five to seven-membered carbocyclic ring;
x is a number from zero to six; and
y is a number from zero to six;
or a pharmaceutically acceptable salt thereof;
provided that at least one of $R^2$, $R^3$, $R^4$, $R^5$, $R^6$, and $R^7$ is bromo.

In some embodiments of Formula (III), $R^1$ is hydrogen. In some embodiments, $R^1$ is $C_{1-6}$ alkyl. In some embodiments, $R^1$ is methyl. In some embodiments, $R^1$ is hydroxy.

In Formula (III), at least one of $R^2$, $R^3$, $R^4$, $R^5$, $R^6$, and $R^7$ is bromo. In some embodiments, $R^2$ is bromo. In some embodiments, $R^3$ is bromo. In some embodiments, $R^4$ is bromo. In some embodiments, $R^5$ is bromo. In some embodiments, $R^6$ is bromo. In some embodiments, $R^7$ is bromo.

In some embodiments of Formula (III), one of $R^2$, $R^3$, $R^4$, $R^5$, $R^6$, and $R^7$ is bromo, and the rest are hydrogen.

In some embodiments of Formula (III), one of $R^2$, $R^3$, $R^4$, $R^5$, $R^6$, and $R^7$ is bromo and at least one of $R^2$, $R^3$, $R^4$, $R^5$, $R^6$, and $R^7$ is —CHO, —$(CH_2)_x$—COOH, or —$OCH_2C_6H_5$. In some embodiments, one of $R^2$, $R^3$, $R^4$, $R^5$, $R^6$, and $R^7$ is bromo and at least one of $R^2$, $R^3$, $R^4$, $R^5$, $R^6$, and $R^7$ is —CHO. In some embodiments, one of $R^2$, $R^3$, $R^4$, $R^5$, $R^6$, and $R^7$ is bromo and at least one of $R^2$, $R^3$, $R^4$, $R^5$, $R^6$, and $R^7$ is —$(CH_2)_x$—COOH. In some embodiments, one of $R^2$, $R^3$, $R^4$, $R^5$, $R^6$, and $R^7$ is bromo and at least one of $R^2$, $R^3$, $R^4$, $R^5$, $R^6$, and $R^7$ is —$OCH_2C_6H_5$.

In some embodiments of Formula (III), one of $R^2$, $R^3$, $R^4$, $R^5$, $R^6$, and $R^7$ is bromo; one of $R^2$, $R^3$, $R^4$, $R^5$, $R^6$, and $R^7$ is —CHO, —$(CH_2)_x$—COOH, or —$OCH_2C_6H_5$; and the rest are hydrogen. In some embodiments, one of $R^2$, $R^3$, $R^4$, $R^5$, $R^6$, and $R^7$ is bromo; one of $R^2$, $R^3$, $R^4$, $R^5$, $R^6$, and $R^7$ is-CHO; and the rest are hydrogen. In some embodiments, one of $R^2$, $R^3$, $R^4$, $R^5$, $R^6$, and $R^7$ is bromo; one of $R^2$, $R^3$, $R^4$, $R^5$, $R^6$, and $R^7$ is —$(CH_2)_x$—COOH; and the rest are hydrogen. In some embodiments, one of $R^2$, $R^3$, $R^4$, $R^5$, $R^6$, and $R^7$ is bromo; one of $R^2$, $R^3$, $R^4$, $R^5$, $R^6$, and $R^7$ is-$OCH_2C_6H_5$; and the rest are hydrogen.

In some embodiments of Formula (III), $R^2$ is bromo and $R^1$ and $R^3$ are hydrogen. In some embodiments, R is bromo and $R^1$, $R^2$, and $R^4$ are hydrogen. In some embodiments, $R^4$ is bromo and $R^3$, $R^5$, and $R^6$ are hydrogen. In some embodiments, $R^5$ is bromo and $R^4$, $R^6$, and $R^7$ are hydrogen. In some embodiments, $R^6$ is bromo and $R^4$, $R^5$, and $R^7$ are hydrogen. In some embodiments, $R^7$ is bromo and $R^1$ and $R^6$ are hydrogen.

In some embodiments of Formula (III), $R^2$ is hydrogen. In some embodiments of Formula (III), $R^2$ is —CHO. In some embodiments of Formula (III), $R^2$ is —$(CH_2)_x$—COOH. In some embodiments of Formula (III), $R^2$ is —$(CH_2)_x$—$COOC_{1-6}$ alkyl. In some embodiments of Formula (III), $R^2$ is halogen. In some embodiments of Formula (III), $R^2$ is bromo. In some embodiments of Formula (III), $R^2$ is —$(CH_2)_y$—CO—COOH or —$(CH_2)_y$—C(H)(OH)—COOH. In some embodiments of Formula (III), $R^2$ is —$OCH_2C_6H_5$. In some embodiments of Formula (III), $R^2$ is —$(CH_2)_x$—OH or —$(CH_2)_x$—CN. In some embodiments of Formula (III), $R^2$ is $C_{1-6}$alkyl, $C_{1-6}$alkoxy, amino, or substituted amino. In some embodiments of Formula (III), $R^2$ is —$(CH_2)_x$—C(O)—$OC_{1-6}$ alkyl.

In some embodiments of Formula (III), $R^3$ is hydrogen. In some embodiments of Formula (III), $R^3$ is —CHO. In some embodiments of Formula (III), $R^3$ is —$(CH_2)_x$—COOH. In some embodiments of Formula (III), $R^3$ is —$(CH_2)_x$—$COOC_{1-6}$ alkyl. In some embodiments of Formula (III), $R^3$ is halogen. In some embodiments of Formula (III), $R^3$ is bromo. In some embodiments of Formula (III), $R^3$ is —$(CH_2)_y$—CO—COOH or —$(CH_2)_y$—C(H)(OH)—COOH. In some embodiments of Formula (III), $R^3$ is —$OCH_2C_6H_5$. In some embodiments of Formula (III), $R^3$ is —$(CH_2)_x$—OH or —$(CH_2)_x$—CN. In some embodiments of Formula (III), $R^3$ is $C_{1-6}$alkyl, $C_{1-6}$alkoxy, amino, or substituted amino. In some embodiments of Formula (III), $R^3$ is —$(CH_2)_x$—C(O)—$OC_{1-6}$ alkyl.

In some embodiments of Formula (III), $R^4$ is hydrogen. In some embodiments of Formula (III), $R^4$ is —CHO. In some embodiments of Formula (III), $R^4$ is —$(CH_2)_x$—COOH. In some embodiments of Formula (III), $R^4$ is —$(CH_2)_x$—$COOC_{1-6}$ alkyl. In some embodiments of Formula (III), $R^4$ is halogen. In some embodiments of Formula (III), $R^4$ is bromo. In some embodiments of Formula (III), $R^4$ is —$(CH_2)_y$—CO—COOH or —$(CH_2)_y$—C(H)(OH)—COOH. In some embodiments of Formula (III), $R^4$ is —$OCH_2C_6H_5$. In some embodiments of Formula (III), $R^4$ is —$(CH_2)_x$—OH or —$(CH_2)_x$—CN. In some embodiments of Formula (III), $R^4$ is $C_{1-6}$alkyl, $C_{1-6}$alkoxy, amino, or substituted amino. In some embodiments of Formula (III), $R^4$ is —$(CH_2)_x$—C(O)—$OC_{1-6}$ alkyl.

In some embodiments of Formula (III), $R^5$ is hydrogen. In some embodiments of Formula (III), $R^5$ is —CHO. In some embodiments of Formula (III), $R^5$ is —$(CH_2)_x$—COOH. In some embodiments of Formula (III), $R^5$ is —$(CH_2)_x$—$COOC_{1-6}$ alkyl. In some embodiments of Formula (III), $R^5$ is halogen. In some embodiments of Formula (III), $R^5$ is bromo. In some embodiments of Formula (III), $R^5$ is —$(CH_2)_y$—CO—COOH or —$(CH_2)_y$—C(H)(OH)—COOH. In some embodiments of Formula (III), $R^5$ is —$OCH_2C_6H_5$. In some embodiments of Formula (III), $R^5$ is —$(CH_2)_x$—OH or —$(CH_2)_x$—CN. In some embodiments of Formula (III), $R^5$ is $C_{1-6}$alkyl, $C_{1-6}$alkoxy, amino, or substituted amino. In some embodiments of Formula (III), $R^5$ is —$(CH_2)_x$—C(O)—$OC_{1-6}$ alkyl.

In some embodiments of Formula (III), $R^6$ is hydrogen. In some embodiments of Formula (III), $R^6$ is —CHO. In some embodiments of Formula (III), $R^6$ is —$(CH_2)_x$—COOH. In some embodiments of Formula (III), $R^6$ is —$(CH_2)_x$—$COOC_{1-6}$ alkyl. In some embodiments of Formula (III), $R^6$ is halogen. In some embodiments of Formula (III), $R^6$ is bromo. In some embodiments of Formula (III), $R^6$ is —$(CH_2)_y$—CO—COOH or —$(CH_2)_y$—C(H)(OH)—COOH. In some embodiments of Formula (III), $R^6$ is —$OCH_2C_6H_5$. In some embodiments of Formula (III), $R^6$ is —$(CH_2)_x$—OH or —$(CH_2)_x$—CN. In some embodiments of Formula (III), $R^6$ is $C_{1-6}$alkyl, $C_{1-6}$alkoxy, amino, or substituted amino. In some embodiments of Formula (III), $R^6$ is —$(CH_2)_x$—C(O)—$OC_{1-6}$ alkyl.

In some embodiments of Formula (III), $R^7$ is hydrogen. In some embodiments of Formula (III), $R^7$ is —CHO. In some embodiments of Formula (III), $R^7$ is —$(CH_2)_x$—COOH. In some embodiments of Formula (III), $R^7$ is —$(CH_2)_x$—$COOC_{1-6}$ alkyl. In some embodiments of Formula (III), $R^7$ is halogen. In some embodiments of Formula (III), $R^7$ is bromo. In some embodiments of Formula (III), $R^7$ is —$(CH_2)_y$—CO—COOH or —$(CH_2)_y$—C(H)(OH)—COOH. In some embodiments of Formula (III), $R^7$ is —$OCH_2C_6H_5$. In some embodiments of Formula (III), $R^7$ is —$(CH_2)_x$—OH or —$(CH_2)_x$—CN. In some embodiments of Formula (III), $R^7$ is $C_{1-6}$alkyl, $C_{1-6}$alkoxy, amino, or substituted amino. In some embodiments of Formula (III), $R^7$ is —$(CH_2)_x$—C(O)—$OC_{1-6}$ alkyl.

In some embodiments of Formula (III), $R^6$ and $R^7$, together with the atoms they attach to, form a five to seven-membered carbocyclic ring. In some embodiments, $R^6$ and $R^7$, together with the atoms they attach to, form a five-membered carbocyclic ring.

In some embodiments of Formula (III), $R^5$ and $R^6$, together with the atoms they attach to, form a five to seven-membered carbocyclic ring. In some embodiments, $R^5$ and $R^6$, together with the atoms they attach to, form a five-membered carbocyclic ring.

In some embodiments of Formula (III), $R^4$ and $R^5$, together with the atoms they attach to, form a five to seven-membered carbocyclic ring. In some embodiments, $R^4$ and $R^5$, together with the atoms they attach to, form a five-membered carbocyclic ring.

Formula (IV)

The present disclosure provides a compound of Formula (IV) and compositions comprising a compound of Formula (IV):

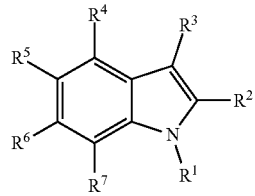

wherein
$R^1$ is hydrogen, $C_{1-6}$ alkyl, or hydroxy;
$R^2$, $R^3$, $R^4$, $R^5$, $R^6$, and $R^7$ are independently selected from hydrogen, $C_{1-6}$alkyl, $C_{1-6}$alkoxy, amino, substituted amino, halogen, —$(CH_2)_x$—C(O)—$OC_{1-6}$ alkyl, —$(CH_2)_x$—OH, —$(CH_2)_x$—CN, —$OCH_2C_6H_5$, —CHO, —$(CH_2)_x$—COOH, —$(CH_2)_x$—$COOC_{1-6}$ alkyl, —$(CH_2)_y$—CO—COOH, and —$(CH_2)_y$—C(H)(OH)—COOH; or
any two adjacent $R^4$, $R^5$, $R^6$, and $R^7$, together with the atoms they attach to, form a five to seven-membered carbocyclic ring;
x is a number from zero to six; and
y is a number from zero to six;
or a pharmaceutically acceptable salt thereof;
provided that at least one of $R^2$, $R^3$, $R^4$, $R^5$, $R^6$, and $R^7$ is -CHO or —$(CH_2)_x$—COOH.

In some embodiments of Formula (IV), $R^1$ is hydrogen. In some embodiments, $R^1$ is $C_{1-6}$ alkyl. In some embodiments, $R^1$ is methyl. In some embodiments, $R^1$ is hydroxy.

In Formula (IV), at least one of $R^2$, $R^3$, $R^4$, $R^5$, $R^6$, and $R^7$ is selected from —CHO, and —$(CH_2)_x$—COOH.

In some embodiments of Formula (IV), at least one of $R^2$, $R^3$, $R^4$, $R^5$, $R^6$, and $R^7$ is —CHO. In some embodiments, $R^2$ is —CHO. In some embodiments, R is —CHO. In some embodiments, $R^4$ is —CHO. In some embodiments, $R^5$ is —CHO. In some embodiments, $R^6$ is —CHO. In some embodiments, $R^7$ is —CHO.

In some embodiments of Formula (IV), at least one of $R^2$, $R^3$, $R^4$, $R^5$, $R^6$, and $R^7$ is —$(CH_2)_x$—COOH. In some embodiments, $R^2$ is —$(CH_2)_x$—COOH. In some embodiments, $R^3$ is —$(CH_2)_x$—COOH. In some embodiments, $R^4$ is —$(CH_2)_x$—COOH. In some embodiments, $R^5$ is —$(CH_2)_x$—COOH. In some embodiments, $R^6$ is —$(CH_2)_x$—COOH. In some embodiments, $R^7$ is —$(CH_2)_x$—COOH. In some embodiments, x is one to three. In some embodiments, x is one.

In some embodiments of Formula (IV), at least one of $R^2$, $R^3$, $R^4$, $R^5$, $R^6$, and $R^7$ is —$OCH_2C_6H_5$. In some embodiments of Formula (IV), at least one of $R^2$, $R^3$, $R^4$, $R^5$, $R^6$, and $R^7$ is halogen. In some embodiments of Formula (IV), at least one of $R^2$, $R^3$, $R^4$, $R^5$, $R^6$, and $R^7$ is -bromo. In some embodiments of Formula (IV), at least one of $R^2$, $R^3$, $R^4$, $R^5$, $R^6$, and $R^7$ is —$(CH_2)_x$—$COOC_{1-6}$alkyl.

In some embodiments of Formula (IV), one of $R^2$, $R^3$, $R^4$, $R^5$, $R^6$, and $R^7$ is —CHO or —$(CH_2)_x$—COOH, and the rest are hydrogen. In some embodiments, one of $R^2$, $R^3$, $R^4$, $R^5$, $R^6$, and $R^7$ is —CHO and the rest are hydrogen. In some embodiments, one of $R^2$, $R^3$, $R^4$, $R^5$, $R^6$, and $R^7$ is —$(CH_2)_x$—COOH and the rest are hydrogen.

In some embodiments of Formula (IV), one of $R^2$, $R^3$, $R^4$, $R^5$, $R^6$, and $R^7$ is —CHO or —$(CH_2)_x$—COOH and at least one of $R^2$, $R^3$, $R^4$, $R^5$, $R^6$, and $R^7$ is bromo or —$OCH_2C_6H_5$. In some embodiments, one of $R^2$, $R^3$, $R^4$, $R^5$, $R^6$, and $R^7$ is —CHO and at least one of $R^2$, $R^3$, $R^4$, $R^5$, $R^6$, and $R^7$ is bromo. In some embodiments, one of $R^2$, $R^3$, $R^4$, $R^5$, $R^6$, and $R^7$ is —CHO and at least one of $R^2$, $R^3$, $R^4$, $R^5$, $R^6$, and $R^7$ is —$OCH_2C_6H_5$. In some embodiments, one of $R^2$, $R^3$, $R^4$, $R^5$, $R^6$, and $R^7$ is —$(CH_2)_x$—COOH and at least one of $R^2$, $R^3$, $R^4$, $R^5$, $R^6$, and $R^7$ is bromo. In some embodiments, one of $R^2$, $R^3$, $R^4$, $R^5$, $R^6$, and $R^7$ is —$(CH_2)_x$—COOH and at least one of $R^2$, $R^3$, $R^4$, $R^5$, $R^6$, and $R^7$ is —$OCH_2C_6H_5$.

In some embodiments of Formula (IV), one of $R^2$, $R^3$, $R^4$, $R^5$, $R^6$, and $R^7$ is —CHO or —$(CH_2)_x$—COOH; one of $R^2$, $R^3$, $R^4$, $R^5$, $R^6$, and $R^7$ is halogen or —$OCH_2C_6H_5$; and the rest are hydrogen. In some embodiments, one of $R^2$, $R^3$, $R^4$, $R^5$, $R^6$, and $R^7$ is —CHO; one of $R^2$, $R^3$, $R^4$, $R^5$, $R^6$, and $R^7$ is halogen or —$OCH_2C_6H_5$; and the rest are hydrogen. In some embodiments, one of $R^2$, $R^3$, $R^4$, $R^5$, $R^6$, and $R^7$ is —$(CH_2)_x$—COOH; one of $R^2$, $R^3$, $R^4$, $R^5$, $R^6$, and $R^7$ is halogen or —$OCH_2C_6H_5$; and the rest are hydrogen.

In some embodiments of Formula (IV), $R^2$ is selected from —CHO and —$(CH_2)_x$—COOH and $R^1$ and $R^3$ are hydrogen. In some embodiments, $R^3$ is selected from —CHO and —$(CH_2)_x$—COOH and $R^1$, $R^2$, and $R^4$ are hydrogen. In some embodiments, $R^4$ is selected from —CHO, and —$(CH_2)_x$—COOH and $R^3$, $R^5$, and $R^6$ are hydrogen. In some embodiments, $R^5$ is selected from —CHO, and —$(CH_2)_x$—COOH and $R^4$, $R^6$, and $R^7$ are hydrogen. In some embodiments, $R^6$ is selected from —CHO and —$(CH_2)_x$—COOH and $R^4$, $R^5$, and $R^7$ are hydrogen. In some embodiments, $R^7$ is selected from —CHO and —$(CH_2)_x$—COOH and $R^1$ and $R^6$ are hydrogen.

In some embodiments of Formula (IV), $R^2$, $R^3$, $R^4$, $R^5$, $R^6$, and $R^7$ are hydrogen.

In some embodiments of Formula (IV), $R^2$ is hydrogen. In some embodiments of Formula (IV), $R^2$ is —CHO. In some embodiments of Formula (IV), $R^2$ is —$(CH_2)_x$—COOH. In some embodiments of Formula (IV), $R^2$ is —$(CH_2)_x$—$COOC_{1-6}$ alkyl. In some embodiments of Formula (IV), $R^2$ is halogen. In some embodiments of Formula (IV), $R^2$ is bromo. In some embodiments of Formula (IV), $R^2$ is —$(CH_2)_y$—CO—COOH or —$(CH_2)_y$—C(H)(OH)—COOH. In some embodiments of Formula (IV), $R^2$ is —$OCH_2C_6H_5$. In some embodiments of Formula (IV), $R^2$ is —$(CH_2)_x$—OH or —$(CH_2)_x$—CN. In some embodiments of Formula (IV), $R^2$ is $C_{1-6}$alkyl, $C_{1-6}$alkoxy, amino, or substituted amino. In some embodiments of Formula (IV), $R^2$ is —$(CH_2)_x$—C(O)—$OC_{1-6}$ alkyl.

In some embodiments of Formula (IV), $R^3$ is hydrogen. In some embodiments of Formula (IV), $R^3$ is —CHO. In some embodiments of Formula (IV), $R^3$ is —$(CH_2)_x$—COOH. In some embodiments of Formula (IV), $R^3$ is —$(CH_2)_x$—$COOC_{1-6}$ alkyl. In some embodiments of Formula (IV), $R^3$ is halogen. In some embodiments of Formula (IV), $R^3$ is bromo. In some embodiments of Formula (IV), $R^3$ is —$(CH_2)_y$—CO—COOH or —$(CH_2)_y$—C(H)(OH)—COOH. In some embodiments of Formula (IV), $R^3$ is —$OCH_2C_6H_5$. In some embodiments of Formula (IV), $R^3$ is —$(CH_2)_x$—OH or —$(CH_2)_x$—CN. In some embodiments of Formula (IV), $R^3$ is $C_{1-6}$alkyl, $C_{1-6}$alkoxy, amino, or substituted amino. In some embodiments of Formula (IV), $R^3$ is —$(CH_2)_x$—C(O)—$OC_{1-6}$ alkyl.

In some embodiments of Formula (IV), $R^4$ is hydrogen. In some embodiments of Formula (IV), $R^4$ is —CHO. In some embodiments of Formula (IV), $R^4$ is —$(CH_2)_x$—COOH. In some embodiments of Formula (IV), $R^4$ is —$(CH_2)_x$—$COOC_{1-6}$ alkyl. In some embodiments of Formula (IV), $R^4$ is halogen. In some embodiments of Formula (IV), $R^4$ is bromo. In some embodiments of Formula (IV), $R^4$ is —$(CH_2)_y$—CO—COOH or —$(CH_2)_y$—C(H)(OH)—COOH. In some embodiments of Formula (IV), $R^4$ is —$OCH_2C_6H_5$. In some embodiments of Formula (IV), $R^4$ is —$(CH_2)_x$—OH or —$(CH_2)_x$—CN. In some embodiments of Formula (IV), $R^4$ is $C_{1-6}$alkyl, $C_{1-6}$alkoxy, amino, or substituted amino. In some embodiments of Formula (IV), $R^4$ is —$(CH_2)_x$—C(O)—$OC_{1-6}$ alkyl.

In some embodiments of Formula (IV), $R^5$ is hydrogen. In some embodiments of Formula (IV), $R^5$ is —CHO. In some embodiments of Formula (IV), $R^5$ is —$(CH_2)_x$—COOH. In some embodiments of Formula (IV), $R^5$ is —$(CH_2)_x$—$COOC_{1-6}$ alkyl. In some embodiments of Formula (IV), $R^5$ is halogen. In some embodiments of Formula (IV), $R^5$ is bromo. In some embodiments of Formula (IV), $R^5$ is —$(CH_2)_y$—CO—COOH or —$(CH_2)_y$—C(H)(OH)—COOH. In some embodiments of Formula (IV), $R^5$ is —$OCH_2C_6H_5$. In some embodiments of Formula (IV), $R^5$ is —$(CH_2)_x$—OH or —$(CH_2)_x$—CN. In some embodiments of Formula (IV), $R^5$ is $C_{1-6}$alkyl, $C_{1-6}$alkoxy, amino, or substituted amino. In some embodiments of Formula (IV), $R^5$ is —$(CH_2)_x$—C(O)—$OC_{1-6}$ alkyl.

In some embodiments of Formula (IV), $R^6$ is hydrogen. In some embodiments of Formula (IV), $R^6$ is —CHO. In some embodiments of Formula (IV), $R^6$ is —$(CH_2)_x$—COOH. In some embodiments of Formula (IV), $R^6$ is —$(CH_2)_x$—$COOC_{1-6}$ alkyl. In some embodiments of Formula (IV), $R^6$ is halogen. In some embodiments of Formula (IV), $R^6$ is bromo. In some embodiments of Formula (IV), $R^6$ is —$(CH_2)_y$—CO—COOH or —$(CH_2)_y$—C(H)(OH)—COOH. In some embodiments of Formula (IV), $R^6$ is —$OCH_2C_6H_5$. In some embodiments of Formula (IV), $R^6$ is —$(CH_2)_x$—OH or —$(CH_2)_x$—CN. In some embodiments of Formula (IV), $R^6$ is $C_{1-6}$alkyl, $C_{1-6}$alkoxy, amino, or substituted amino. In some embodiments of Formula (IV), $R^6$ is —$(CH_2)_x$—C(O)—$OC_{1-6}$ alkyl.

In some embodiments of Formula (IV), $R^7$ is hydrogen. In some embodiments of Formula (IV), $R^7$ is —CHO. In some embodiments of Formula (IV), $R^7$ is —$(CH_2)_x$—COOH. In some embodiments of Formula (IV), $R^7$ is —$(CH_2)_x$—$COOC_{1-6}$ alkyl. In some embodiments of Formula (IV), $R^7$ is halogen. In some embodiments of Formula (IV), $R^7$ is bromo. In some embodiments of Formula (IV), $R^7$ is —$(CH_2)_y$—CO—COOH or —$(CH_2)_y$—C(H)(OH)—COOH. In some embodiments of Formula (IV), $R^7$ is —$OCH_2C_6H_5$. In some embodiments of Formula (IV), $R^7$ is —$(CH_2)_x$—OH or —$(CH_2)_x$—CN. In some embodiments of Formula (IV), $R^7$ is $C_{1-6}$alkyl, $C_{1-6}$alkoxy, amino, or substituted amino. In some embodiments of Formula (IV), $R^7$ is —$(CH_2)_x$—C(O)—$OC_{1-6}$ alkyl.

In some embodiments of Formula (IV), $R^6$ and $R^7$, together with the atoms they attach to, form a five to seven-membered carbocyclic ring. In some embodiments, $R^6$ and $R^7$, together with the atoms they attach to, form a five-membered carbocyclic ring.

In some embodiments of Formula (IV), $R^5$ and $R^6$, together with the atoms they attach to, form a five to seven-membered carbocyclic ring. In some embodiments, $R^5$ and $R^6$, together with the atoms they attach to, form a five-membered carbocyclic ring.

In some embodiments of Formula (IV), $R^4$ and $R^5$, together with the atoms they attach to, form a five to seven-membered carbocyclic ring. In some embodiments, $R^4$ and $R^5$, together with the atoms they attach to, form a five-membered carbocyclic ring.

Formula (V)

The present disclosure provides a compound of Formula (V) and compositions comprising a compound of Formula (V):

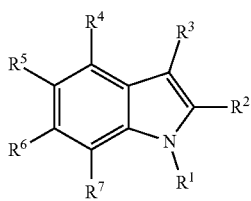

(V)

wherein
$R^1$ is hydrogen or $C_{1-6}$ alkyl;
$R^2$, $R^3$, $R^4$, $R^5$, $R^6$, and $R^7$ are independently selected from hydrogen, $C_{1-6}$alkyl, $C_{1-6}$alkoxy, —$OCH_2C_6H_5$, halogen, —CHO, —$(CH_2)_x$—COOH; and
x is a number from zero to six;
or a pharmaceutically acceptable salt thereof.

In some embodiments of Formula (V), $R^1$ is hydrogen. In some embodiments, $R^1$ is $C_{1-6}$ alkyl. In some embodiments, $R^1$ is methyl.

In some embodiments of Formula (V), at least one of $R^2$, $R^3$, $R^4$, $R^5$, $R^6$, and $R^7$ is halogen, —CHO or —$(CH_2)_x$—COOH. In some embodiments, at least one of $R^2$, $R^3$, $R^4$, $R^5$, $R^6$, and $R^7$ is bromo, —CHO or —$(CH_2)_x$—COOH. In some embodiments, at least one of $R^2$, $R^3$, $R^4$, $R^5$, $R^6$, and $R^7$ is bromo. In some embodiments, at least one of $R^2$, $R^3$, $R^4$, $R^5$, $R^6$, and $R^7$ is —CHO. In some embodiments, at least one of $R^2$, $R^3$, $R^4$, $R^5$, $R^6$, and $R^7$ is —$(CH_2)_x$—COOH.

In some embodiments of Formula (V), at least one of $R^2$, $R^3$, $R^4$, $R^5$, $R^6$, and $R^7$ is a halogen. In some embodiments, at least one of $R^2$, $R^3$, $R^4$, $R^5$, $R^6$, and $R^7$ is bromo. In some embodiments, $R^2$ is bromo. In some embodiments, $R^3$ is bromo. In some embodiments, $R^4$ is bromo. In some embodiments, $R^5$ is bromo. In some embodiments, $R^6$ is bromo. In some embodiments, $R^7$ is bromo.

In some embodiments of Formula (V), at least one of $R^2$, $R^3$, $R^4$, $R^5$, $R^6$, and $R^7$ is —CHO. In some embodiments, $R^2$ is —CHO. In some embodiments, $R^3$ is —CHO. In some embodiments, $R^4$ is —CHO. In some embodiments, $R^5$ is —CHO. In some embodiments, $R^6$ is —CHO. In some embodiments, $R^7$ is —CHO.

In some embodiments of Formula (V), at least one of $R^2$, $R^3$, $R^4$, $R^5$, $R^6$, and $R^7$ is —$(CH_2)_x$—COOH. In some embodiments, $R^2$ is —$(CH_2)_x$—COOH. In some embodiments, $R^3$ is —$(CH_2)_x$—COOH. In some embodiments, $R^4$ is —$(CH_2)_x$—COOH. In some embodiments, $R^5$ is —$(CH_2)_x$—COOH. In some embodiments, $R^6$ is —$(CH_2)_x$—COOH. In some embodiments, $R^7$ is —$(CH_2)_x$—COOH. In some embodiments, x is one to three. In some embodiments, x is one.

In some embodiments of Formula (V), at least one of $R^2$, $R^3$, $R^4$, $R^5$, $R^6$, and $R^7$ is —$OCH_2C_6H_5$.

In some embodiments of Formula (V), one of $R^2$, $R^3$, $R^4$, $R^5$, $R^6$, and $R^7$ is halogen, and the rest are hydrogen. In some embodiments, the halogen is bromo.

In some embodiments of Formula (V), one of $R^2$, $R^3$, $R^4$, $R^5$, $R^6$, and $R^7$ is halogen; and one of $R^2$, $R^3$, $R^4$, $R^5$, $R^6$, and $R^7$ is —CHO or —$(CH_2)_x$—COOH. In some embodiments, one of $R^2$, $R^3$, $R^4$, $R^5$, $R^6$, and $R^7$ is bromo; and one of $R^2$, $R^3$, $R^4$, $R^5$, $R^6$, and $R^7$ is —CHO or —$(CH_2)_x$—COOH. In some embodiments, one of $R^2$, $R^3$, $R^4$, $R^5$, $R^6$, and $R^7$ is bromo; and one of $R^2$, $R^3$, $R^4$, $R^5$, $R^6$, and $R^7$ is —$(CH_2)_x$—COOH. In some embodiments, one of $R^2$, $R^3$, $R^4$, $R^5$, $R^6$, and R is bromo; and one of $R^2$, $R^3$, $R^4$, $R^5$, $R^6$, and R is —$(CH_2)_x$—COOH.

In some embodiments of Formula (V), one of $R^2$, $R^3$, $R^4$, $R^5$, $R^6$, and $R^7$ is halogen; one of $R^2$, $R^3$, $R^4$, $R^5$, $R^6$, and $R^7$ is —CHO or —$(CH_2)_x$—COOH; and the rest are hydrogen. In some embodiments, one of $R^2$, $R^3$, $R^4$, $R^5$, $R^6$, and $R^7$ is bromo; one of $R^2$, $R^3$, $R^4$, $R^5$, $R^6$, and $R^7$ is —CHO or —$(CH_2)_x$—COOH; and the rest are hydrogen. In some embodiments, one of $R^2$, $R^3$, $R^4$, $R^5$, $R^6$, and $R^7$ is bromo; one of $R^2$, $R^3$, $R^4$, $R^5$, $R^6$, and $R^7$ is —$(CH_2)_x$—COOH; and the rest are hydrogen. In some embodiments, one of $R^2$, $R^3$, $R^4$, $R^5$, $R^6$, and $R^7$ is bromo; one of $R^2$, $R^3$, $R^4$, $R^5$, $R^6$, and $R^7$ is —$(CH_2)_x$—COOH; and the rest are hydrogen.

In some embodiments of Formula (V), one of $R^2$, $R^3$, $R^4$, $R^5$, $R^6$, and $R^7$ is —CHO or —$(CH_2)_x$—COOH, and the rest are hydrogen. In some embodiments, one of $R^2$, $R^3$, $R^4$, $R^5$, $R^6$, and $R^7$ is —CHO and the rest are hydrogen. In some embodiments, one of $R^2$, $R^3$, $R^4$, $R^5$, $R^6$, and $R^7$ is —$(CH_2)_x$—COOH and the rest are hydrogen.

In some embodiments of Formula (V), one of $R^2$, $R^3$, $R^4$, $R^5$, $R^6$, and $R^7$ is —CHO or —$(CH_2)_x$—COOH; and one of $R^2$, $R^3$, $R^4$, $R^5$, $R^6$, and $R^7$ is halogen or —$OCH_2C_6H_5$. In some embodiments, one of $R^2$, $R^3$, $R^4$, $R^5$, $R^6$, and $R^7$ is —CHO; and one of $R^2$, $R^3$, $R^4$, $R^5$, $R^6$, and $R^7$ is halogen or —$OCH_2C_6H_5$. In some embodiments, one of $R^2$, $R^3$, $R^4$, $R^5$, $R^6$, and $R^7$ is —$(CH_2)_x$—COOH; and one of $R^2$, $R^3$, $R^4$, $R^5$, $R^6$, and $R^7$ is halogen or —$OCH_2C_6H_5$.

In some embodiments of Formula (V), one of $R^2$, $R^3$, $R^4$, $R^5$, $R^6$, and $R^7$ is —CHO or —$(CH_2)_x$—COOH; one of $R^2$, $R^3$, $R^4$, $R^5$, $R^6$, and $R^7$ is halogen or —$OCH_2C_6H_5$; and the rest are hydrogen. In some embodiments, one of $R^2$, $R^3$, $R^4$, $R^5$, $R^6$, and $R^7$ is —CHO; one of $R^2$, $R^3$, $R^4$, $R^5$, $R^6$, and $R^7$ is halogen or —$OCH_2C_6H_5$; and the rest are hydrogen. In some embodiments, one of $R^2$, $R^3$, $R^4$, $R^5$, $R^6$, and $R^7$ is —$(CH_2)_x$—COOH; one of $R^2$, $R^3$, $R^4$, $R^5$, $R^6$, and $R^7$ is halogen or —$OCH_2C_6H_5$; and the rest are hydrogen.

In some embodiments of Formula (V), $R^2$ is selected from halogen, —CHO, and —$(CH_2)_x$—COOH and $R^1$ and $R^3$ are hydrogen. In some embodiments, $R^3$ is selected from halogen, —CHO, and —$(CH_2)_x$—COOH and $R^1$, $R^2$, and $R^4$ are hydrogen. In some embodiments, $R^4$ is selected from halogen, —CHO, and —$(CH_2)_x$—COOH and $R^3$, $R^5$, and $R^6$ are hydrogen. In some embodiments, $R^5$ is selected from halogen, —CHO, and —$(CH_2)_x$—COOH and $R^4$, $R^6$, and $R^7$ are hydrogen. In some embodiments, $R^6$ is selected from halogen, —CHO, and —$(CH_2)_x$—COOH and $R^4$, $R^5$, and $R^7$ are hydrogen. In some embodiments, $R^7$ is selected from halogen, —CHO, and —$(CH_2)_x$—COOH and $R^1$ and $R^6$ are hydrogen.

In some embodiments of Formula (V), $R^2$, $R^3$, $R^4$, $R^5$, $R^6$, and $R^7$ are hydrogen.

In some embodiments of Formula (V), $R^2$ is hydrogen. In some embodiments of Formula (V), $R^2$ is —CHO. In some embodiments of Formula (V), $R^2$ is —$(CH_2)_x$—COOH. In some embodiments of Formula (V), $R^2$ is halogen. In some embodiments of Formula (V), $R^2$ is bromo. In some embodiments of Formula (V), $R^2$ is —$OCH_2C_6H_5$. In some embodiments of Formula (V), $R^2$ is $C_{1-6}$alkyl or $C_{1-6}$alkoxy.

In some embodiments of Formula (V), $R^3$ is hydrogen. In some embodiments of Formula (V), $R^3$ is —CHO. In some embodiments of Formula (V), $R^3$ is —$(CH_2)_x$—COOH. In some embodiments of Formula (V), $R^3$ is halogen. In some embodiments of Formula (V), $R^3$ is bromo. In some embodiments of Formula (V), $R^3$ is —$OCH_2C_6H_5$. In some embodiments of Formula (V), $R^3$ is $C_{1-6}$alkyl or $C_{1-6}$alkoxy.

In some embodiments of Formula (V), $R^4$ is hydrogen. In some embodiments of Formula (V), $R^4$ is —CHO. In some embodiments of Formula (V), $R^4$ is —$(CH_2)_x$—COOH. In some embodiments of Formula (V), $R^4$ is halogen. In some embodiments of Formula (V), $R^4$ is bromo. In some embodiments of Formula (V), $R^4$ is —$OCH_2C_6H_5$. In some embodiments of Formula (V), $R^4$ is $C_{1-6}$alkyl or $C_{1-6}$alkoxy.

In some embodiments of Formula (V), $R^5$ is hydrogen. In some embodiments of Formula (V), $R^5$ is —CHO. In some embodiments of Formula (V), $R^5$ is —$(CH_2)_x$—COOH. In some embodiments of Formula (V), $R^5$ is halogen. In some embodiments of Formula (V), $R^5$ is bromo. In some embodiments of Formula (V), $R^5$ is —$OCH_2C_6H_5$. In some embodiments of Formula (V), $R^5$ is $C_{1-6}$alkyl or $C_{1-6}$alkoxy.

In some embodiments of Formula (V), $R^6$ is hydrogen. In some embodiments of Formula (V), $R^6$ is —CHO. In some embodiments of Formula (V), $R^6$ is —$(CH_2)_x$—COOH. In some embodiments of Formula (V), $R^6$ is halogen. In some embodiments of Formula (V), $R^6$ is bromo. In some embodiments of Formula (V), $R^6$ is —$OCH_2C_6H_5$. In some embodiments of Formula (V), $R^6$ is $C_{1-6}$alkyl or $C_{1-6}$alkoxy.

In some embodiments of Formula (V), $R^7$ is hydrogen. In some embodiments of Formula (V), $R^7$ is —CHO. In some embodiments of Formula (V), $R^7$ is —$(CH_2)_x$—COOH. In some embodiments of Formula (V), $R^7$ is halogen. In some embodiments of Formula (V), $R^7$ is bromo. In some embodiments of Formula (V), $R^7$ is —$OCH_2C_6H_5$. In some embodiments of Formula (V), $R^7$ is $C_{1-6}$alkyl or $C_{1-6}$alkoxy.

Formula (VI)

The present disclosure provides a compound of Formula (VI) and compositions comprising a compound of Formula (VI):

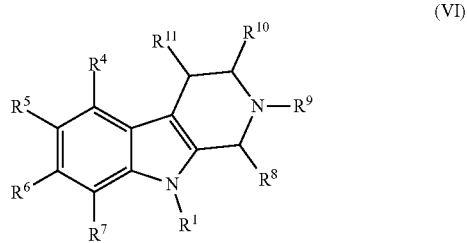

(VI)

wherein $R^1$ is hydrogen or $C_{1-6}$ alkyl;

$R^4$, $R^5$, $R^6$, and $R^7$ are independently selected from hydrogen, $C_{1-6}$alkyl, $C_{1-6}$alkoxy, amino, substituted amino, halogen, heteroaryl, substituted heteroaryl, —$(CH_2)_x$—C(O)—$OC_{1-6}$ alkyl, —$(CH_2)_x$—OH, —$(CH_2)_x$—CN, —$OCH_2C_6H_5$, —$OCOCH_3$, —$(CH_2)_x$—$CONH_2$, —CHO, —$(CH_2)_x$—COOH, —$(CH_2)_x$—$COOC_{1-6}$ alkyl, —$(CH_2)_y$—CO—COOH, and —$(CH_2)_y$—C(H)(OH)—COOH;

$R^8$, $R^{10}$, and $R^{11}$ are independently selected from hydrogen, halogen, —$(CH_2)_x$—C(O)—$OC_{1-6}$ alkyl, —$(CH_2)_x$—OH, —$(CH_2)_x$—CN, —$OCH_2C_6H_5$, —$OCOCH_3$, —$(CH_2)_x$—$CONH_2$, —CHO, —$(CH_2)_x$—COOH, —$(CH_2)_x$—$COOC_{1-6}$ alkyl, —$(CH_2)_y$—CO—COOH, —$(CH_2)_y$—C(H)(OH)—COOH, phenyl, and substituted phenyl; wherein the substituted phenyl is substituted with 1-4 substituents selected from hydroxyl, $C_{1-6}$alkoxy, and $C_{1-6}$alkyl;

$R^9$ is hydrogen or $C_{1-6}$ alkyl;

x is a number from zero to six; and y is a number from zero to six;

or a pharmaceutically acceptable salt thereof.

In some embodiments of Formula (VI), $R^1$ is hydrogen. In some embodiments, $R^1$ is $C_{1-6}$ alkyl. In some embodiments, $R^1$ is methyl.

In some embodiments of Formula (VI), at least one of $R^4$, $R^5$, $R^6$, $R^7$, $R^8$, $R^{10}$ and $R^{11}$ is halogen, —CHO or —$(CH_2)_x$—COOH. In some embodiments, at least one of $R^4$, $R^5$, $R^6$, $R^7$, $R^8$, $R^{10}$, and $R^{11}$ is bromo, —CHO or —$(CH_2)_x$—COOH. In some embodiments, at least one of $R^4$, $R^5$, $R^6$, $R^7$, $R^8$, $R^{10}$, and $R^{11}$ is bromo. In some embodiments, at least one of $R^4$, $R^5$, $R^6$, $R^7$, $R^8$, $R^{10}$, and $R^{11}$ is —CHO. In some embodiments, at least one of $R^4$, $R^5$, $R^6$, $R^7$, $R^8$, $R^{10}$, and $R^{11}$ is —$(CH_2)_x$—COOH. In some embodiments, at least one of $R^4$, $R^5$, $R^6$, $R^7$, $R^8$, $R^{10}$, and $R^{11}$ is —$(CH_2)_x$—$COOC_{1-6}$alkyl.

In some embodiments of Formula (VI), $R^4$, $R^5$, $R^6$, and $R^7$ are independently selected from hydrogen and halogen. In some embodiments of Formula (VI), $R^4$, $R^5$, $R^6$, and $R^7$ are hydrogen.

In some embodiments of Formula (VI), $R^8$, $R^{10}$, and $R^{11}$ are independently selected from hydrogen, halogen, —$(CH_2)_x$—C(O)—$OC_{1-6}$ alkyl, —$OCH_2C_6H_5$, —$OCOCH_3$, —$(CH_2)_x$—$CONH_2$, —CHO, —$(CH_2)_x$—COOH, —$(CH_2)_x$—$COC_{1-6}$ alkyl, phenyl, and substituted phenyl; wherein the substituted phenyl is substituted with 1-4 substituents selected from hydroxyl, $C_{1-6}$alkoxy, and $C_{1-6}$alkyl. In some embodiments, $R^8$, $R^{10}$, and $R^{11}$ are independently selected from hydrogen, halogen, —CHO, —$(CH_2)_x$—COOH, —$(CH_2)_x$—$COOC_{1-6}$ alkyl, phenyl, and substituted phenyl; wherein the substituted phenyl is substituted with 1-4 substituents selected from hydroxyl, $C_{1-6}$alkoxy, and $C_{1-6}$alkyl.

Compounds and Compositions

In some embodiments, the present disclosure provides a compound and pharmaceutically acceptable salts thereof and compositions comprising a compound and pharmaceutically acceptable salts thereof for use in the present methods, wherein the compound is selected from the following:

TABLE 1

| Compound | Structure | Chemical Name |
|---|---|---|
| 1 | ![structure] | 1H-indole-3-carbaldehyde |

TABLE 1-continued

| Compound | Structure | Chemical Name |
|---|---|---|
| 2 | 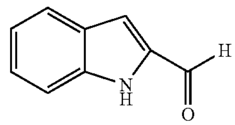 [SMILES: O=Cc1cc2ccccc2[nH]1] | 1H-indole-2-carbaldehyde |
| 3 | 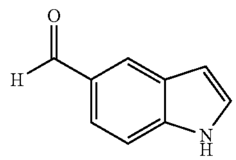 [SMILES: O=Cc1ccc2[nH]ccc2c1] | 1H-indole-5-carbaldehyde |
| 4 | 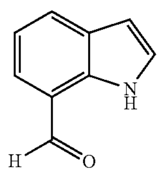 | 1H-indole-7-carbaldehyde |
| 5 | 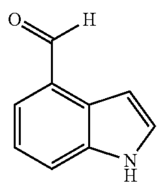 [SMILES: O=Cc1cccc2[nH]ccc12] | 1H-indole-4-carbaldehyde |
| 6 | 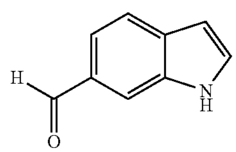 [SMILES: O=Cc1ccc2cc[nH]c2c1] | 1H-indole-6-carbaldehyde |
| 7 | 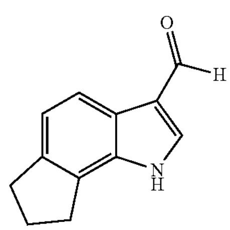 [SMILES: O=Cc1c[nH]c2c3c(ccc12)CCC3] | 1,6,7,8-tetrahydrocyclopenta[g]indole-3-carbaldehyde |
| 8 | 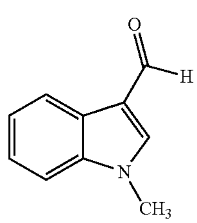 | 1-methyl-1H-indole-3-carbaldehyde |
| 9 | 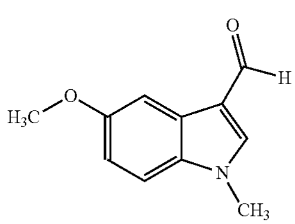 | 5-methoxy-1-methyl-1H-indole-3-carbaldehyde |

TABLE 1-continued
| Compound | Structure | Chemical Name |
|---|---|---|
| 10 | 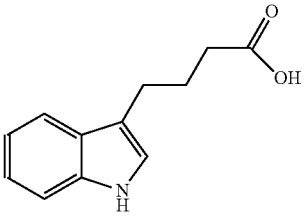 [SMILES: O=C(O)CCCc1c[nH]c2ccccc12] | 4-(1H-indol-3-yl)butanoic acid |
| 11 | 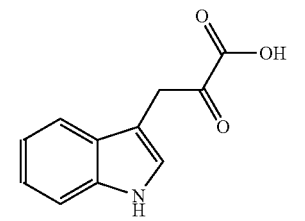 [SMILES: O=C(O)C(=O)Cc1c[nH]c2ccccc12] | 3-(1H-indol-3-yl)-2-oxopropanoic acid |
| 12 | 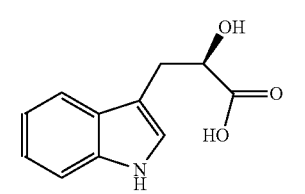 [SMILES: O=C(O)[C@H](O)Cc1c[nH]c2ccccc12] | (R)-2-hydroxy-3-(1H-indol-3-yl)propanoic acid |
| 13 | 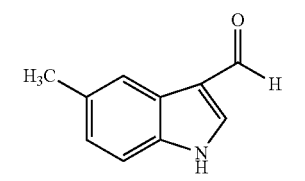 | 5-methyl-1H-indole-3-carbaldehyde |
| 14 | 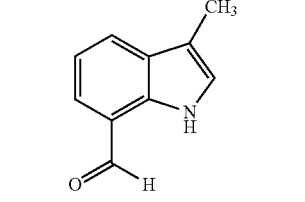 | 3-methyl-1H-indole-7-carbaldehyde |
| 15 | 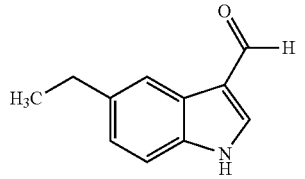 | 5-ethyl-1H-indole-3-carbaldehyde |
| 16 | 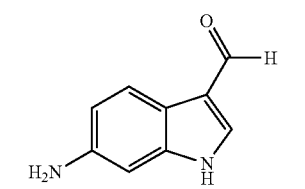 [SMILES: Nc1ccc2c(C=O)c[nH]c2c1] | 6-amino-1H-indole-3-carbaldehyde |

TABLE 1-continued

| Compound | Structure | Chemical Name |
|---|---|---|
| 17 | 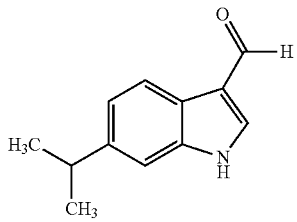 | 6-isopropyl-1H-indole-3-carbaldehyde |
| 18 | 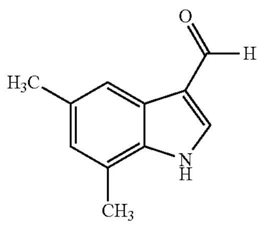 | 5,7-dimethyl-1H-indole-3-carbaldehyde |
| 19 | 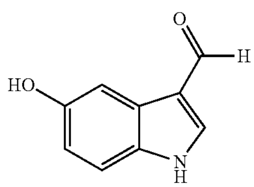 [SMILES: O=Cc1c[nH]c2ccc(O)cc12] | 5-hydroxy-1H-indole-3-carbaldehyde |
| 20 | 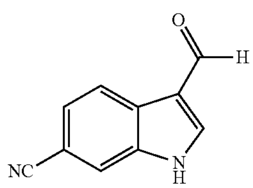 [SMILES: N#Cc1ccc2c(C=O)c[nH]c2c1] | 3-formyl-1H-indole-6-carbonitrile |
| 21 | 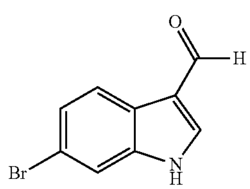 [SMILES: O=Cc1c[nH]c2cc(Cl)ccc12] | 6-bromo-1H-indole-3-carbaldehyde |
| 22 | 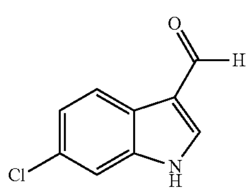 | 6-chloro-1H-indole-3-carbaldehyde |
| 23 | 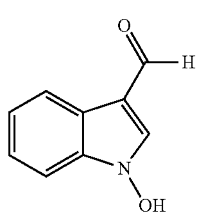 [SMILES: O=Cc1cn(O)c2ccccc12] | 1-hydroxy-1H-indole-3-carbaldehyde |

TABLE 1-continued

| Compound | Structure | Chemical Name |
|---|---|---|
| 24 | 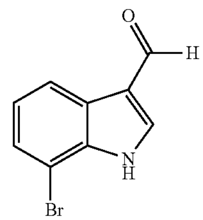 [SMILES: O=Cc1c[nH]c2c(Br)cccc12] | 7-bromo-1H-indole-3-carbaldehyde |
| 25 | 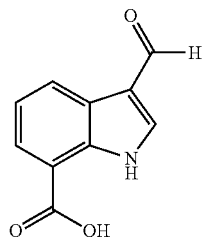 [SMILES: O=Cc1c[nH]c2c(C(=O)O)cccc12] | 3-formyl-1H-indole-7-carboxylic acid |
| 26 | 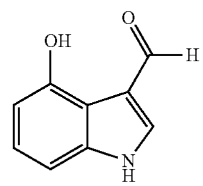 [SMILES: O=Cc1c[nH]c2cccc(O)c12] | 4-hydroxy-1H-indole-3-carbaldehyde |
| 27 | 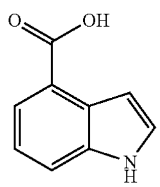 [SMILES: O=C(O)c1cccc2[nH]ccc12] | 1H-indole-4-carboxylic acid |
| 28 | 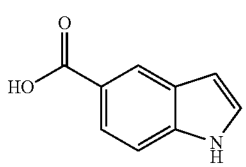 [SMILES: O=C(O)c1ccc2[nH]ccc2c1] | 1H-indole-5-carboxylic acid |
| 29 | 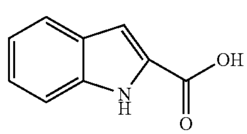 [SMILES: O=C(O)c1cc2ccccc2[nH]1] | 1H-indole-2-carboxylic acid |
| 30 | 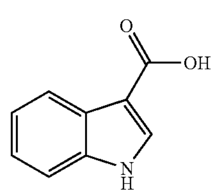 [SMILES: O=C(O)c1c[nH]c2ccccc12] | 1H-indole-3-carboxylic acid |
| 31 | 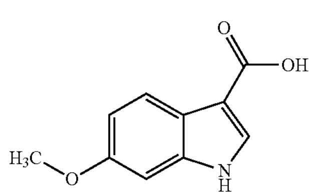 | 6-methoxy-1H-indole-3-carboxylic acid |

TABLE 1-continued

| Compound | Structure | Chemical Name |
|---|---|---|
| 32 | 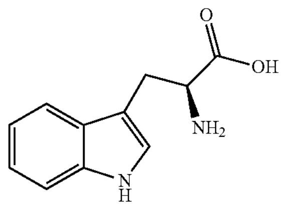 [SMILES: N[C@@H](Cc1c[nH]c2ccccc12)C(=O)O] | (S)-2-amino-3-(1H-indol-3-yl)propanoic acid; L-tryptophan |
| 33 | 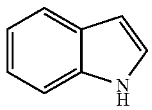 | 1H-indole |
| 34 | 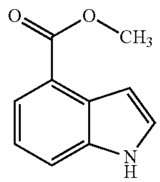 | methyl 1H-indole-4-carboxylate |
| 35 | 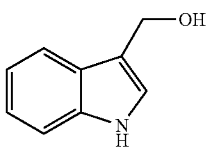 [SMILES: OCc1c[nH]c2ccccc12] | (1H-indol-3-yl)methanol |
| 36 | 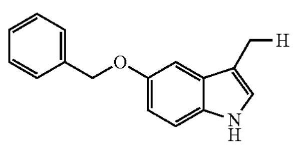 [SMILES: Cc1c[nH]c2ccc(OCc3ccccc3)cc12] | 5-(benzyloxy)-1H-indole-3-carbaldehyde |
| 37 | 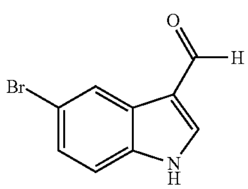 [SMILES: O=Cc1c[nH]c2ccc(Br)cc12] | 5-bromo-1H-indole-3-carbaldehyde |
| 38 | 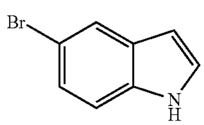 | 5-bromo-1H-indole |
| 39 | 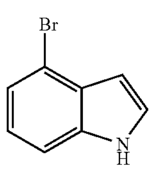 | 4-bromo-1H-indole |
| 40 | 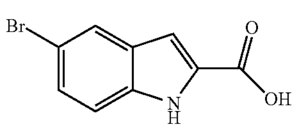 [SMILES: O=C(O)c1cc2cc(Br)ccc2[nH]1] | 5-bromo-1H-indole-2-carboxylic acid |
| 41 | 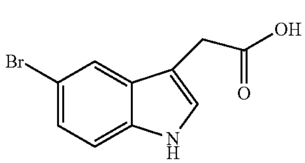 [SMILES: O=C(O)Cc1c[nH]c2ccc(Br)cc12] | 2-(5-bromo-1H-indol-3-yl)acetic acid |

TABLE 1-continued

| Compound | Structure | Chemical Name |
|---|---|---|
| 42 | 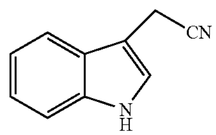 [SMILES: N#CCc1c[nH]c2ccccc12] | 2-(1H-indol-3-yl)acetonitrile |
| 43 | 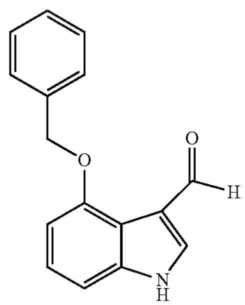 [SMILES: O=Cc1c[nH]c2cccc(OCc3ccccc3)c12] | 4-(benzyloxy)-1H-indole-3-carbaldehyde |
| 44 | 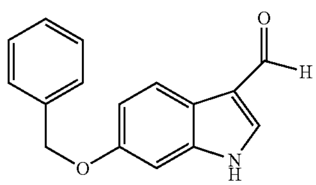 [SMILES: O=Cc1c[nH]c2cc(OCc3ccccc3)ccc12] | 6-(benzyloxy)-1H-indole-3-carbaldehyde |
| 45 | 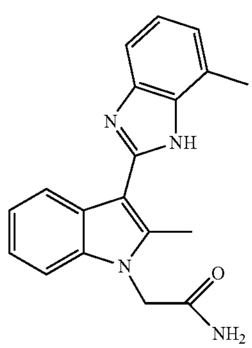 [SMILES: Cc1cccc2nc(-c3c(C)n(CC(N)=O)c4ccccc34)[nH]c12] | 2-(2-methyl-3-(7-methyl-1H-benzo[d]imidazol-2-yl)-1H-indol-1-yl)acetamide |
| 46 | 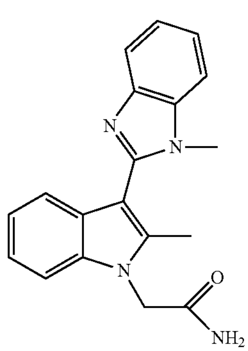 [SMILES: Cc1c(-c2nc3ccccc3n2C)c2ccccc2n1CC(N)=O] | 2-(2-methyl-3-(1-methyl-1H-benzo[d]imidazol-2-yl)-1H-indol-1-yl)acetamide |

TABLE 1-continued

| Compound | Structure | Chemical Name |
|---|---|---|
| 47 | 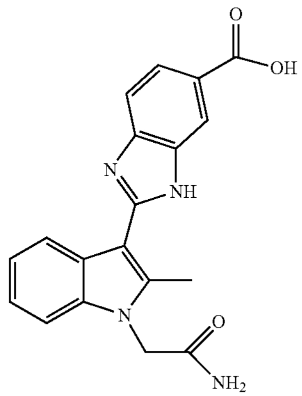 [SMILES: Cc1c(-c2nc3ccc(C(=O)O)cc3[nH]2)c2ccccc2n1CC(N)=O] | 2-(1-(2-amino-2-oxoethyl)-2-methyl-1H-indol-3-yl)-1H-benzo[d]imidazole-6-carboxylic acid |
| 48 | 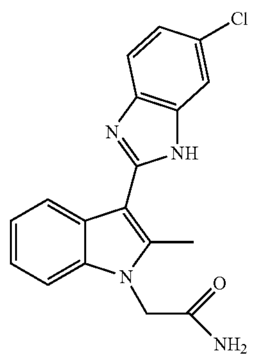 [SMILES: Cc1c(-c2nc3ccc(Cl)cc3[nH]2)c2ccccc2n1CC(N)=O] | 2-(3-(6-chloro-1H-benzo[d]imidazol-2-yl)-2-methyl-1H-indol-1-yl)acetamide |
| 49 | 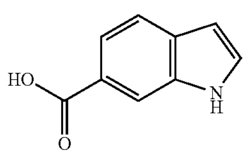 [SMILES: O=C(O)c1ccc2cc[nH]c2c1] | Indole-6-carboxylic acid |
| 50 | 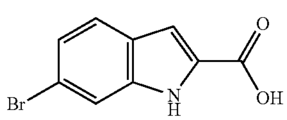 [SMILES: O=C(O)c1cc2ccc(Br)cc2[nH]1] | 6-bromoindole-2-carboxylic acid |
| 51 | 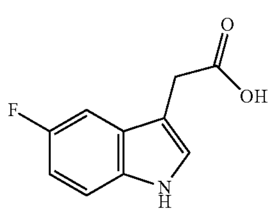 [SMILES: O=C(O)Cc1c[nH]c2ccc(F)cc12] | 5-fluoroindole-3-acetic acid |
| 52 | 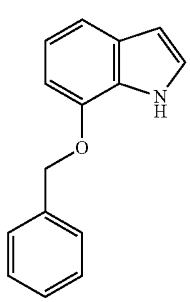 [SMILES: c1ccc(COc2cccc3cc[nH]c23)cc1] | 7-benzyloxyindole |

TABLE 1-continued
| Compound | Structure | Chemical Name |
|---|---|---|
| 53 | 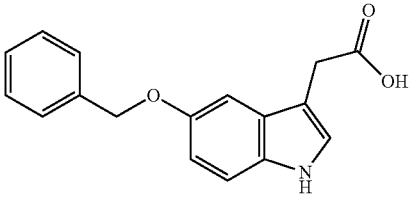 [SMILES: O=C(O)Cc1c[nH]c2ccc(OCc3ccccc3)cc12] | 5-benzyloxyindole-3-acetic acid |
| 54 | 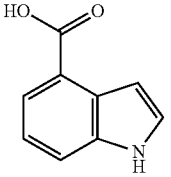 [SMILES: O=C(O)c1cccc2[nH]ccc12] | Indole-4-carboxylic acid |
| 55 | 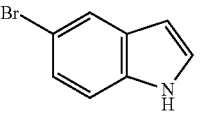 | 6-bromoindole |
| 56 | 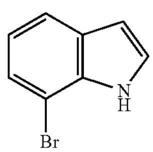 | 7-bromoindole |
| 57 | 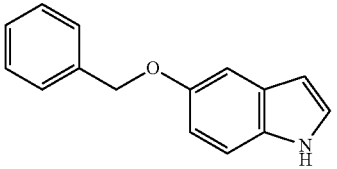 [SMILES: c1ccc(COc2ccc3[nH]ccc3c2)cc1] | 5-benzyloxyindole |
| 58 | 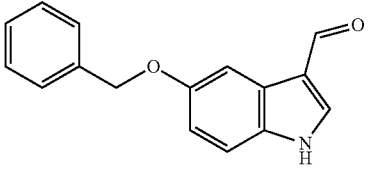 [SMILES: O=Cc1c[nH]c2ccc(OCc3ccccc3)cc12] | 5-benzyloxyindole-3-carboxaldehyde |
| 59 | 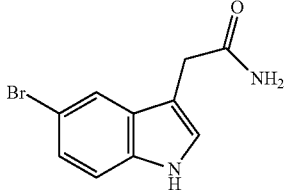 [SMILES: NC(=O)Cc1c[nH]c2ccc(Br)cc12] | 5-bromoindole-3-acetamide |
| 60 | 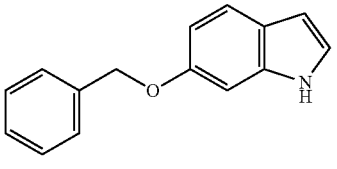 [SMILES: c1ccc(COc2ccc3cc[nH]c3c2)cc1] | 6-benzyloxyindole |

TABLE 1-continued

| Compound | Structure | Chemical Name |
|---|---|---|
| 61 | 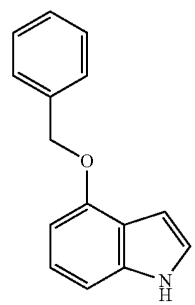 [SMILES: c1ccc(COc2cccc3[nH]ccc23)cc1] | 4-benzyloxyindole |
| 62 | 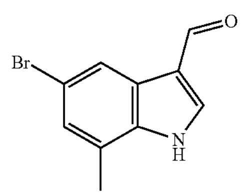 | 5-bromo-7-methylindole-3-carboxyaldehyde |
| 63 | 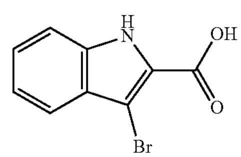 [SMILES: O=C(O)c1[nH]c2ccccc2c1Br] | 3-bromoindole-2-carboxylic acid |
| 64 | 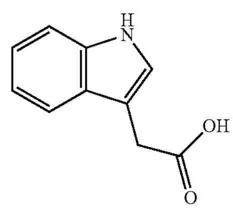 [SMILES: O=C(O)Cc1c[nH]c2ccccc12] | Indole-3-acetic acid |
| 65 | 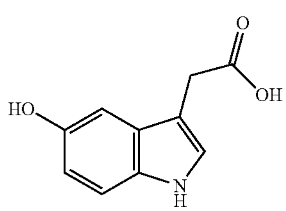 [SMILES: O=C(O)Cc1c[nH]c2ccc(O)cc12] | 5-hydroxyindole-3-acetic acid |
| 66 | 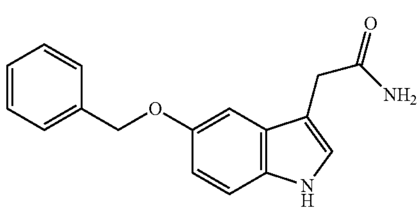 [SMILES: NC(=O)Cc1c[nH]c2ccc(OCc3ccccc3)cc12] | 5-benzyloxyindole-3-acetamide |
| 67 | 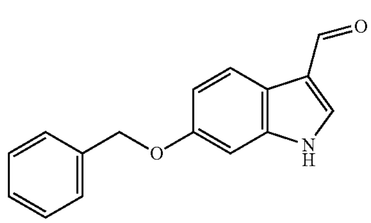 [SMILES: O=Cc1c[nH]c2cc(OCc3ccccc3)ccc12] | 6-benzyloxyindole-3-carboxaldehyde |

TABLE 1-continued

| Compound | Structure | Chemical Name |
|---|---|---|
| 68 | 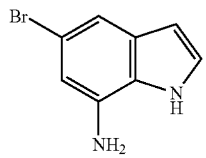 [SMILES: Nc1cc(Br)cc2cc[nH]c12] | 7-amino-5-bromoindole |
| 69 | 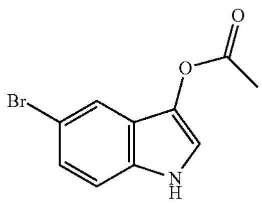 | 5-bromoindoxyl acetate; 3-Acetoxy-5-bromoindole |
| 71 | 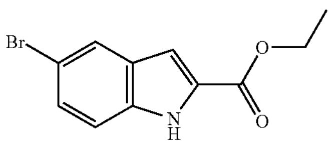 | Ethyl 5-bromoindole-2-carboxylate |
| 73 | 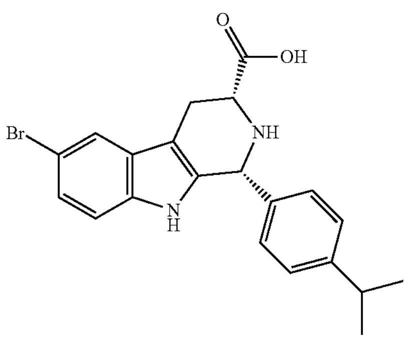 [SMILES: CC(C)c1ccc([C@H]2N[C@@H](C(=O)O)Cc3c2[nH]c2ccc(Br)cc32)cc1] | (1R,3R)-6-bromo-1-(4-isopropylphenyl)-2,3,4,9-tetrahydro-1H-pyrido[3,4-b]indole-3-carboxylic acid |
| 74 | 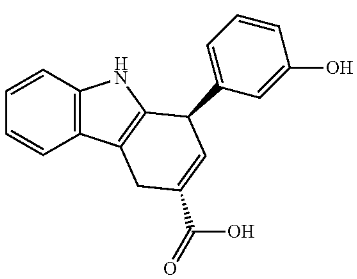 | (1R,3S)-1-(3-hydroxyphenyl)-2,3,4,9-tetrahydro-1H-pyrido[3,4-b]indole-3-carboxylic acid |
| 75 | 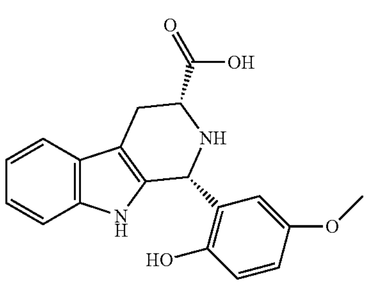 [SMILES: COc1ccc(O)c([C@H]2N[C@@H](C(=O)O)Cc3c2[nH]c2ccccc32)c1] | (1R,3R)-1-(2-hydroxy-5-methoxyphenyl)-2,3,4,9-tetrahydro-1H-pyrido[3,4-b]indole-3-carboxylic acid |

TABLE 1-continued

| Compound | Structure | Chemical Name |
|---|---|---|
| 76 | 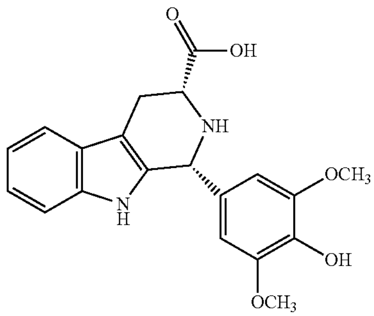 [SMILES: COc1cc([C@H]2N[C@@H](C(=O)O)Cc3c2[nH]c2ccccc32)cc(OC)c1O] | (1R,3R)-1-(4-hydroxy-3,5-dimethoxyphenyl)-2,3,4,9-tetrahydro-1H-pyrido[3,4-b]indole-3-carboxylic acid |
| 77 | 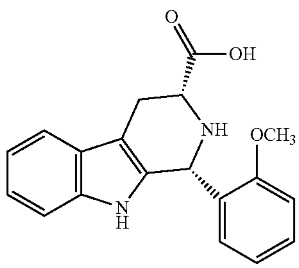 [SMILES: COc1ccccc1[C@H]1N[C@@H](C(=O)O)Cc2c1[nH]c1ccccc21] | (1R,3R)-1-(2-methoxyphenyl)-2,3,4,9-tetrahydro-1H-pyrido[3,4-b]indole-3-carboxylic acid |
| 78 | 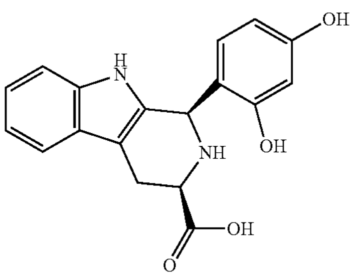 [SMILES: O=C(O)[C@H]1Cc2c([nH]c3ccccc23)[C@@H](c2ccc(O)cc2O)N1] | (1R,3R)-1-(2,4-dihydroxyphenyl)-2,3,4,9-tetrahydro-1H-pyrido[3,4-b]indole-3-carboxylic acid |
| 79 | 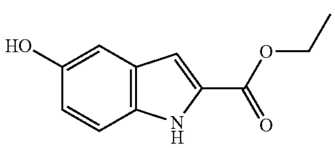 | Ethyl-5-hydroxy-1H-indole-2-carboxylate |
| 80 | 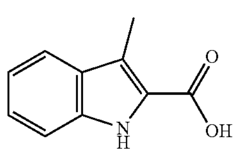 | 3-methyl-1H-indole-2-carboxylic acid |
| 81 | 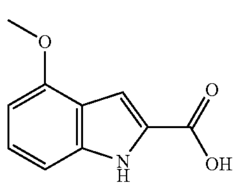 | 4-methoxy-1H-indole-2-carboxylic acid |

In some embodiments, the present disclosure provides Compounds 2, 10, 29, 38, 40, 41, 43, and 44 and pharmaceutically acceptable salts thereof for use in the present methods.

| Compound | Structure | Chemical Name |
|---|---|---|
| 2 | 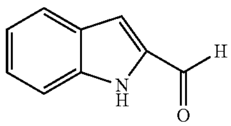 | 1H-indole-2-carbaldehyde |
| 10 | 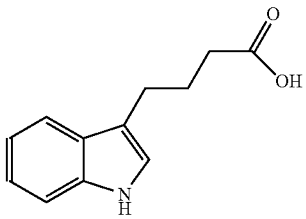 [SMILES: O=C(O)CCCc1c[nH]c2ccccc12] | 4-(1H-indol-3-yl)butanoic acid |
| 29 | 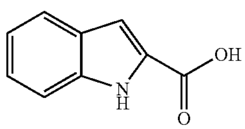 [SMILES: O=C(O)c1cc2ccccc2[nH]1] | 1H-indole-2-carboxylic acid |
| 38 | 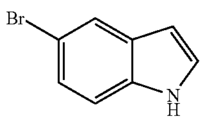 | 5-bromo-1H-indole |
| 40 | 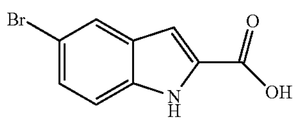 [SMILES: O=C(O)c1cc2cc(Br)ccc2[nH]1] | 5-bromo-1H-indole-2-carboxylic acid |
| 41 | 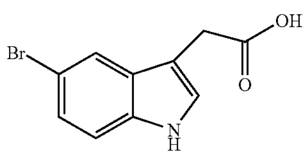 | 2-(5-bromo-1H-indol-3-yl)acetic acid |
| 43 | 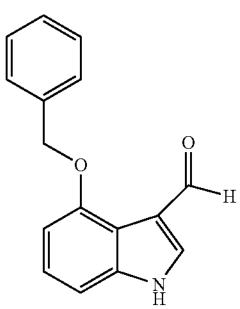 [SMILES: O=Cc1c[nH]c2cccc(OCc3ccccc3)c12] | 4-(benzyloxy)-1H-indole-3-carbaldehyde |
| 44 | 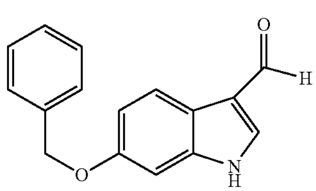 [SMILES: O=Cc1c[nH]c2cc(OCc3ccccc3)ccc12] | 6-(benzyloxy)-1H-indole-3-carbaldehyde |

In some embodiments, the indole compound is apoptotic. In some embodiments, the indole compound is cytolytic. In some embodiments, the indole compound is pyroptotic. Such properties can be determined, for example, through histology with fresh ex-vivo fat tissues. The presence of cell wall lysis, "ghosting," and loss of integrity of regions of confluent adipocytes can indicate that an indole compound has activity against adipocytes. Signs of apoptosis, histologically, include "ghosting" and regions of shrinking or much smaller cells. Signs of cytolysis include disruption of cell walls, and with aggressive compositions and the detergent controls, large "moth-eaten" regions where no cells exist; they have all been lysed. Signs of pyroptosis include a combination of both findings. In a live animal or human, cytolysis can produce inflammatory changes.

In some embodiments, the indole compounds are inflammatory. In some embodiments, the indole compounds are non-inflammatory. In some embodiments, the indole compounds are moderately inflammatory. Depending on the mechanism of action, the level of inflammation induced by indole compounds varies. Inflammatory response is generated when the cell wall is mechanically lysed or the cell dies an ischemic death. Release of the cell contents and lysozymes triggers significant local swelling, and a cytokine and histamine response. An early indicator is the presence of neutrophils or lymphocytes in the affected target tissue. With an aggressive composition, large areas of viable cells are missing, and the region is filled with ground substance. Fibrosis is indicated by thickening of the fibrous septae. Macrophages infiltrate, and "crown-like" structures-noted by the presence of macrophages at the verge of an adipocyte cell wall—are also hallmarks of fatty inflammation. Cytolytic indoles can generate an inflammatory response. Apoptosis is noninflammatory. There are no macrophages, nor is there an apoptotic target. Apoptosis occurs when the cell is programmed to die. The cell shrinks and "ghosting— the residual intact cell wall without much cytoplasm—can be seen.

In some embodiments, the indole compound is at least about 25% (such as at least about any of 30%, 40%, 50%, 60%, 70%, 80%, 90%, or 100%) more specific to adipocytes than to muscle cells (such as skeletal muscle cells). In some embodiments, the indole compound is at least about 80% more specific to adipocytes than to muscle cells (such as skeletal muscle cells). In some embodiments, the indole compound is at least about 2×, 3×, or 4× more specific to adipocytes than to muscle cells (such as skeletal muscle cells).

In some embodiments, the indole compound is at least about 25% (such as at least about any of 30%, 40%, 50%, 60%, 70%, 80%, 90%, or 100%) more specific to adipocytes than to nerve cells (such as peripheral nerve cells). In some embodiments, the indole compound is at least about 80% more specific to adipocytes than to nerve cells (such as peripheral nerve cells). In some embodiments, the indole compound is at least about 2×, 3×, or 4× more specific to adipocytes than to nerve cells (such as peripheral nerve cells).

In some embodiments, the indole compound is at least about 25% (such as at least about any of 30%, 40%, 50%, 60%, 70%, 80%, 90%, or 100%) more specific to adipocytes than to dermal cells (such as dermal fibroblasts). In some embodiments, the indole compound is at least about 80% more specific to adipocytes than to dermal cells (such as dermal fibroblasts). In some embodiments, the indole compound is at least about 2×, 3×, or 4× more specific to adipocytes than to dermal cells (such as dermal fibroblasts).

In some embodiments, the indole compound is selected from the group consisting of Compounds 2 and 43. In some embodiments, the indole compound has a cell killing activity and tissue specificity that are at least as high as those of an indole compound selected from the group consisting of Compounds 2 and 43.

In some embodiments, the indole compound is selected from the group consisting of Compounds 40 and 41. In some embodiments, the indole compound has a cell killing activity and tissue specificity that are at most as high as those of an indole compound selected from the group consisting of Compounds 40 and 41.

In some embodiments, the indole compound is selected from the group consisting of Compounds 10 and 29. In some embodiments, the indole compound has a cell killing activity and tissue specificity that are at least as high as those of an indole compound selected from the group consisting of Compounds 27 and 28.

In some embodiments, the indole compound is a compound having a cell killing activity that is between the cell killing activity of Compounds 2 or 43 and Compounds 10 or 29. In some embodiments, the indole compound is a compound having a cell killing activity that is between the cell killing activity of Compounds 10 or 29 and Compounds 40 and 41. In some embodiments, the indole compound is a compound having a cell killing activity that is between the cell killing activity of Compounds 2 or 43 and Compounds 40 or 41.

Also provided herein are methods of selecting an indole compound for any of the therapeutic methods described herein comprising assessing the activity, tissue specificity, and/or cell killing mechanism (apoptotic, cytolytic, pyroptotic, etc.) of the compound. In some embodiments, there is provided a method of determining whether an indole compound is suitable for any of the therapeutic methods described herein comprising assessing the activity, tissue specificity, and/or cell killing mechanism (apoptotic, cytolytic, pyroptotic, etc.) of the compound. In some embodiments, the compound is selected (or deemed suitable for use) if the compound has high activity against adipocytes and high tissue specificity. In some embodiments, the compound is selected (or deemed suitable for use) if the compound has high activity against adipocytes and moderate tissue specificity. In some embodiments, the compound is selected (or deemed suitable for use) if the compound has moderate activity against adipocytes and high tissue specificity. In some embodiments, the compound is selected (or deemed suitable for use) if the compound is apoptotic. In some embodiments, the compound is selected (or deemed suitable for use if the compound is cytolytic. In some embodiments, the compound is selected (or deemed suitable for use) if the compound is pyroptotic.

Pharmaceutical Formulations

The disclosed pharmaceutical compositions can be formulated as a pharmaceutically acceptable salt of a disclosed compound. Pharmaceutically acceptable salts are non-toxic salts of a free base form of a compound that possesses the desired pharmacological activity of the free base. These salts may be derived from inorganic or organic acids. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

The compositions can be formulated for various types of delivery e.g., topical, subcutaneous, subdermal, intralesional, or hypodermal, etc. by any means known in the art. Such formulations can be in the form of a tablet, powder, gel, solution, cream, vapor, ointment, etc. In some embodiments, an indole compound is formulated into a solution. In some embodiments, such solution is aqueous. The term "aqueous" as used herein refers to a solution which is a homogenous mixture prepared by dissolving a solid or a liquid in water such that the molecules of the solute or dissolved substance are dispersed among those of water.

Pharmacologically acceptable aqueous vehicles for the compositions of the present invention can include, for example, any liquid solution that is capable of dissolving an indole compound and is not toxic to the particular individual receiving the formulation. Examples of pharmaceutically acceptable aqueous vehicles include, without limitation, saline, water and acetic acid. Typically, pharmaceutically acceptable aqueous vehicles are sterile. In some embodiments, the indole compound is in an aqueous solution buffered at a pH of between about 8.0 and about 8.5.

In some embodiments, compositions are formulated for veterinary applications with one or more veterinary excipients. In some embodiments, compositions are formulated for cosmetic applications with one or more cosmetic excipients. For delivery into humans, the compositions are formulated with one or more pharmaceutical excipients.

A "pharmaceutically acceptable excipient" or "pharmaceutical excipient" may be used herein, and refers to a compound that is useful in preparing a pharmaceutical composition that is generally safe, non-toxic and neither biologically nor otherwise undesirable, and includes excipients that are acceptable for veterinary use or human pharmaceutical use. A pharmaceutically acceptable excipient as used herein includes both one and more than one such excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, phosphatidylcholine, cellulose, sterile water, syrup, and methyl cellulose. The formulations can additionally include: lubricating agents such as talc, magnesium stearate, and mineral oil; wetting agents; emulsifying and suspending agents; and preserving agents such as methyl- and propylhydroxy-benzoates and benzyl alcohol. In some embodiments, suitable excipients include cyclodextrins (such as hydroxypropyl-cyclodextrin and sulfobutylether-cyclodextrin), polyethylene glycol, polyethylene glycol-400 (PEG-400), Tween 80, ethanol, and DMSO. The compositions of the present invention can be formulated so as to provide quick, sustained or delayed release of the indole compound after administration to the subject by employing procedures known in the art.

Additional excipients suitable for formulation with an indole compound include penetration enhancers and dispersion agents. Non-limiting examples of dispersion agents which allow the dispersion of drugs in tissue include hyaluronidase and collagenase. Hyaluronidase functions to augment tissue permeability and spread or dispersion of other drugs. Collagenase has been used to isolate adipocytes from subcutaneous fat and does not have lytic effects on adipocytes themselves. Additionally hyaluronidase and collagenase can facilitate healing by accelerating reduction of necrotic tissue after treatment with the indole compound formulations of the present invention.

In some embodiments, a formulation comprising an indole compound is administered by injection, for example, by bolus injection. In some embodiments, the formulation can have direct contact with the fat tissue. The formulation can be injected subcutaneously or infused directly into the fat. In some embodiments, the formulation can have direct contact with the skin tissue for skin and soft tissue tightening. The formulation can be injected or infused directly into the skin tissue. Formulations for injection can be presented in unit dosage form, for example, in ampoules or in multi-dose containers, with or without an added preservative. The compositions can take such forms as suspensions, solutions, or emulsions in oily or aqueous vehicles, and can contain formulatory agents such as suspending, stabilizing and/or dispersing agents.

Unit Dose

A unit dose comprises an amount of a compound of an indole compound. In some embodiments, the indole compound is a compound of Formula (I). As an injectable solution, a unit dose has an amount of an indole compound in a volume of solution.

In some embodiments, a unit dose comprises of more than 0.1% w/w, w/v or v/v of an indole compound and the unit dose has a total volume of more than 0.2 ml and less than 500 ml. In some embodiments, a unit dose comprises of more than 0.1% w/w, w/v or v/v of an indole compound and the unit dose has a total volume of more than 0.1 ml and less that 0.2 ml. In some embodiments, a unit dose comprises of more than 0.1% w/w, w/v or v/v of an indole compound and the unit dose has a total volume of less than 0.1 ml.

The dose can depend on the following factors—the amount of fat present, the desired effect, and the concentration of the drug. In some embodiments, a solution for injection comprises about 1-20 mg/ml of an indole compound. In some embodiments, a solution for injection comprises about 1-5, 6-10, 11-15, or 16-20 mg/ml of an indole compound. In some embodiments, a solution for injection comprises about 8-12 or 10 mg/ml of an indole compound.

In some embodiments, unit doses are in a container or a syringe. Such unit doses can have, for example, a total volume of up to 100, 90, 80, 70, 60, 50, 40, 30, 20, 10, 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002, or 0.0001 ml. In some embodiments, a unit dose has a total volume in the range of 0.0001-100, 0.0005-90, 0.001-80, 0.005-70, 0.01-60, 0.05-50, 0.06-40, 0.07-30, 0.08-20, 0.09-10, or 0.1-5 ml. Other embodiments contemplate a unit dose with a total volume in the range of 0.01-2, 0.05-1 or 0.1-0.5 ml total volume. In some embodiments, a unit dose has a total volume greater 0.0001, 0.0002, 0.0005, 0.001, 0.002, 0.005, 0.01, 0.02, 0.05, 0.1, 0.2, 0.5, 1, 2, 5, 10, 20, 50, 100 ml. In some embodiments, a unit dose has a total volume of up to 1.0, 0.9. 0.8, 0.7, 0.6, 0.5, 0.4, 0.3, 0.2, 0.1, 0.05, or 0.01 ml.

In some embodiments, a unit dose includes up to 10, 9, 8, 7, 6, 5, 4, 3, 2, 1, 0.9, 0.8, 0.7, 0.6, 0.5, 0.4, 0.3, 0.2, 0.1, 0.09, 0.08, 0.07, 0.06, 0.05, 0.04, 0.03, 0.02, 0.01, 0.009, 0.008, 0.007, 0.006, 0.005, 0.004, 0.003, 0.002, 0.001, 0.0009, 0.0008, 0.0007, 0.0006, 0.0005, 0.0004, 0.0003, 0.0002, or 0.0001 grams of an indole compound. In some embodiments, a unit dose includes a range of approximately 0.00001 to 20, 0.00005 to 15, 0.0001 to 12.5, 0.0005 to 10, 0.001 to 7.5, or 0.005 to 5 grams. In some embodiments, a unit dose comprises about 0.01, 0.1, 1, or 2 grams of an indole compound.

Second Therapeutic Agents

The present disclosure provides compositions that can be co-formulated, co-administered, and/or co-marketed with a second therapeutic agent. In some embodiments, the second therapeutic agent is co-formulated with an indole compound and administered simultaneously with the indole compound. In some embodiments, the second therapeutic agent is administered prior to or after the administration of an indole compound. The second therapeutic agent can be administered locally, regionally, or systemically.

In some embodiments, the second therapeutic agent is a detergent, a bile acid, bile salt, deoxycholic acid or a salt thereof. In some embodiments, the second therapeutic agent is phosphatidylcholine or deoxycholate or mixtures thereof. These compositions are described in US 2005/0267080, WO 2008/066775 and US 2009/0233885, which are herein incorporated by reference in their entireties.

Non-limiting examples of second therapeutic agents include: anesthetics, anti-microbial agents, vasoconstrictors, anti-thrombotic agents, anti-coagulation agents, anti-inflammatory agents, analgesics, dispersion agents, anti-dispersion agents, penetration enhancers, steroids, tranquilizers, muscle relaxants, anti-diarrhea agents, beta adrenergic stimulators, and collagenase.

In some embodiments, the compositions can further comprise an amount of beta adrenergic stimulator. A beta adrenergic stimulator can bind either directly or indirectly to the beta-receptor, thereby stimulating it. The stimulated receptor triggers a complex series of events involving multiple enzyme systems which results in an accumulation of cyclic AMP within the cell and decreased ATP. These conditions can activate lipases which break down triglyceride fats in the adipocytes into free fatty acids, which can be used by the cell for growth and metabolism, or may be discharged extracellularly. Various beta adrenergic stimulators individually or in combination can be included in the compositions, such as isoproterenol hydrochloride (ISUPREL®), isoproterenol hydrochloride, forskolin, norepinephrine, guarana and clenbuterol, or other beta-receptor specific agonist (or nonspecific agonists such as ephedrine as to certain applications)

In some embodiments, the compositions can further comprise, individually or in various permutations or combinations, an amount of collagenase, such as Clostridial collagenase or an amount of one or more of nicotinic acid, clofibrate, tannic acid, scorpion toxin, snake venom, beta adrenic stimulants, dimethlyaminoethanol, hyaluronic acid, penta-O-galloyl-alpha-D-glucose, hormone sensitive lipase, human adipose triglyceride lipase, TNF-alpha, raspberry ketone, ethanol, rosiglitazone, peroxisome-proliferator activated receptor gamma, Y-9738 (ethyl 2(4-chlorophenyl)-5-ethoxy-4-oxazoleacetate) oliphen, fish oil, scallop shell extract, peanut shell extract, caffeine, or bee venom.

Anti-microbial agents suitable for use with the compositions, methods, and kits herein include, but not limited to, anti-bactericidal agents, anti-fungal agents, anti-viral agents or the like, and are efficacious against a broad spectrum of microbes.

Examples of anti-bacterial agents include, but not limited to, benzalkonium chloride, benzoic acid, benzoxonium chloride, benzyl alcohol, 2-bromo-2-nitropropane-1,3-diol, 5-bromo-5-nitro-1,3-dioxane, bromochlorophene, camphor benzalkonium methosulfate, captan, cetrimonium bromide, cetrimonium chloride, cetylpyridinium chloride, climbazol, chloracetamide, chlorhexidine and its salts, p-chloro-m-cresol, chlorphenesin, chloroxylenol, chlorophen, chlorobutanol, o-cymen-5-ol, dehydroacetic acid, dibromodicyanobutan, dibromohexamidin, dibromopropamidin, dichlorobenzyl alcohol, dichlorophenyl imidazoldioxolan, dimethyloxazolidin, DMDM hydantoin, dodecylguanidine acetate, hexamidine diisothionate, hexachlorophen, hexetidin, iodopropynyl butylcarbamate, lauryl isoquinolinium bromide, methyldibromo glutaronitrile, methylolchloracetamide, phenethyl alcohol, phenoxyethanol, phenoxypropanol, o-phenylphenol, piroctone olamine, polyaminopropyl biguanide, potassium sorbate, potassium undecylenoyl hydrolyzed collagen, quaternium-15, salicylic acid, sodium benzoate, sodium dehydroacetate, sodium hydroxymethylglycinate, sodium o-phenylphenate, sorbic acid, triclocarban, triclosan, undecylenic acid and its derivatives, zinc cysteate, zinc gluconate, zinc pyrithione, or zinc sulfate. Derivatives of undecylenic acid useful as anti-microbial agents are e.g. esters, such as methyl ester, isopropyl ester, glyceryl ester, ethoxylated soya sterol ester, or ethoxylated PHB ester, or amides, such as monoethanolamide, monoethanolamide derivatives such as monoethanolamide (MEA) sulfosuccinate salts, diethanolamide, protein condensates, e.g. potassium undecylenoyl hydrolyzed animal collagen, and quaternized 3-aminopropyl-amide, e.g. undecylenamidopropyltrimonium methosulfate. Specific examples of suitable fungicidal/fungistatic agents include, without limitation, dithiocarbamates, phthalimides, dicarboximides, organophosphates, benzimidazoles, carboxanilides, phenylamides, phosphites, and the like.

Other examples of anti-bacterial agents include, but are not limited to, erythromycin, clarithromycin, penicillins, cephalosporins, aminoglycosides, sulfonamides, macrolides, tetracyclins, lincosides, quinolones, chloramphenicol, vancomycin, metronidazole, rifampin, isoniazid, spectinomycin, trimethoprim, sulfamethoxazole, penems, carbapenems, monobactams mupirocin, neomycin sulfate bacitracin, polymyxin B, 1-ofloxacin, tetracyclines (chlortetracycline hydrochloride, oxytetracycline hydrochloride and tetrachcycline hydrochoride), clindamycin phsphate, gentamicin sulfate, benzalkonium chloride, benzethonium chloride, hexylresorcinol, methylbenzethonium chloride, phenol, quaternary ammonium compounds, triclocarbon, triclosan, tea tree oil, and their pharmaceutically acceptable salts.

Other examples of anti-bacterial agents include, but are not limited to, Acrofloxacin, Amoxicillin plus clavulonic acid (i.e. Augmentin), Amikacin, Amplicillin, Apalcillin, Apramycin, Astromicin, Arbekacin, Aspoxicillin, Azidozillin, Azithromycin, Aziocillin, Bacitracin, Benzathine penicillin, Benzylpenicillin, Carbencillin, Cefaclor, Cefadroxil, Cefalexin, Cefamandole, Cefaparin, Cefatrizine, Cefazolin, Cefbuperazone, Cefcapene, Cefdinir, Cefditoren, Cefepime, Cefetamet, Cefixime, Cefinetazole, Cefminox, Cefoperazone, Ceforamide, Cefotaxime, Cefotetan, Cefotiam, Cefoxitin, Cefpimizole, Cefpiramide, Cefpodoxime, Cefprozil, Cefradine, Cefroxadine, Cefsulodin, Ceftazidime, Ceftriaxone, Cefuroxime, Chlorampenicol, Chlortetracycline, Ciclacillin, Cinoxacin, Ciprofloxacin, Clarithromycin, Clemizole penicillin, Clindamycin, Cloxacillin, Daptomycin, Demeclocycline, Desquinolone, Dibekacin, Dicloxacillin, Dirithromycin, Doxycycline, Enoxacin, Epicillin, Erthromycin, Ethambutol, Fleroxacin, Flomoxef, Flucloxacillin, Flumequine, Flurithromycin, Fosfomycin, Fosmidomycin, Fusidic acid, Gatifloxacin, Gemifloxaxin, Gentamicin, Imipenem, Imipenem plus Cilistatin combination, Isepamicin, Isoniazid, Josamycin, Kanamycin, Kasugamycin, Kitasamycin, Latamoxef, Levofloxacin, Lincomycin, Linezolid, Lomefloxacin, Loracarbaf, Lymecycline, Mecillinam, Meropenem, Methacycline, Methicillin, Metronidazole, Meziocillin, Midecamycin, Minocycline, Miokamycin, Moxifloxacin, Nafcillin, Nafcillin, Nalidixic acid, Neomycin, Netilmicin, Norfloxacin, Novobiocin, Oflaxacin, Oleandomycin, Oxacillin, Oxolinic acid, Oxytetracycline, Paromycin, Pazufloxacin, Pefloxacin, Penicillin G, Penicillin V, Phenethicillin, Phenoxymethyl penicillin, Pipemidic acid, Piperacillin, Piperacillin and Tazobactam combination, Piromidic acid, Procaine penicillin, Propicillin, Pyrimethamine, Rifabutin, Rifamide, Rifampicin, Rifamycin SV, Rifapentene, Rokitamycin, Rolitetracycline, Roxithromycin, Rufloxacin, Sitafloxacin, Sparfloxacin, Spectinomycin, Spiramycin, Sulfadiazine, Sulfadoxine, Sulfamethoxazole, Sisomicin, Streptomycin, Sulfamethoxazole, Sulfisoxazole, Synercid (Quinupristan-Dalfopristan combination), Teicoplanin, Telithromycin, Temocillin, Tetracycline, Tetroxoprim, Thiamphenicol, Ticarcillin, Tigecycline, Tobramycin, Tosufloxacin, Trimethoprim, Trimetrexate, Trovafloxacin, Vancomycin, and Verdamicin.

Vasoconstrictor agents suitable for use with the compositions of the present invention can include, for example, dihydroergotamine, ergotamine and methysergide, epinephrine, norepinephrine, and pharmaceutically-acceptable salts thereof.

Anti-thrombotic agents suitable for use with the compositions of the present invention can include, for example, argatroban, iloprost, lamifiban, taprostene, tirofiban, tissue plasminogen activator (natural or recombinant), tenecteplase (TNK), and lanoteplase (nPA); factor Vila inhibitors; factor Xa inhibitors; thrombin inhibitors (such as hirudin and argatroban); PAI-1 inhibitors (i.e., inactivators of tissue plasminogen activator inhibitors); alpha2-antiplasmin inhibitors; streptokinase, urokinase and prourokinase; and anisoylated plasminogen streptokinase activator complex. anti-coagulants (e.g. hirudin, heparin, etc.), plasminogen activators (e.g. t-PA, urokinase, etc.), fibrinolytic enzymes (e.g. plasmin, subtilisin, etc.), anti-platelet-aggregation agents (e.g. prostacyclin, aspirin, etc.) and the like.

Anti-coagulation agents suitable for use with the compositions of the present invention can include, for example, cilostazol (PLETAL®, Otsuka), clopidogrel (PLAVIX®, Sanofi), ticlopidine (TICLID®, Syntex), tirofiban (AGGRASTAT®, Merck), eptifibatide (INTEGRILIN®, COR Therapeutics), abciximab (REOPRO®, Eli Lilly), anagrelide (AGRYLIN®, Roberts), dipyridamole (PERSANTIN®, Boehringer Ingelheim), aspirin (ECOTR®, and others), dipyridamole/aspirin (AGGRENOX®, Boehringer Ingelheim), dalteparin (FRAGMIN®, Pharmacia), enoxaparin (LOVENOX®, Aventis), tinzaparin (INNOHE®, DuPont), heparin (various), danaparoid (ORGANON®, Organon), antithrombin III (THROMBATE®, Bayer), lepirudin (REFLUDAN®, Hoechst-Marion Roussel), argatroban (ACOVA®, SmithKlineBeecham), bivalirudin (ANGIOMAX®, Medicines Company), warfarin (COUMADIN®, DuPont) anisidione (MIRADON®, Schering), alteplase (ACTIVASE®, Genentech), reteplase (RETAVASE®, Boehringer Mannheim), tenecteplase (TNKASE®, Genentech), drotrecogin (XIGRIS®, Eli Lilly), anistreplase (EMINASE®, Roberts), streptokinase (STREPTASE®, Astra), urokinase (ABBOKINASE®, Abbott) and combinations thereof.

Examples of anti-dispersion agents include, but are not limited to, sucrose, glyercerol, and glycerin.

Steroids suitable for use with the compositions of the present invention can include, for example, betamethasone, chloroprednisone, clocortolone, cortisone, desonide, dexamethasone, desoximetasone, diflupredate, estradiol, fludrocortisone, flumethasone, flunisolide, fluocortolone, fluprednisolone, hydrocortisone, meprednisone, methylprednisolone, paramethasone, prednisolone, prednisone, pregnan-3-alpha-ol-20-one, testosterone, and triamcinolone, estradiol, estron, estriol, polyestradiol, polyestriol, dienestrol, diethylstilbestrol, dihydroergosterone, cyproterone, danazol, testosterone, progesterone, norethindrone, levonorgestrol, ethynodiol, norgestimate, gestanin, 3 ketondesogestrel, demegestone, promethoestrol, testosterone, spironolactone, and esters thereof, budesonide, rofleponide, rofleponide palmitate, ciclesonide, momethasone furoate, fluticasone propionate, tipredane, fluocinolone acetonide, flunisolide, flumethasone, dexamethasone, beclomethasone dipropionate, deflazacort, cortivazol, or cortisol and/or hydrocortisol, prednisone, fluorometholone acetate, dexamethasone sodium phosphate, suprofen, fluorometholone, and medrysone, optionally in their pure isomeric forms (where such forms exist) and in the forms of their pharmaceutically acceptable salts.

Anti-inflammatory agents suitable for use with the compositions of the present invention can include both steroidal anti-inflammatory agents and non-steroidal anti-inflammatory agents. Suitable steroidal anti-inflammatory agent can include, although are not limited to, corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amciafel, amcinafide, betamethasone and the balance of its esters, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and mixtures thereof can be used.

A second class of anti-inflammatory agents which is useful in the compositions of the present invention includes the nonsteroidal anti-inflammatory agents. A variety of compounds encompassed by this group are well-known to those skilled in the art. Suitable non-steroidal anti-inflammatory agents useful in the compositions of the present invention include, but are not limited to: the oxicams, such as piroxicam, isoxicam, tonexicam, sudoxicam, and CP-14, 304; the salicylates, such as salicylic acid, aspirin, disalcid, benorylate, trilisate, safapryn, solprin, diflunisal, and fendosal; the acetic acid derivatives, such as diclofenac, fenclofenac, indomethacin, sulindac, tolmetin, isoxepac, furofenac, tiopinac, zidometacin, acematacin, fentiazac, zomepiract, clidanac, oxepinac, and felbinac; the fenamates, such as mefenamic, meclofenamic, flufenamic, niflumic, and tolfenamic acids; the propionic acid derivates, such as ibuprofen, naproxen, benoxaprofen, flurbiprofen, ketoprofen, fenoprofen, fenbufen, indoprofen, pirprofen, carprofen, oxaprozin, pranoprofen, miroprofen, tioxaprofen, suprofen, alminoprofen, and tiaprofenic; and the pyrazoles, such as phenybutazone, oxyphenbutazone, feprazone, azapropazone, and trimethazone. Mixtures of these nonsteroidal anti-inflammatory agents can also be employed, as well as the pharmaceutically-acceptable salts and esters of these agents.

Analgesics suitable for use with the composition of the present invention to reduce discomfort due to inflammation after subcutaneous injection of the formulation of the present invention include, but are not limited to, injectable local amine and ester anesthetics. Non-limiting examples of analgesics include ropivacaine, lidocaine, mepivacaine, bupivacaine, procaine, chloroprocaine, etidocaine, prilocalne dyclonine, hexylcaine, procaine, cocaine, ketamine, pramoxine, propophol, phenol and tetracaine. Mixtures of these analgesics can also be employed, as well as the pharmaceutically acceptable salts and esters or these agents. Other examples of analgesics include opioids. Examples of opioids include morphine, or a salt thereof, such as the sulphate, chloride, or hydrochloride. Other 1,4-hydroxymorphinan opioid analgesics that may be used herein include those such as naloxone, meperidine, butorphanol or pentazocine, or morphine-6-glucuronide, codeine, dihydrocodeine, diamorphine, dextropropoxyphene, pethidine, fentanyl, alfentanil, alphaprodine, buprenorphine, dextromoramide, diphenoxylate, dipipanone, heroin (diacetylmorphine), hydrocodone (dihydrocodeinone), hydromorphone (dihydromorphinone), levorphanol, meptazinol, methadone, metopon (methyldihydromorphinone), nalbuphine, oxycodone (dihydrohydroxycodeinone-), oxymorphone (dihydrohydroxymorphinone), phenadoxone, phenazocine, remifentanil, tramadol, or a salt of any of these. The opioid used in the method of the invention may comprise any combination of the aforementioned compounds. Naloxone is also included within the definition of an opioid. In certain embodiments, the analgesic is hydromorphone, oxycodone, or morphine, e.g. morphine sulphate and fentanyl and/or pharmaceutically-acceptable salts thereof.

Suitable tranquilizer and sedative drugs that may included in the kits or compositions of the present invention include chlordiazepoxide, benactyzine, benzquinamide, flurazepam, hydroxyzine, loxapine, promazine, and/or acceptable salts and esters thereof.

Suitable muscle relaxant drugs that may be included in the kits or compositions of the present invention include cinnamedrine, cyclobenzaprine, flavoxate, orphenadrine, papaverine, mebeverine, idaverine, ritodrine, dephenoxylate, dantrolene, azumolene, and/or pharmaceutically-acceptable salts thereof.

Suitable anti-diarrhea drugs may be included in the kits or compositions of the present invention include, for example, loperamide, and/or pharmaceutically-acceptable salts thereof.

Second therapeutic agents may be co-formulated and/or co-administered with an indole compound. In such co-formulations, a second therapeutic agent may be at a concentration of less than 20%, 19%, 18%, 17%, 16%, 15%, 14%, 13%, 12%, 11%, 10%, 9%, 8%, 7%, 6%, 5%, 4%, 3%, 2%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, a second therapeutic agent may be co-formulated with an indole compound. In such co-formulation, the second therapeutic agent may be at a concentration greater than 20%, 19.75%, 19.50%, 19.25% 19%, 18.75%, 18.50%, 18.25% 18%, 17.75%, 17.50%, 17.25% 17%, 16.75%, 16.50%, 16.25% 16%, 15.75%, 15.50%, 15.25% 15%, 14.75%, 14.50%, 14.25% 14%, 13.75%, 13.50%, 13.25% 13%, 12.75%, 12.50%, 12.25% 12%, 11.75%, 11.50%, 11.25% 11%, 10.75%, 10.50%, 10.25% 10%, 9.75%, 9.50%, 9.25% 9%, 8.75%, 8.50%, 8.25% 8%, 7.75%, 7.50%, 7.25% 7%, 6.75%, 6.50%, 6.25% 6%, 5.75%, 5.50%, 5.25% 5%, 4.75%, 4.50%, 4.25%, 4%, 3.75%, 3.50%, 3.25%, 3%, 2.75%, 2.50%, 2.25%, 2%, 1.75%, 1.50%, 125%, 1%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% w/w, w/v or v/v.

In some embodiments, a second therapeutic agent may be co-formulated with an indole compound such that the final formulation has a concentration of the second therapeutic agent that is in the range of from approximately 0.001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v. It is understood that the final concentration is dependent on many factors known to persons skilled in the art including, but not limited to, location and size of the treatment site.

In some embodiments, a composition herein comprises less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g of the one or more second therapeutic agents herein.

In some embodiments, a composition herein comprises more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5 g, 4 g, 4.5 g, 5 g, 5.5 g, 6 g, 6.5 g, 7 g, 7.5 g, 8 g, 8.5 g, 9 g, 9.5 g, or 10 g of the one or more second therapeutic agents herein.

In some embodiments, a composition herein comprises 0.0001-10 g, 0.0005-9 g, 0.001-8 g, 0.005-7 g, 0.01-6 g, 0.05-5 g, 0.1-4 g, 0.5-4 g, or 1-3 g of the one or more second therapeutic agents herein.

Kits

The present disclosure provides a kit for the reduction or removal of localized fat deposits and/or skin and soft tissue tightening in the subject. The kit can provide a non-surgical method of reduction or removal of localized fat deposits and/or skin and subcutaneous tissue tightening in the subject. The kit includes one or more containers. A container comprises any of the compositions herein. For example, a container can comprise an indole compound. In certain embodiments, a syringe can comprise an indole compound. In some embodiments, the indole compound is a compound of Formula (I).

In some embodiments, an indole compound may be prepared in a solution or in an injectable solution. A container comprising such a solution may have sufficient volume to hold one or more unit doses. For example, a container may be adapted to hold a less than 500 ml, 100 ml solution, 20 ml solution 10 ml solution or 5 ml solution. In some embodiments, a container can hold a volume of about 0.01 ml to about 100 ml, about 0.1 ml to about 90 ml, about 0.5 ml to about 80 ml, about 1 ml to about 70 ml, about 2 ml to about 60 ml, about 3 ml to about 50 ml, about 4 ml to about 40 ml, about 5 ml to about 30 ml, about 6 ml to about 20 ml, and about 7 ml to about 10 ml. In certain embodiments, a container is an ampule having a volume capacity of about 10 to about 20 ml.

In some embodiments, an indole compound is formulated in a transdermal patch or a subdermal depot for sustained release. Dosages in a patch or depot can be the same as those discussed herein.

The container can optionally include one or more second therapeutic agents. In certain embodiments, a container includes an analgesic, antimicrobial agent, or anti-inflammatory agent. The kit may further include a second container comprising a second active agent. Examples of a second therapeutic agent in a second container include, for example, an antimicrobial agent, an anti-thrombotic agent, an anti-coagulation agent, an anti-inflammatory agent, an analgesic, an anesthetic, an anti-dispersion agent, a dispersion agent, a penetration enhancer, a steroid, a tranquilizer, a muscle relaxant, and an anti-diarrhea agent.

The solution of container is administered according to the instructions for use. Instructions for use can provide dosing instructions which may depend upon, for example, location of target site, animal being treated, desired results, size of target site, concentration of the indole compound in composition, etc. In certain embodiments, instructions for use are for the treatment of an animal such as a human, a dog, a cat, or a horse. Instructions for use can also include information for treatment of other domesticated animals and/or farm animals. Instruction for use may also include information on the use of the compositions herein to treat specific target sites, such as, e.g., fat deposits or areas of loose skin localized under eye, under chin, under arm, buttock, cheek, brow, calf, back, thigh, ankle, or stomach. In some embodiments, instruction for use detail an explanation for use of the compositions herein to treat a fat condition of obesity, fat redistribution syndrome, dorsocervical fat, visceral adiposity, breast enlargement, breast ptosis, localized lipodystrophy with or without associated pendulosity, hyperadiposity, eyelid fat herniation, lipomas, lipodystrophy, buffalo hump lipodystrophy, diffused body fat around trunk and arms, or fat deposits associated with cellulite.

In some embodiments, instructions for use detail an explanation for use of the compositions herein to prevent or reduce a skin condition associated with aging, such as lax skin, and subcutaneous tissue, a localized pendulous overhang of skin and subcutaneous tissue, irregularities of the skin, and wrinkles.

Instruction for use may include information regarding proper diluents and volumes for dilution, if any, of the container. The instructions for use may also provide information regarding the proper administration of the compositions herein, such as frequency and dosage of administration.

The kit may further comprise a syringe or other suitable delivery device (e.g., transdermal pump, transdermal patch, or subdermal depot) for delivering the compositions in the container to a localized fat deposit or loose skin. In some embodiments, a syringe or delivery device may be preloaded with a unit dose of a solution of the present invention. In certain embodiments, a syringe or delivery device may be preloaded with a fat-dissolving or skin-tightening effective amount of an indole compound.

EXAMPLES

The following examples are offered to illustrate but not to limit the invention.

Example 1

The time and concentration dependent effects of drug substance on both cell viability and toxicity were evaluated using a two-color fluorescence assay that measures plasma membrane integrity and intracellular enzyme activity. Live cells are determined by the strong fluorescence of calcein AM upon enzymatic conversion. In contrast, ethidium bromide signal is dramatically increased upon entering a cell with damaged membranes and binding to nucleic acids. The ratio of ethidium to calcein fluorescence is an excellent measure of the relative amount of live and dead cells.

Test compounds are commercially available. Test compounds include compounds from Table 1. Comparative non-indole compounds were also tested: C-8, C-19, C-20, C21, C-56, C-57, C-58, C-60, and C-61. Positive controls include 1% sodium deoxycholate (DC) (MasterPharm, Richmond Hill, N.Y.), phosphatidylcholine 25 mg/ml plus deoxycholate 12 mg/ml (MasterPharm, Richmond Hill, N.Y.), PC 50/DC24 (Network Lipolysis, Drensteinfurt, Germany) and Aqualyx®, a sodium deoxycholate in a lactose carrier. Compound 44H is a high concentration version of Compound 44.

Figure 2:
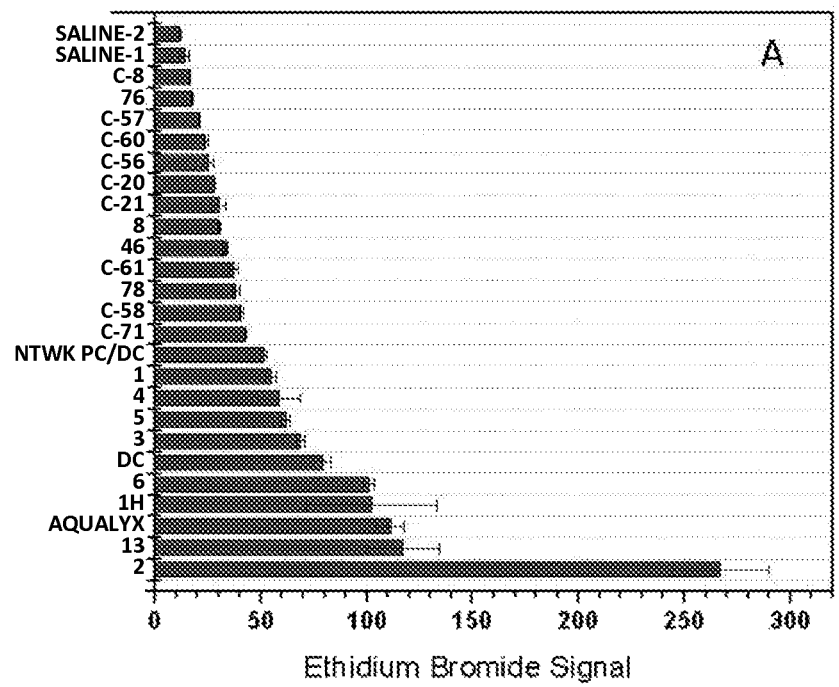
FIG. 2. Histogram profiles of Ethidium Bromide Fluorescence Intensity and signal ratio at (A-B) 1 hour (C-D) 4 hours (E-F) 18 hours and (G-H) 24 hours after incubation of adipocytes with test compounds. The signal ratio is a normalized measure of cell death that incorporates live cell quantity.
Figure 2:
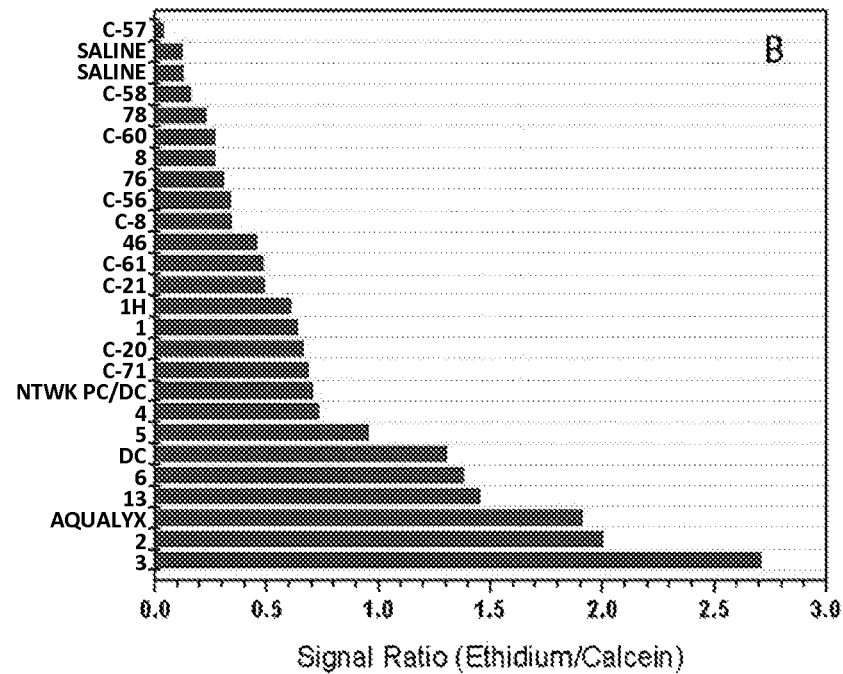
Figure 2:
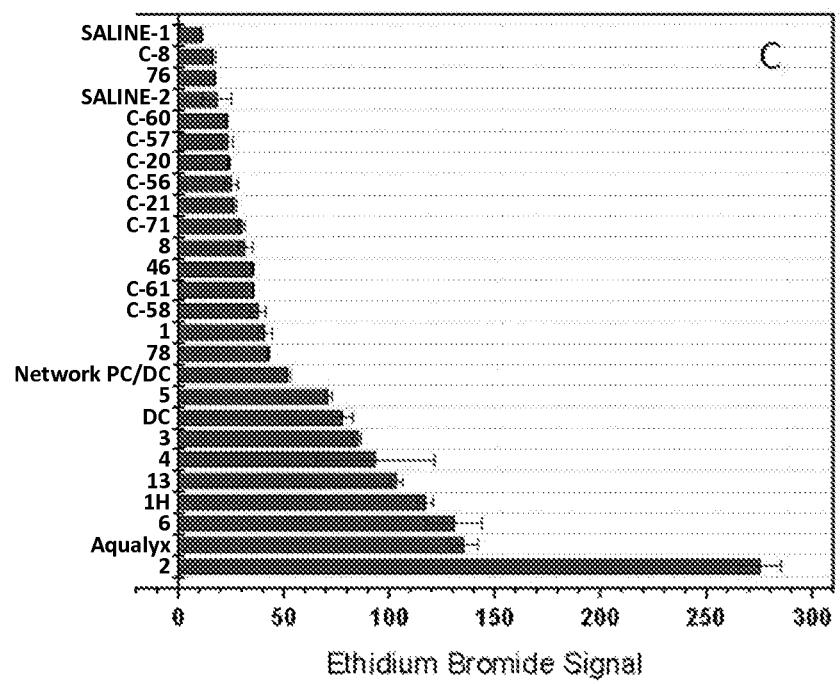
Figure 2:
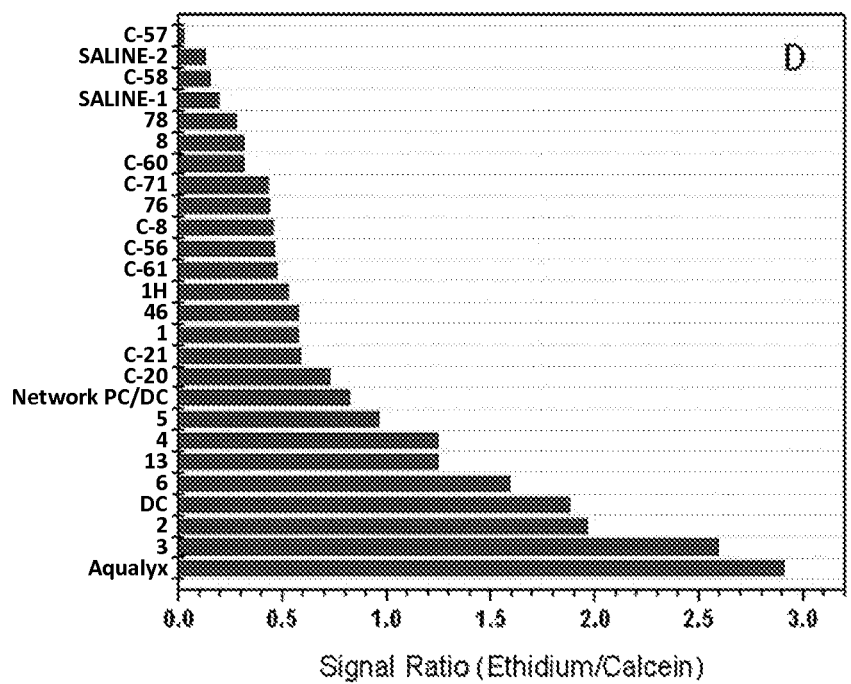
Figure 2:
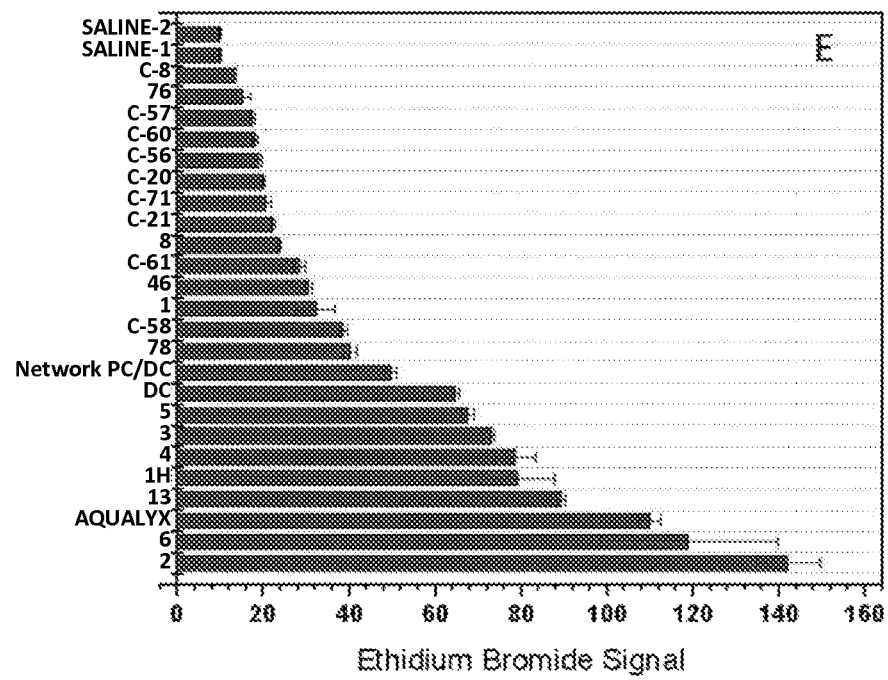
Figure 2:
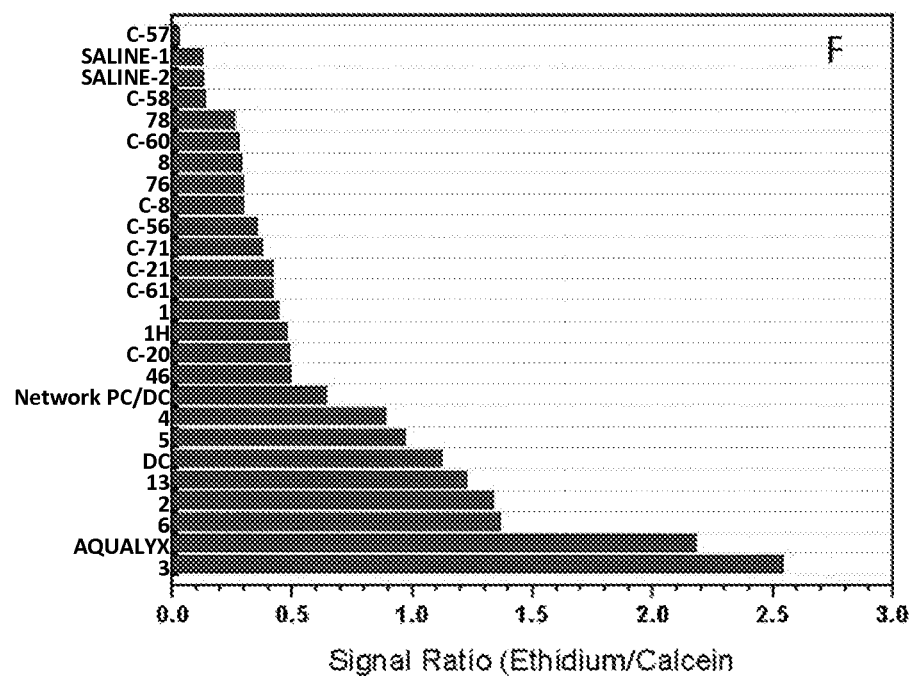
Figure 2:
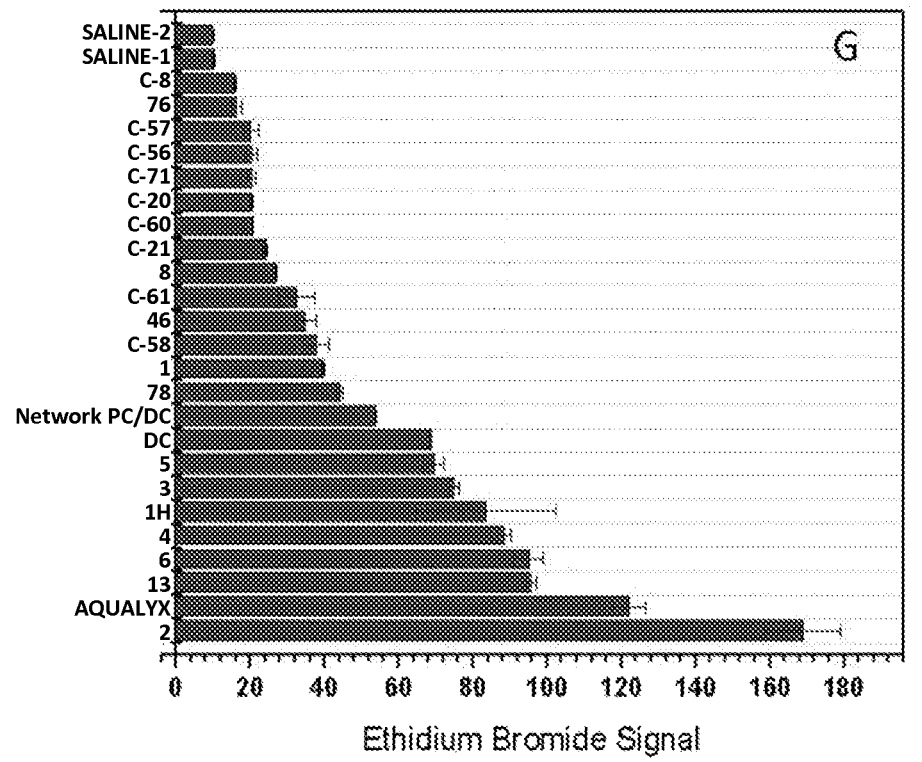
Figure 2:
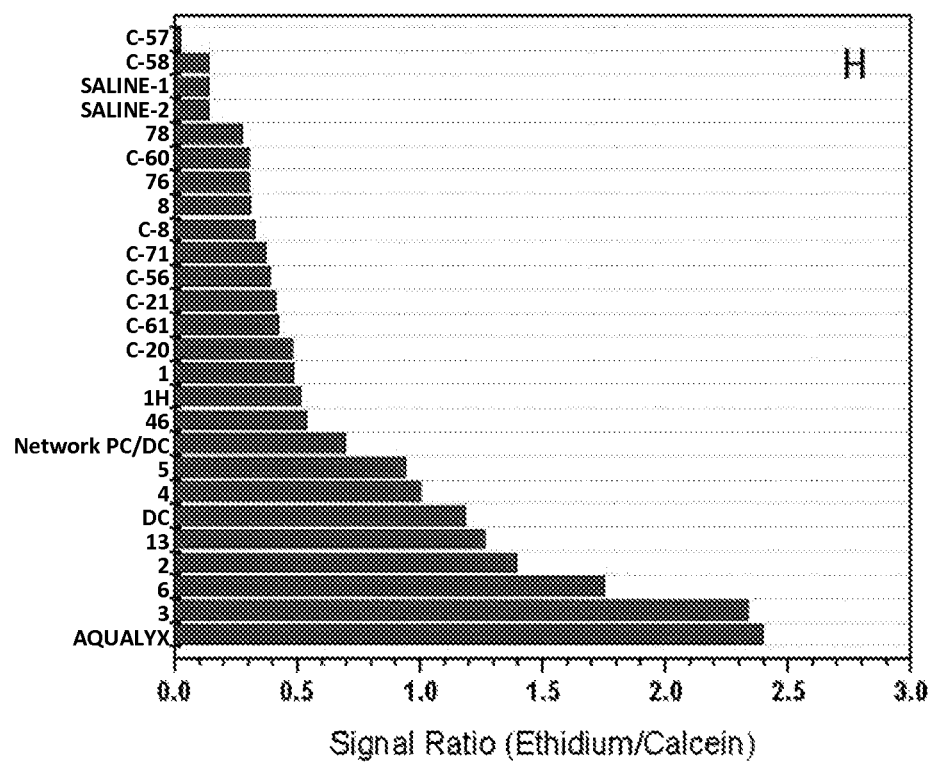

The effects of various test compounds were compared to currently available known cytotoxic compounds (positive controls) including Aqualyx, deoxycholic acid (DC), and the two combinations of phosphatidylcholine and deoxycholic acid (PC/DC) on cell viability and toxicity. Saline was used as a negative control. All compounds were incubated with approximately 1-2 million cells/ml for varying amounts of time to induce cell death and/or disrupt membrane integrity. The compounds tested showed a gradient of adipocyte killing behavior as a function of time ranging from very aggressive to modest cell death (FIGS. 1 and 2). FIG. 1 suggests that there are multiple compounds that have more aggressive, intermediate, and less aggressive cell killing behavior as compared to the positive controls Aqualyx, DC, and PC/DC (FIGS. 1 and 2).

Figure 3:
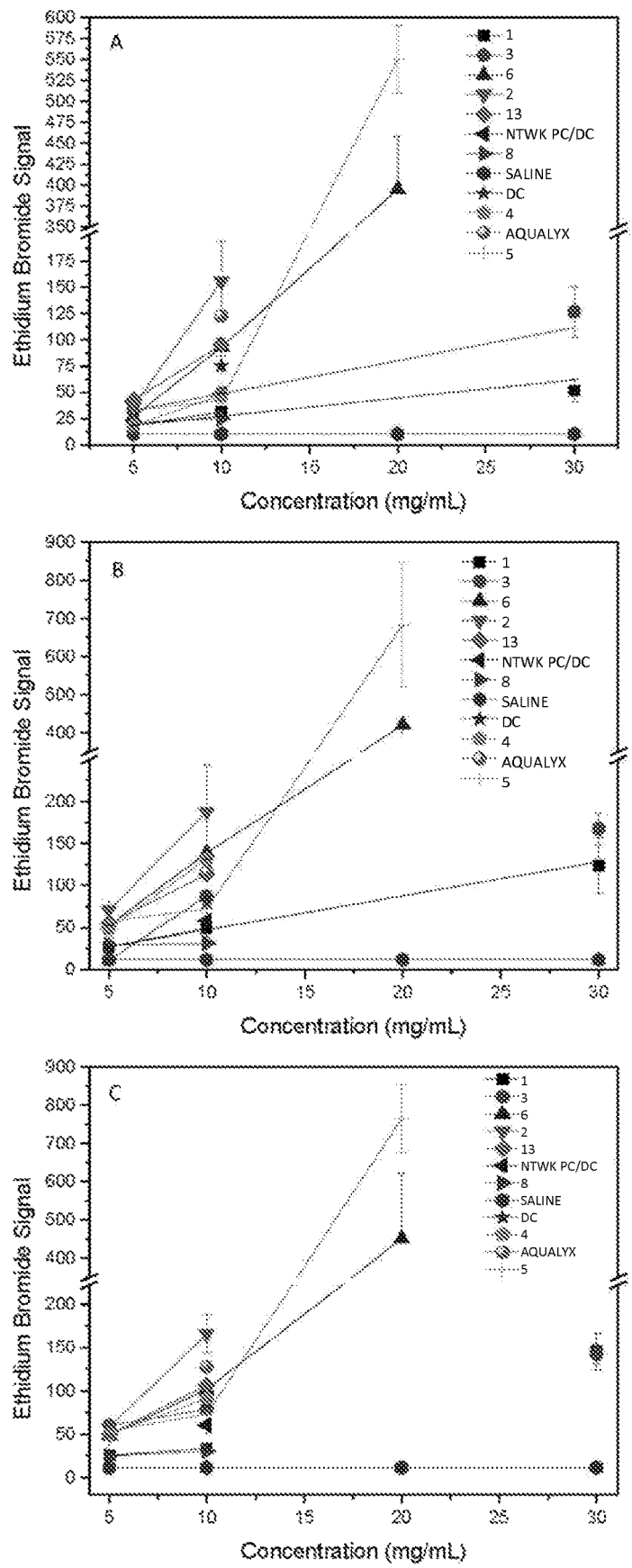
FIG. 3. Concentration dependent effects of test compounds on adipocyte cell cytotoxicity (EB signal) after incubation for (A) 1 hour (B) 12 hours and (C) 24 hours.
Figure 4:
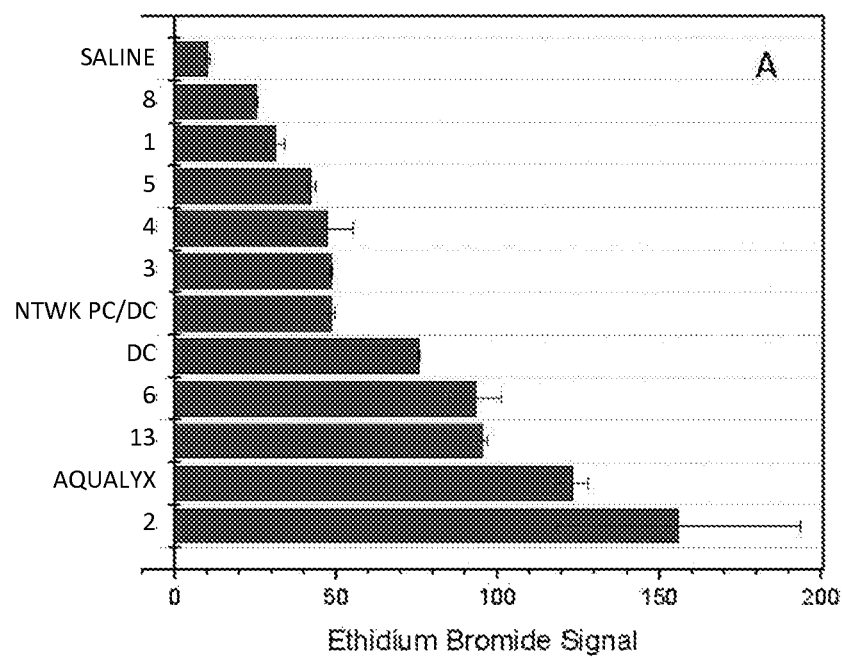
FIG. 4. Histogram profiles of Ethidium Bromide Fluorescence Intensity and signal ratio after incubation of adipocytes with 10 mg/ml drug substance for (A-B) 1 hour (C-D) 12 hours and (E-F) 24 hours.
Figure 4:
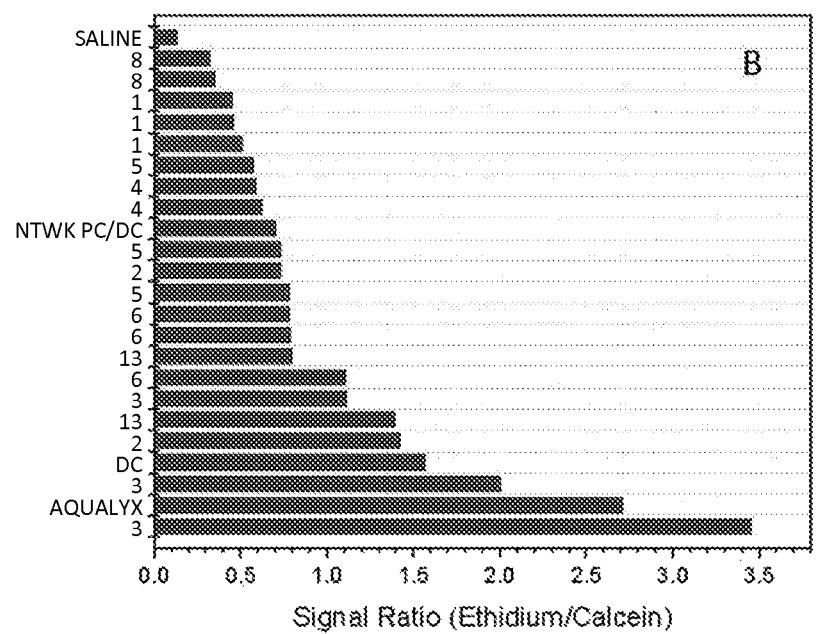
Figure 4:
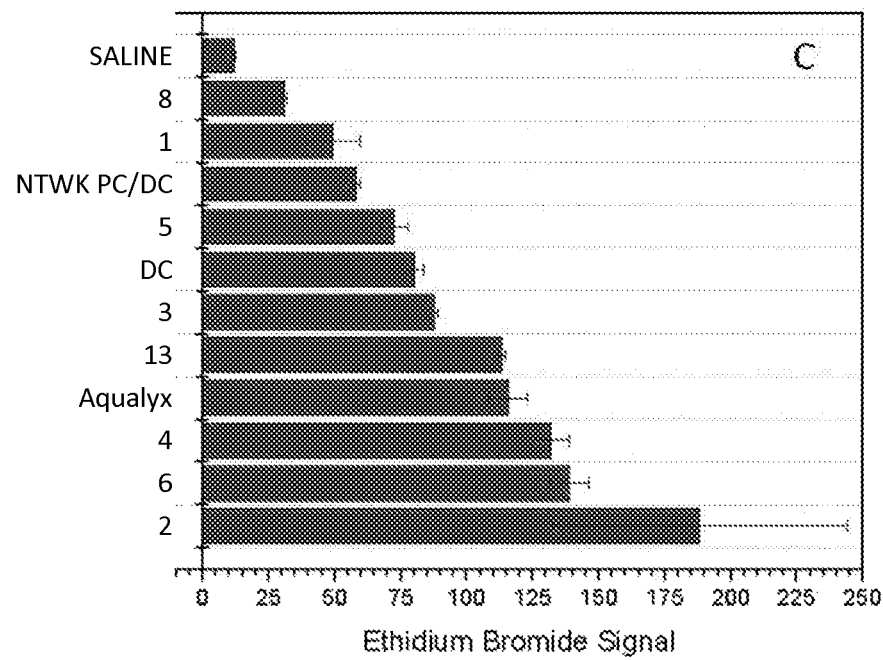
Figure 4:
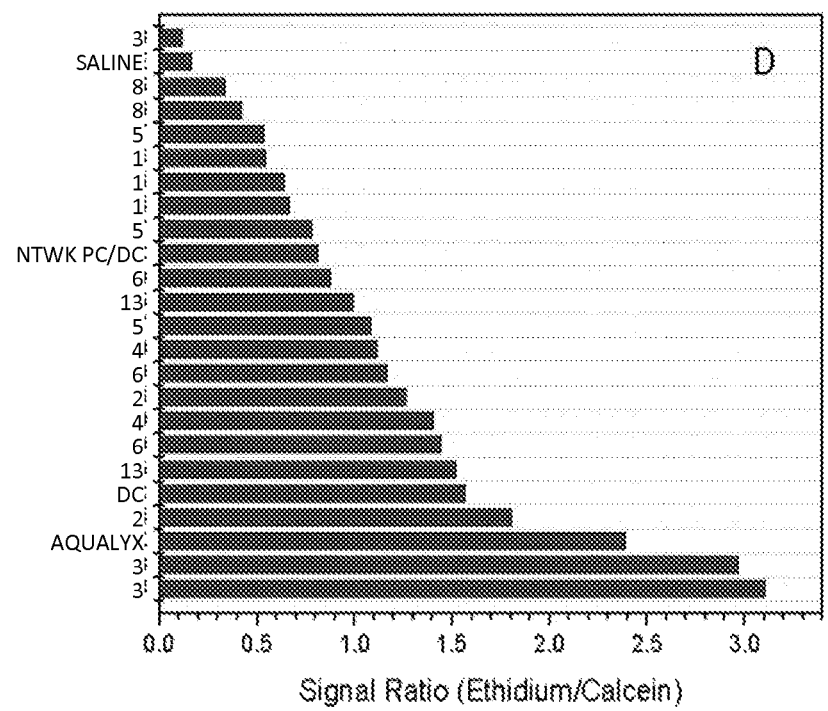
Figure 4:
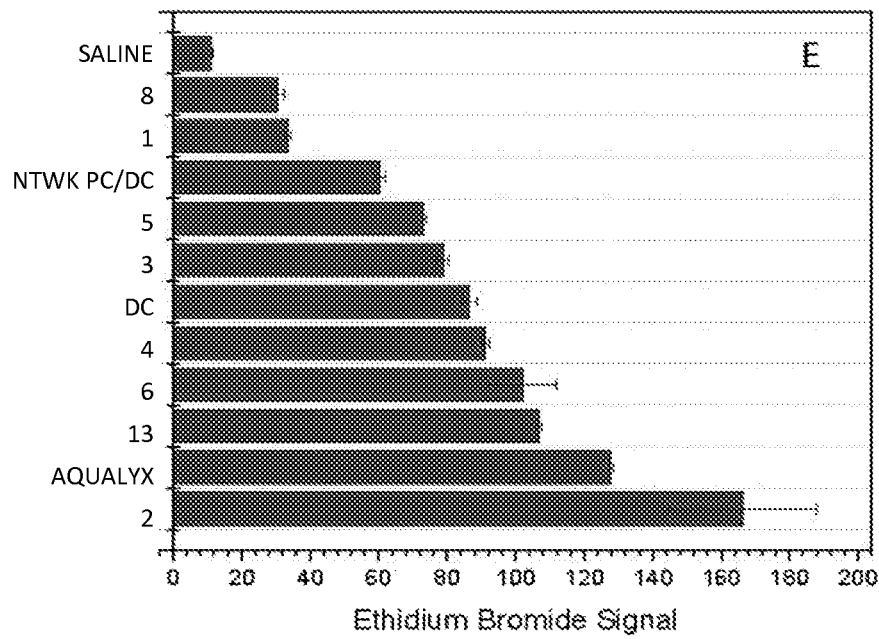
Figure 4:
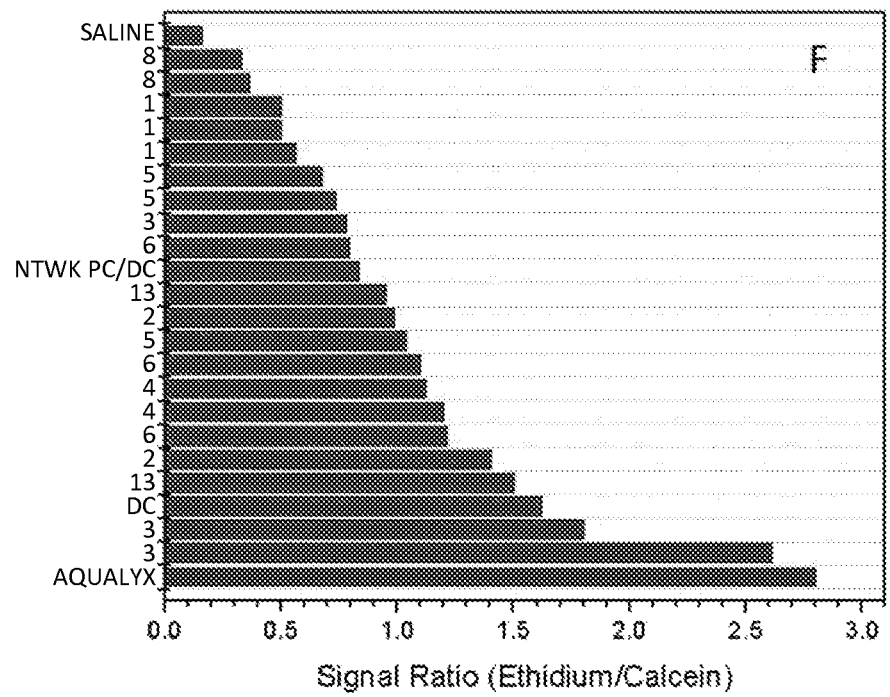

In a separate study, the influence of both test compound concentration and incubation time on cell viability and cytotoxicity of adipocytes was evaluated (FIGS. 3 and 4). FIGS. 3 and 4 shown that increasing test compound concentration generally increases the ethidium bromide signal (cell death). Similar to the previous time dependent study, an initial increase in cell death followed by a plateau and a diverse range of test compound activity from aggressive to non-aggressive cell cytotoxicity was observed.

Example 2

Indole compounds were tested in immediate ex-vivo tissue. Test compounds include a negative control (saline) which shows no response, or normal adipocyte architecture. In all specimens, some shearing (linear tears) and compression artifacts (rectangular fat cells rather than round) were present, as fatty tissue is notoriously difficult to keep from fragmenting during histologic processing. In order to prevent interpretation errors, the treatment zone located in the center of the specimen was evaluated from the dermal/fat junction distally, and only if adjacent to a section of normal appearing fat.

Test compounds included indole compounds in Table 1. Compounds to be tested for tissue preference were first screened for adipocyte cytoxicity in order to qualify. In addition to normal saline and compound diluent (DMSO plus PBS) (negative controls), positive controls include 1% sodium deoxycholate (MasterPharm, Richmond Hill, N.Y.), phosphatidylcholine 25 mg/ml plus deoxycholate 12 mg/ml (MasterPharm, Richmond Hill, N.Y.), PC 50/DC24 (Network Lipolysis, Drensteinfurt, Germany) and Aqualyx®, a sodium deoxycholate in a lactose carrier (Marllor International, Italy).

Initial screening was performed using a variety of cell viability and cytotoxicity assays, including Presto Blue® (Invitrogen, Grand Island, N.Y.), Alamar Blue® (Invitrogen, Grand Island, N.Y.), Cyto-Tox One® (Promega, Madison, Wis.), and Cell Titer Glo® (Promega, Madison, Wis.). Due to reaction of several test compounds with the blue dye, the redox assays were discontinued. An MTT terazolium assay was performed, as well as LDH and ATP based assays. It was determined that the most consistency occurred with the dual function assays, Multi-Tox Fluor® (Promega, Madison, Wis.) and LIVE/DEAD® for mammalian cells (Invitrogen, Grand Island, N.Y.). The LIVE/DEAD® for mammalian cells assay was used. LIVE/DEAD® for mammalian cells assay is a calcein (live read)/ethidium bromide (dead) multiplex assay.

Figure 5:
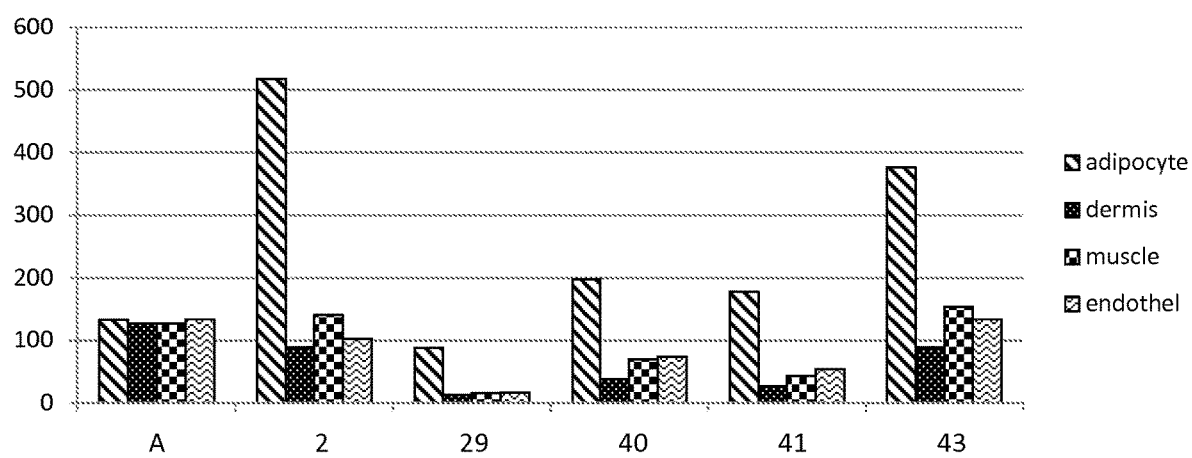
FIG. 5. LIVE/DEAD® assay results for test compounds for adipocytes, dermis, muscle, and endothelial cells for Compound A (Aqalyx®) and Compounds 2, 29, 40, 41, and 43.

There was a wide range of tissue preference ranging from none-all compounds were indiscriminately cytotoxic—to about 90%. Indole (Compound 33) was fairly tissue preferential at about 53-56%. Ethidium results for indole for dermis, muscle, and endothelial cells showed that indole was less than half toxic for those cells than for adipocytes at 4 time points over 24 hours. FIG. 5 shows results for test compounds for adipocytes, dermis, muscle, and endothelial cells for Compound A (Aqualyx®) and Compounds 2, 29, 40, 41, and 43.

As shown in FIG. 5, the most strongly tissue preferential group included six tested compounds, Compounds 2 and 43 in the aggressive category, Compounds 40 and 41 in the moderate range, and Compounds 29 in the less aggressive range. (Compound 10 is not shown in FIG. 5.) These compounds had adipocyte cytotoxicity numbers that are 3 to 4 times stronger than those noted with other tissue types. Additional data for tissue specificity results are shown in the table below.

In general, the PC/DC compositions were indiscriminate. Aqualyx® had slight tissue specificity toward nerve tissue and endothelial tissue. The deoxycholate composition was indiscriminate.

Figure 6:
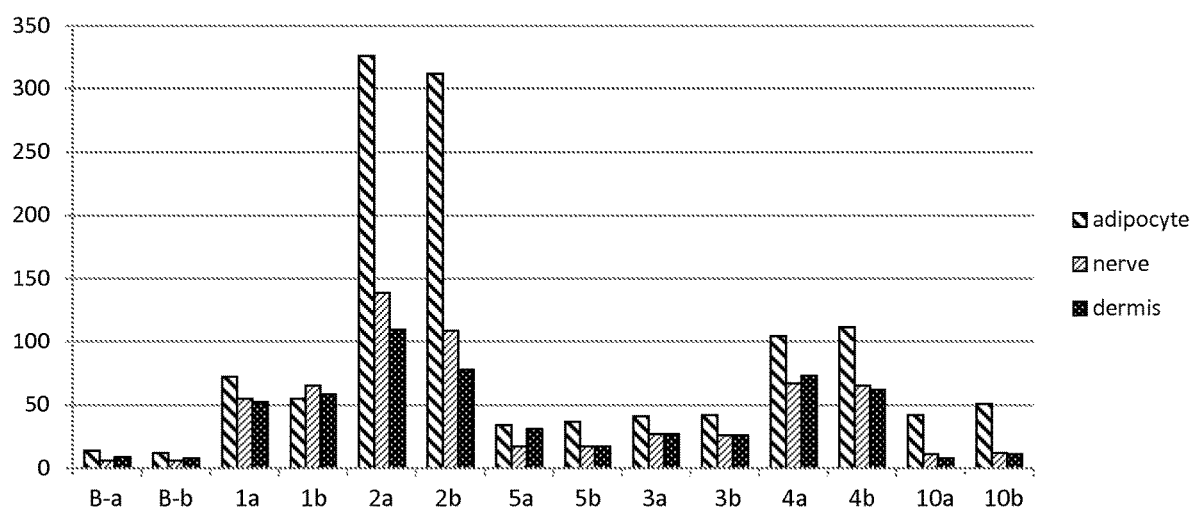
FIG. 6. LIVE/DEAD® assay results for test compounds for adipocytes, dermis, and muscle cells for Compound B (saline control) and Compounds 1, 2, 3, 4, 5, and 10. All the bars in FIG. 9 indicate kill rate (ethidium). In the compound number, "a" refers to compound tissue preference at 2 hours. In the compound number, "b" refers to compound tissue preference at 5 hours.

FIG. 6 shows results for test compounds for adipocytes, dermis, and muscle cells for Compound B (saline control) and Compounds 1, 2, 3, 4, 5, and 10. All the bars in FIG. 6 indicate kill rate (ethidium). In the compound number, "a" refers to compound tissue preference at 2 hours. In the compound number, "b" refers to compound tissue preference at 5 hours.

As shown in FIG. 6, Compounds 2 and 10 were the most aggressive in this group of compounds. Compound 4 was less aggressive, but shows specificity for adipocyte killing. Compound 1 showed no preference for cells over time. Compound 5 showed more nerve preservation, but a late dermal spike appeared.

Figure 7:
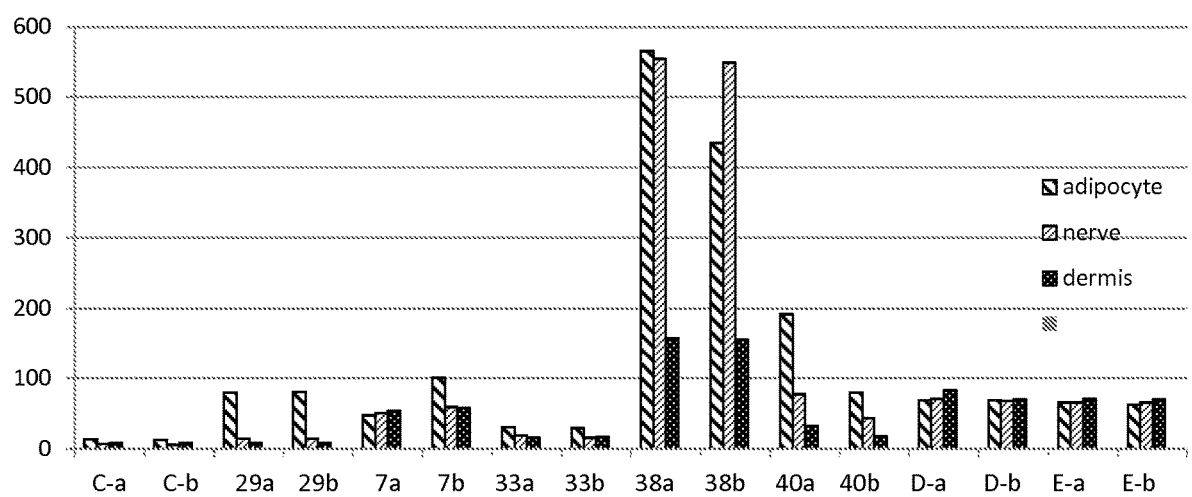
FIG. 7. LIVE/DEAD® assay results for test compounds for adipocytes, dermis, and muscle cells for Compound C (saline control), Compounds D and E (deoxycholate), and Compounds 29, 7, 33, 38, and 40. All the bars in FIG. 7 indicate kill rate (ethidium). In the compound number, "a" refers to compound tissue preference at 2 hours. In the compound number, "b" refers to compound tissue preference at 5 hours.

FIG. 7 shows results for test compounds for adipocytes, dermis, and muscle cells for Compound C (saline control), Compounds D and E (deoxycholate), and Compounds 29, 7, 33, 38, and 40. All the bars in FIG. 7 indicate kill rate (ethidium). In the compound number, "a" refers to compound tissue preference at 2 hours. In the compound number, "b" refers to compound tissue preference at 5 hours.

In FIG. 7, Compound C is a saline control; Compound D is phosphatidylcholine 25 mg/ml plus deoxycholate 12 mg/ml; and Compound E is phosphatidylcholine 25 mg/ml plus deoxycholate 24 mg/ml. Both of Compounds D and E are detergents that showed no tissue specificity. Recent reports following clinical trials of 1% deoxycholate show two instances of facial nerve palsy and numbness with paresthesias in up to 40% of patients treated. Compounds D and E are toxic to nerve and dermal fibroblasts as they are to adipocytes.

As shown in FIG. 7, Compound 29 is strongly adipocyte preferential, while the adipocyte kill rate is equivalent to that of Compounds D and E. Compound 7 showed not tissue preference. Compound 33 showed definite tissue specificity at two time points. While the specificity is not as strong as other compounds tested, there is much more tissue specificity than with Compounds D and E. Compound 38 was an aggressive adipocyte killer and is also toxic to nerve cells, although not nearly as toxic to dermal fibroblasts. Compound 40 showed tissue specificity at two time points. In FIG. 7, Compounds 29 and 40 showed the most specificity for adipocyte killing among the compounds tested in this group. Compound 33 showed moderate tissue specificity, but a fairly low adipocyte kill rate.

Figure 8:
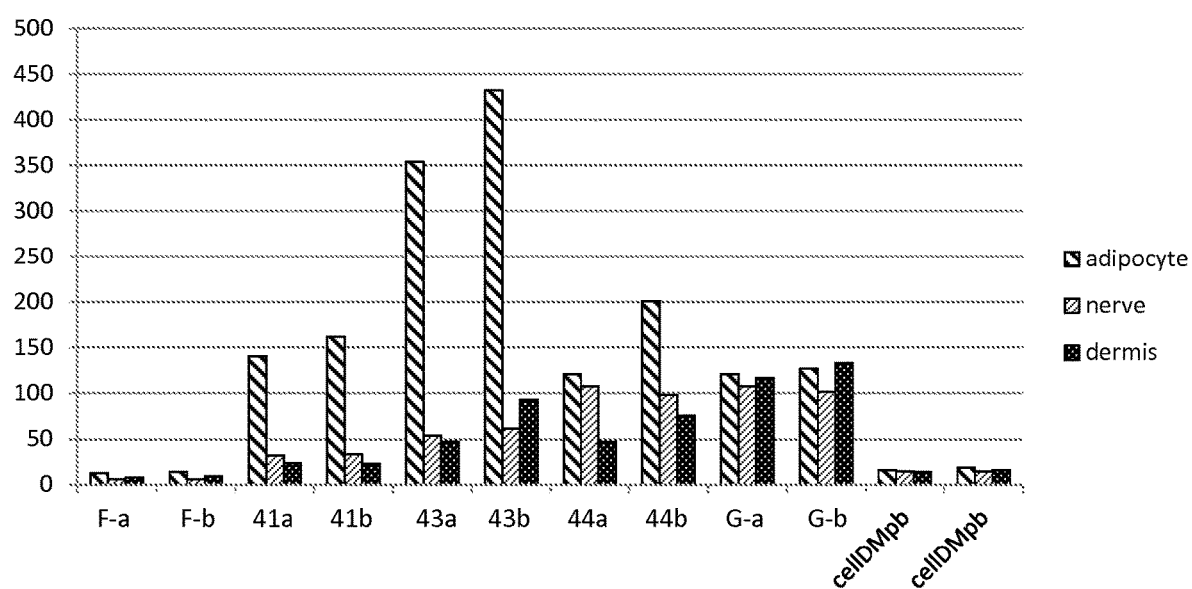
FIG. 8. LIVE/DEAD® assay results for test compounds for adipocytes, dermis, and muscle cells for Compound F (saline control), Compounds G (Aqalyx®), and Compounds 41, 43, and 44. All the bars in FIG. 8 indicate kill rate (ethidium). In the compound number, "a" refers to compound tissue preference at 2 hours. In the compound number, "b" refers to compound tissue preference at 5 hours.

FIG. 8 shows results for test compounds for adipocytes, dermis, and muscle cells for Compound F (saline control), Compounds G (Aqualyx®), and Compounds 41, 43, and 44. All the bars in FIG. 8 indicate kill rate (ethidium). In the compound number, "a" refers to compound tissue preference at 2 hours. In the compound number, "b" refers to compound tissue preference at 5 hours.

In FIG. 8, Compound F is a saline control; Compound G is Aqualyx®. Compound G showed no tissue specificity. Compounds H and I are diluent controls, which include cells and DMSO/PBS. CellDMpb is a diluent having DMSO and PBS and cells.

As shown in FIG. 8, Compound 41 had a high tissue preference index and strong adipocytolytic capability. Compound 41 is not as aggressive as Compounds 2, 38, or 43. Compound 43 is adipolytic, yet has a low kill rate for nerve cells and dermis. It is a more aggressive than Compound 41. Compound 41 would be effective in areas where there is a large fat deposit. Compound 44 is not as specific as the other compounds tested in this group.

The following table shows tissue specificity results for the tested compounds. A sample of DMSO/PBS was a negative control. A sample of Aqualyx® was a positive control. In the table, 24M is phosphatidylcholine 25 mg/ml plus deoxycholate 12 mg/and 25N is C 50/DC24; these were positive controls. The numbers in the table refer to averaged ethidium numbers. The percentages represent the relative kill rate for each cell type when rated against the adipocyte kill rate for that compound. All tissue types were tested on the same plate against adipocytes in order to standardize results.

| Compound # | Adipocyte | Nerve | Dermis | Muscle | Endothelial |
| --- | --- | --- | --- | --- | --- |
| DMSO/PBS | 17.7 | 15 | 16 | 15.5 | 14.5 |
| 24M | 72 | 69.5 | 76 | 74 | 76.5 |
| 25N | 65.5 | 66 | 70 | 68.5 | 67 |
| Aqualyx ® | 124 | 105 (85%) | 123 | 120 | 111 (90%) |
| 78 | 29.5 | n/a | 8.3 (28%) | 8.7 (29%) | 9.8 (33%) |
| 1 | 53 | 60 | 56 | 82 | 98 |
| 2 | 360 | 124 (39%) | 101 (28%) | 93 (26%) | 116 (32%) |
| 5 | 36 | 17 (47%) | 17 (47%) | 27 (75%) | 16 (44%) |
| 3 | 42.5 | 26 (61%) | 26.5 (62%) | 25 (59%) | 25 (59%) |
| 4 | 127 | 66 (52%) | 79 (62%) | 99 (78%) | 86 (63%) |
| 10 | 45 | 12 (27%) | 10 (22%) | 13 (29%) | 16.5 (37%) |
| 29 | 83 | 15 (18%) | 9 (11%) | 14 (17%) | 8.5 (10%) |
| 7 | 196 | 56 (30%) | 103 (53%) | 119 (61%) | 69 (35%) |
| 33 | 32 | 17 (53%) | 17 (53%) | 18 (56%) | 18 (56%) |
| 38 | 558 | 551 (99%) | 148 (27%) | 362 (65%) | 289 (50%) |
| 40 | 123 | 61 (50%) | 33 (27%) | 36 (29%) | 40 (33%) |
| 41 | 149 | 32 (20%) | 27 (18%) | 40 (27%) | 44 (30%) |
| 43 | 340 | 58 (17%) | 74 (22%) | 73 (21%) | 92.5 (27%) |
| 44 | 218 | 103 (47%) | 134 (61%) | 172 (79%) | 129 (59%) |

Compounds 28, 91 and 94 showed high kill rate for adipocytes and high specificity for adipocytes over nerve cells, dermal cells, muscle cells, and endothelial cells. Compounds 78, 2, 27, and 40 showed high specificity for adipocytes over nerve cells, dermal cells, muscle cells, and endothelial cells. Compounds 5, 4, 30, 33, and 44 showed about 50% preferential for adipocytes over nerve cells, dermal cells, muscle cells, and endothelial cells. Compounds 3 and 38 showed moderate preference of adipocytes over nerve cells, dermal cells, muscle cells, and endothelial cells.

Example 3

As the indole group has not been previously used for intralesional fat reduction, a method of obtaining histologic specimens had to be modified. In 1978, May et al (Plast. Reconstr. Sug. 1978 February; 61(2): 256-67) noted that segments of human tissue remained viable and could be reattached to the body using microvascular techniques for up to 12 hours after separation. After 12 hours, a phenomenon called "no-reflow" occurred, and the tissue was no longer viable.

The tissue model described herein, therefore, was immediate ex-vivo abdominoplasty tissue that had been permitted for use by the surgical patient. Segments of abdominal skin and subcutaneous fat were injected with identified test compounds, plus a negative saline control and three positive controls: 1% deoxycholate, the commercial preparation of Aqualyx®, and the Network Lipolysis PC/DC formula.

In compounds that were identified and confirmed as adipolytic using three separate sessions of the Live/Dead cell viability assay (Invitrogen), specimens were injected and then placed into formalin at 1 hour, 4 hours, and 12 hours. Because there was no host; inflammatory changes would not be expected. This study was only performed to assess the immediacy of adipocyte changes, and to determine the method of action of each compound.

As a whole, the compounds of the embodiments appear to have a pyroptotic mechanism of action. Pyroptosis is a relatively new category of cell death mechanism. While apoptosis is programmed cell death and by definition, there is no inflammation, cytolysis causes cell membrane rupture followed by an immediate onset of swelling and inflammation in the affected area. Pyroptosis is defined as a combination of these two mechanisms, in which some cells die as a programmed function, and some cells die due to mitochondrial dysfunction or cell wall lysis or both. Pyroptosis is the central continuum between apoptosis and cell wall lysis, with some clinical and microscopic manifestations of both.

Figure 9A:
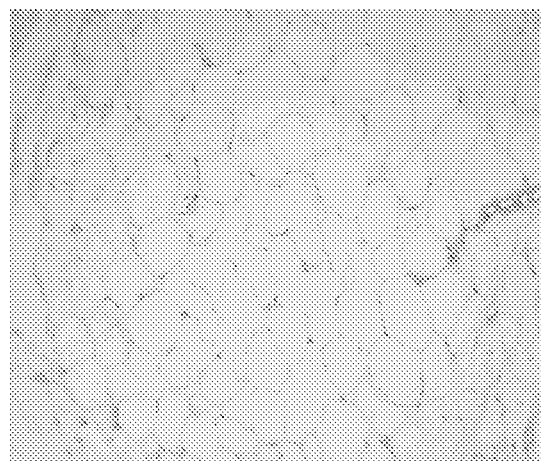
FIG. 9A shows a saline control with adipocytes intact.

FIG. 9A shows a saline control with adipocytes intact.

Figure 9B:
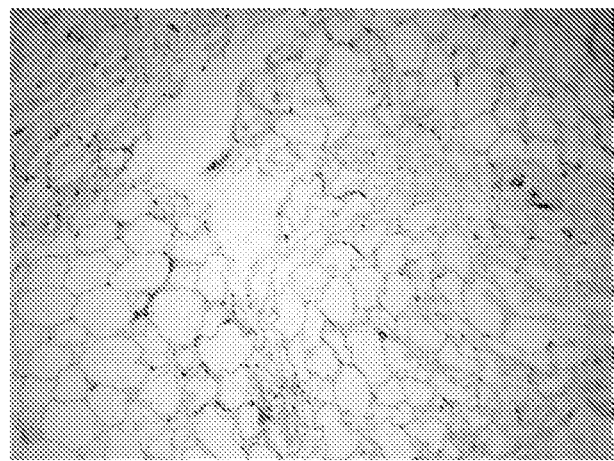
FIG. 9B shows a histology test sample with 1% deoxycholate at 4 hours.

FIG. 9B shows a histology test sample with 1% deoxycholate at 4 hours. Cell wall lysis with a large area of "missing" tissue is present. The central oblique line of injection shows significant cell damage while normal fat can be seen at the periphery, in the lower left and upper right corners. This is a classic appearance, showing the limited dispersion of the deoxycholate compound.

Figure 9C:
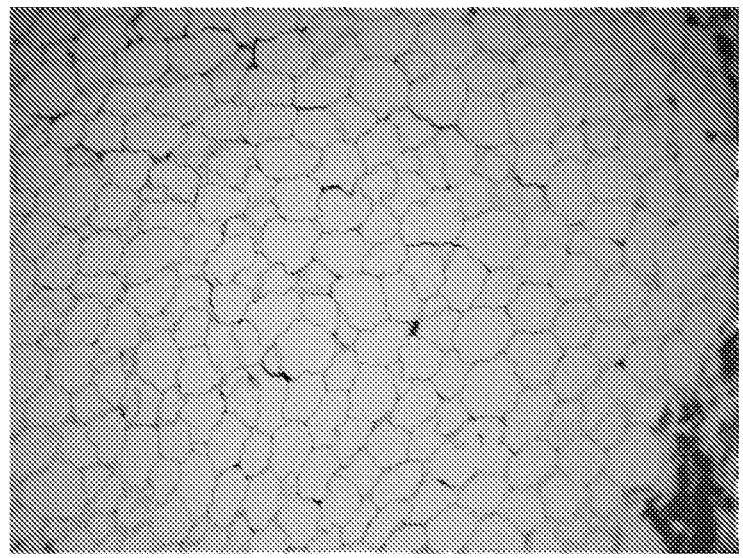
FIG. 9C shows a histology test sample with PC50/DC 24 at 12 hours.

FIG. 9C shows a histology test sample with PC50/DC 24 at 12 hours. Minor apoptotic changes such as pyknotic nuclei and "ghosting" can be seen. No cell wall lysis is present.

Figure 9D:
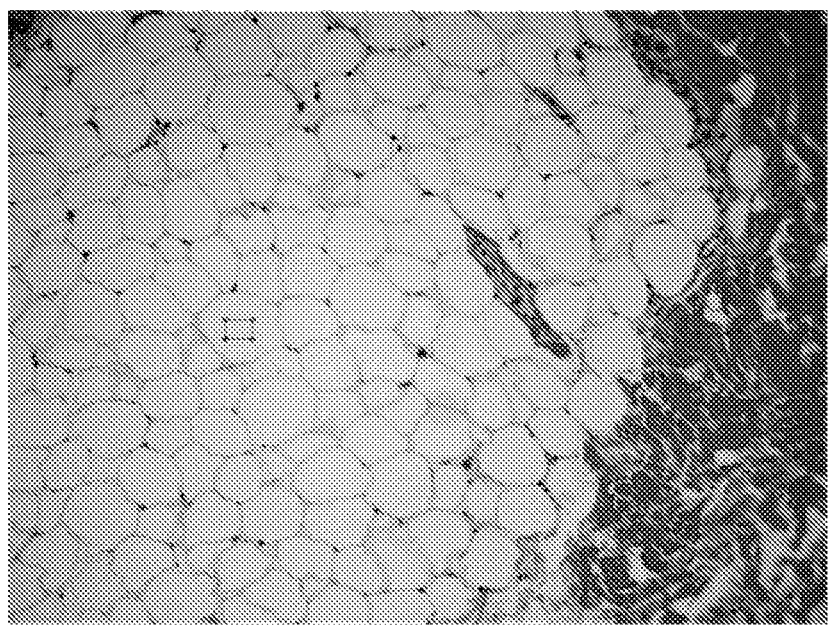
FIG. 9D shows a histology test sample with Compound 88 at 4 hours.

FIG. 9D shows a histology test sample with Compound 88 at 4 hours. The appearance is very similar to that of PC/DC. Pyknotic nuceli are present. Both ghosting and quite shrunken cells are noted with folding of the cytoplasmic membrane. This is an example of a compound with similar efficacy as PC/DC, with a primarily apoptotic mechanism of action.

Figure 9E:
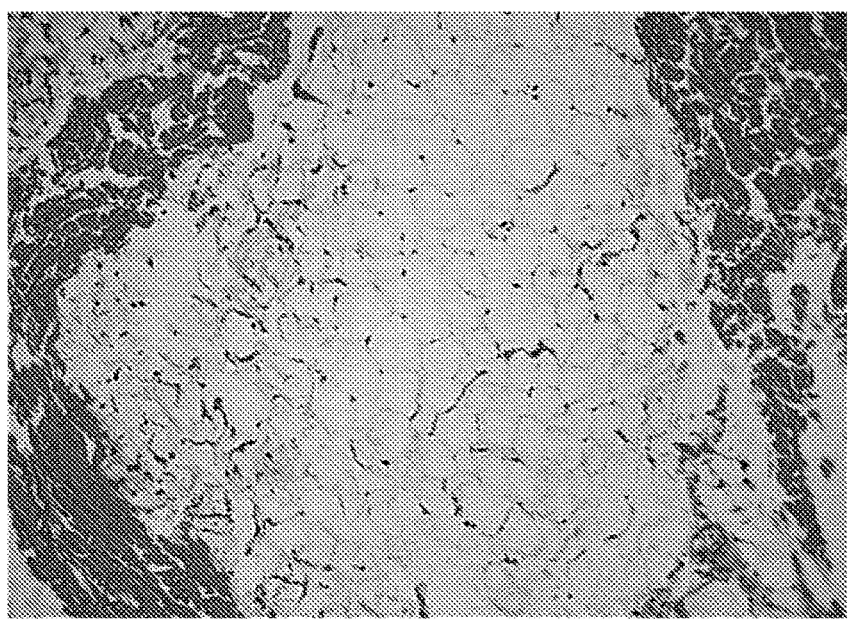
FIG. 9E shows a histology test sample with Compound 41 at twelve hours.

FIG. 9E shows a histology test sample with Compound 41 at twelve hours. Pyroptotic mechanism is well demonstrated here. Two areas of cytolysis are shown using dark arrows. Pyknotic nuclei are strongly present, as are ghosting and shrunken intact cells.

Figure 9F:
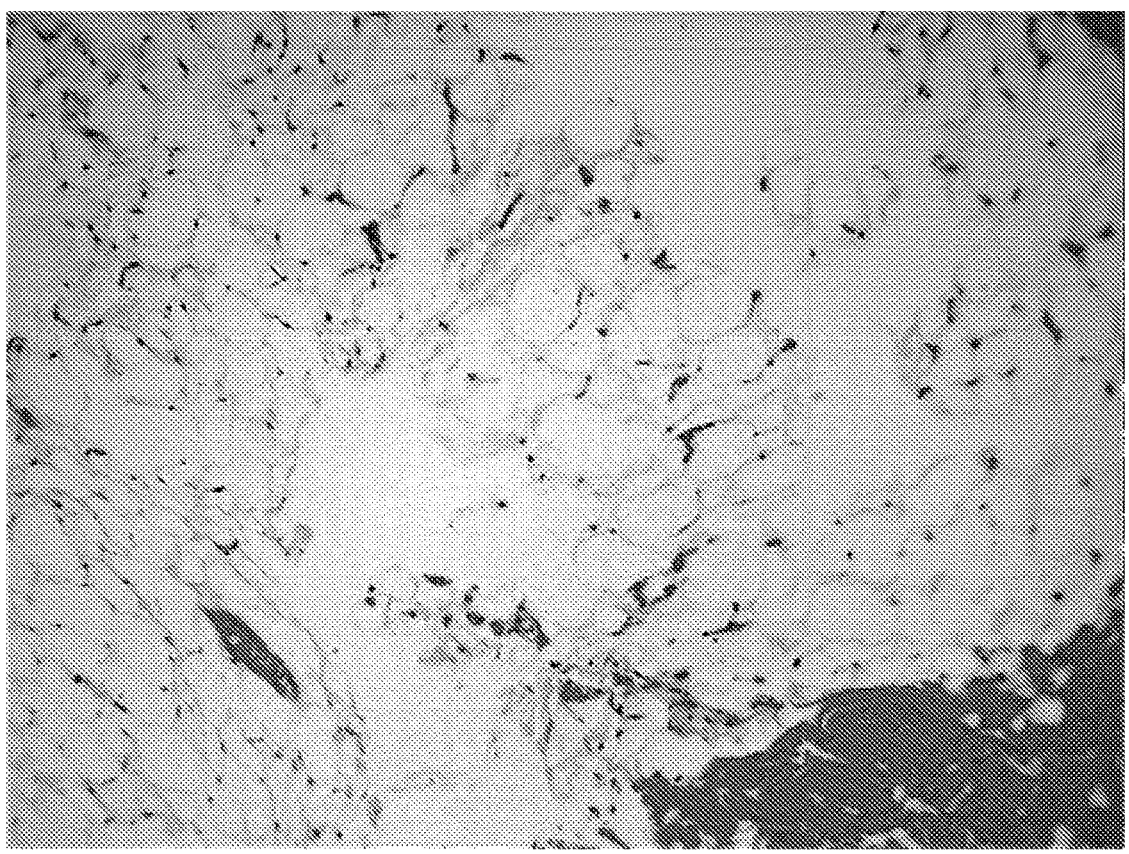
FIG. 9F shows a histology test sample with Compound 38 at four hours.

FIG. 9F shows a histology test sample with Compound 38 at four hours. The mechanism of action of this compound is primarily cytolysis, as seen by fragmentation of multiple cell walls, and empty area where adipocytes used to be. Some signs of apoptosis are present. In some embodiments, it is difficult to assign an exclusively cytolytic or apoptotic mechanism, as both are most commonly seen.

Figure 9G:
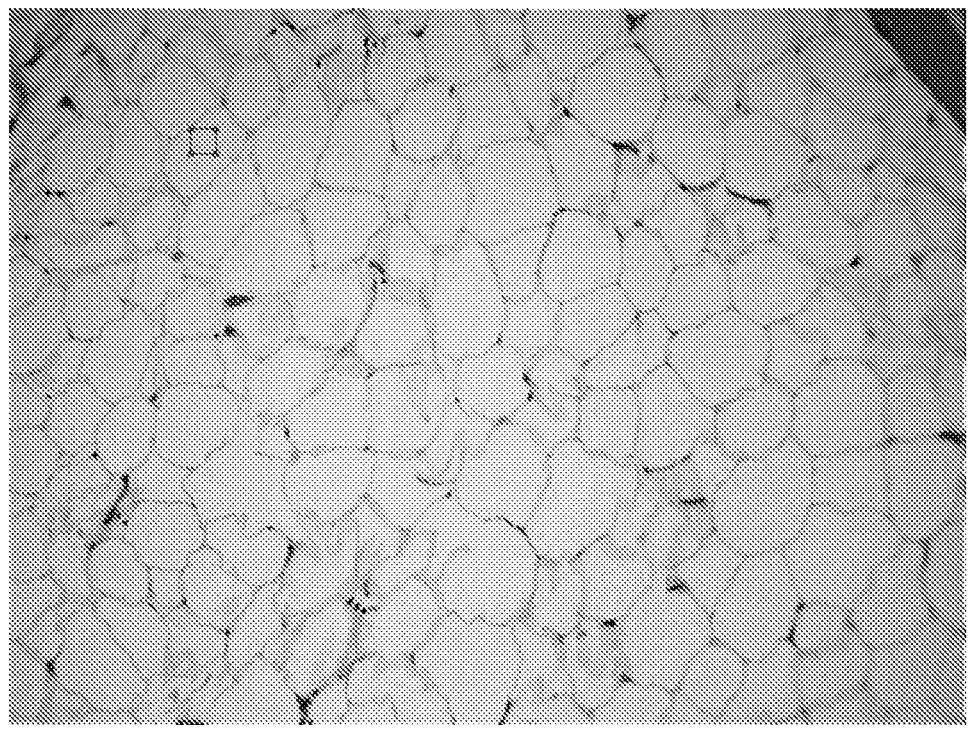
FIG. 9G shows a histology test sample with Compound 2 at 1 hour.

FIG. 9G shows a histology test sample with Compound 2 at 1 hour. This compound is aggressive, and cases more cytolysis than apoptosis.

Figure 9H:
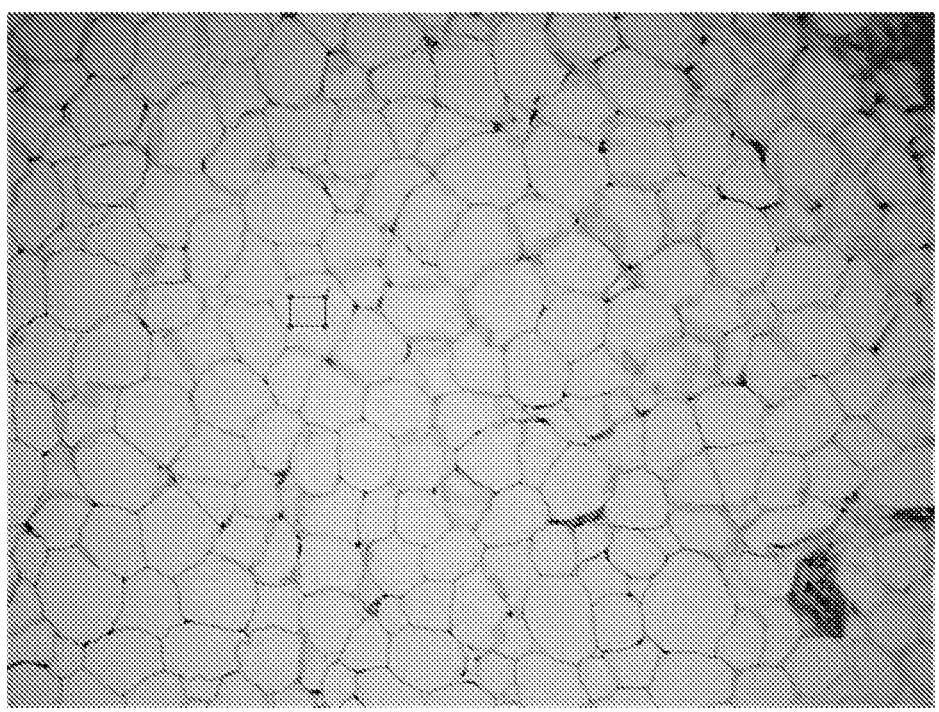
FIG. 9H shows a histology test sample with Compound 29 at 12 hours.

FIG. 9H shows a histology test sample with Compound 29 at 12 hours. This compound exhibits primarily an apoptotic mechanism.

Figure 9I:
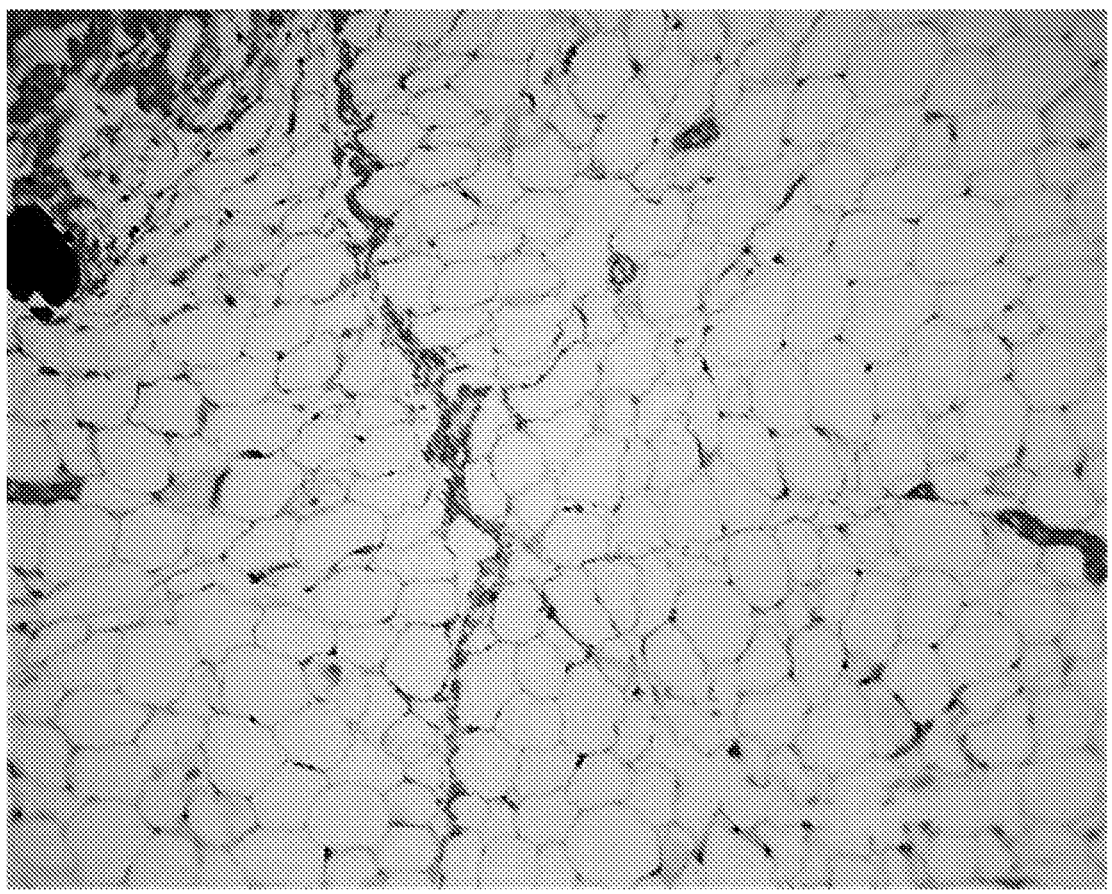
FIG. 9I shows a histology test sample with Compound 33 at 4 hours.

FIG. 9I shows a histology test sample with Compound 33 at 4 hours. Indole, the parent compound, shows pyroptotic activity when injected into adipose tissue. A tattoo marking the injection site is seen in the upper left margin. Dark arrows show regions of cytolysis. Ghosting of apoptotic cells is also visible.

In summary, the compounds of the embodiments have a variety of effects on adipocytes, with some compounds inducing more programmed cell death, and some more aggressive compounds primarily working by lysing cell membranes the majority of compounds are pyroptotic; evidence of both mechanisms of cell death is seen.

Example 4

Figure 10:
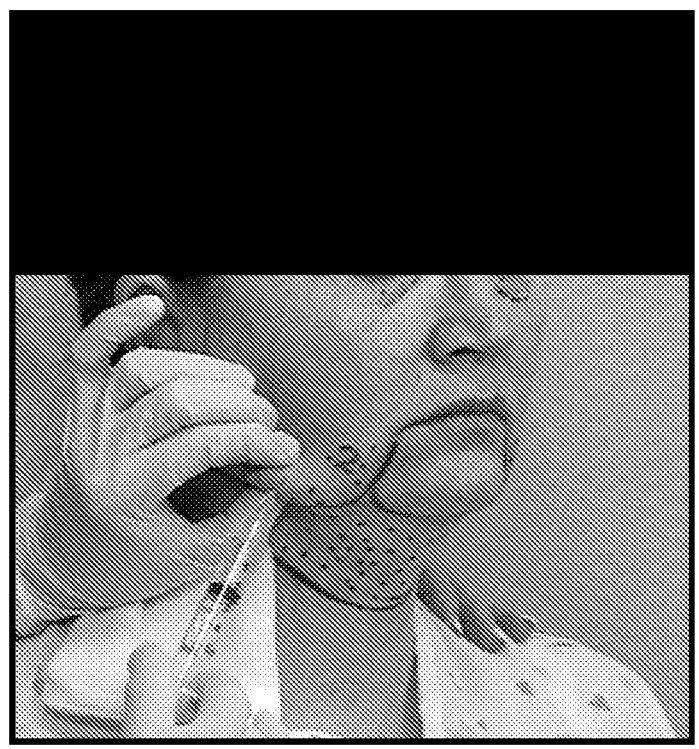
FIG. 10 shows a diagram of an injection pattern for basic level users of an injectable lipolytic composition.

The diagram in FIG. 10 shows an injection pattern for basic level users of an injectable lipolytic composition. This pattern presupposes some dispersion of the injectable composition. In the facial region, a grid or ruler was used to measure the distance between injection points.

In Palmer and Duncan's article on the standard of practice for injection lipolysis (Duncan D I, Palmer M: Fat reduction using phosphatidylcholine/sodium deoxycholate injections: standard of practice. Aesthetic Plast. Surg. 2008; 32: 858-72), these points were described as being 1 cm apart for facial regions, and 1.5 cm apart in body regions. Facial injections should be performed with a meso needle that is 6 mm long, in order to standardize the depth of injection. A dose of 0.2 to 0.4 cc of a 10 mg/ml product is the standard dose per pre-marked injection site in facial regions. In body regions, a dose of 0.4 to 0.5 cc of the same concentration would be used, and the grid pattern would show injection points 1.5 cm apart.

An alternative pattern would be a multi-level injection, using an under-the-skin type delivery. These would be performed from a single entry site, and would be executed in a ray-type distribution, similar to liposuction. The value of treating multiple levels of adiposity has been recently shown, so a better and more uniform response can be obtained with this method. Also, drugs with poor dispersion can be better delivered to the target tissue this way.

Example 5

This example reports exemplary compounds reported in Example 1. Over seventy compounds of the embodiments were tested for adipocytolysis, then for tissue preference. A consistent assay with multiplex information was a calcein/ethidium bromide assay that assesses cell viability and cell death simultaneously. Cell viability was checked using the Countess device. All plates were inoculated with 100 microliters of the appropriate cell types. A 6 well repeat was used to verify results. Cell types used included cultured human adult derived adipocytes, dermal fibroblasts, skeletal muscle cells, and endothelial cells (Cell Applications, Inc., San Diego, Calif.). Human peripheral nerve cells (Innoprot, Spain) were also used.

Compounds were formulated using a DMSO/PBS excipient. A 10 mg/ml concentration was used. One hundred microliters of test compound was inserted into 6 wells of 5 cell types, placed in adjacent rows. The plates were incubated for 4 hours. Indicator was added to each well, and plates were read at 45 minutes using a fluorescence spectrophotometer (Molecular Devices, Sunnyvale, Calif.).

Figure 11:
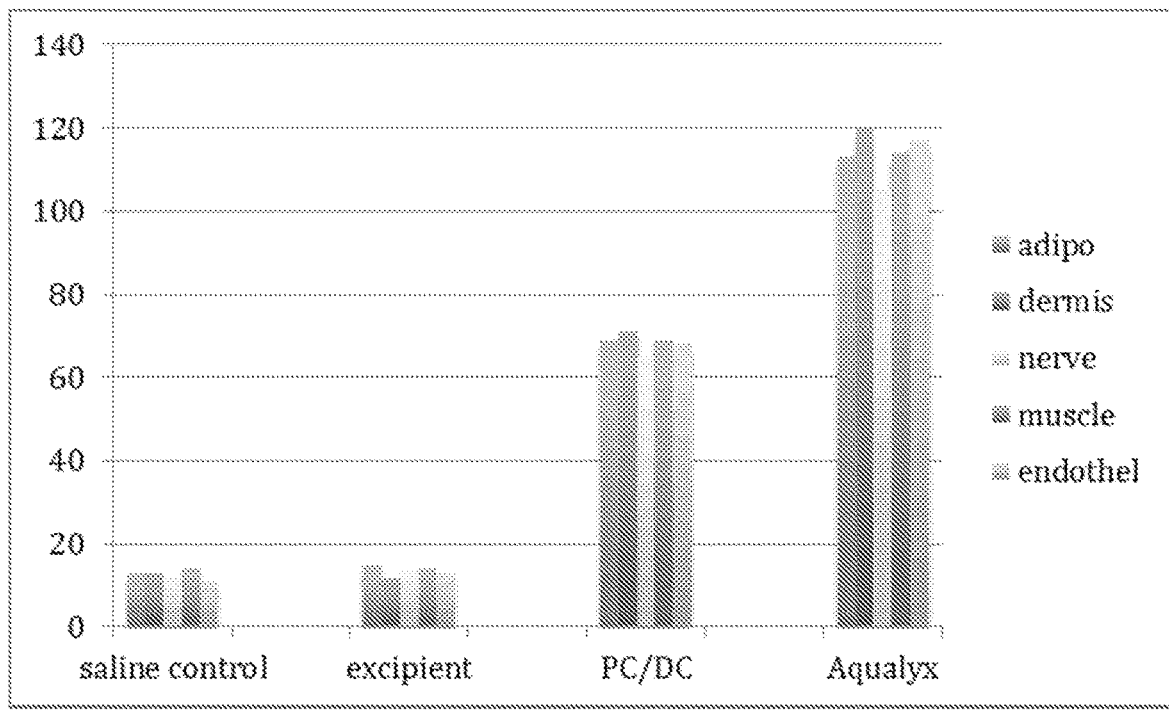
FIG. 11 shows the kill rate of adipocytes, dermal cells, nerve cells, muscle cells, and endothelial cells treated with saline, excipient, phosphatidylcholine plus deoxycholate, or Aqalyx.

FIG. 11 shows results for adipocytes, dermal cells, nerve cells, muscle cells, and endothelial cells for control compounds. Normal saline was a negative control. Excipient was DMSO/PBS excipient. Positive controls included phosphatidylcholine 25 mg/ml plus deoxycholate 12 mg/ml (PC/DC, MasterPharm, Richmond Hill, N.Y.), and Aqualyx®, a sodium deoxycholate in a lactose carrier (Marllor International, Italy). All the bars in FIG. 11 indicate kill rate (ethidium). The tissue preference assays in FIG. 11 were repeated three times, one month apart, to verify consistent findings. As shown in FIG. 11, the control compounds were indiscriminate for adipocytes, dermal cells, nerve cells, muscle cells, and endothelial cells.

Figure 12:
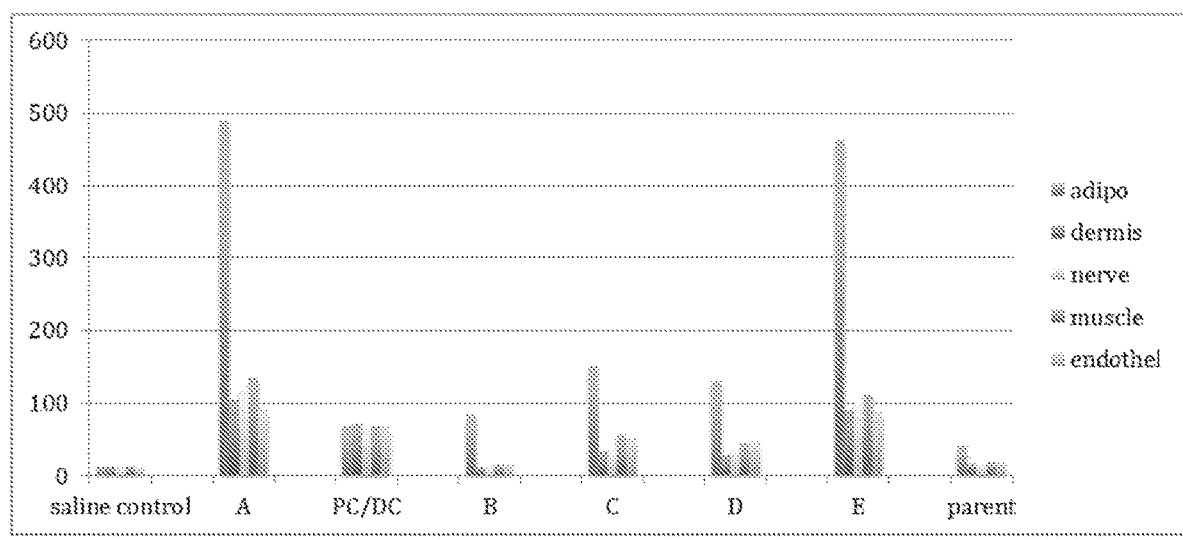
FIG. 12 shows the kill rate of adipocytes, dermal cells, nerve cells, muscle cells, and endothelial cells treated with test compounds A-E compared to Aqalyx, phosphatidylcholine plus deoxycholate, and saline controls.

FIG. 12 shows results for adipocytes, dermal cells, nerve cells, muscle cells, and endothelial cells for control compounds and test compounds. All the bars in FIG. 12 indicate kill rate (ethidium). As shown in FIG. 12, Compounds A, B, C, D, and E showed high specificity for adipocytes over dermal cells, nerve cells, muscle cells, and endothelial cells. PC/DC shows uniform cell death with all tissue types. The parent indole compound (Compound 33) showed about 50% tissue preference.

Figure 13:
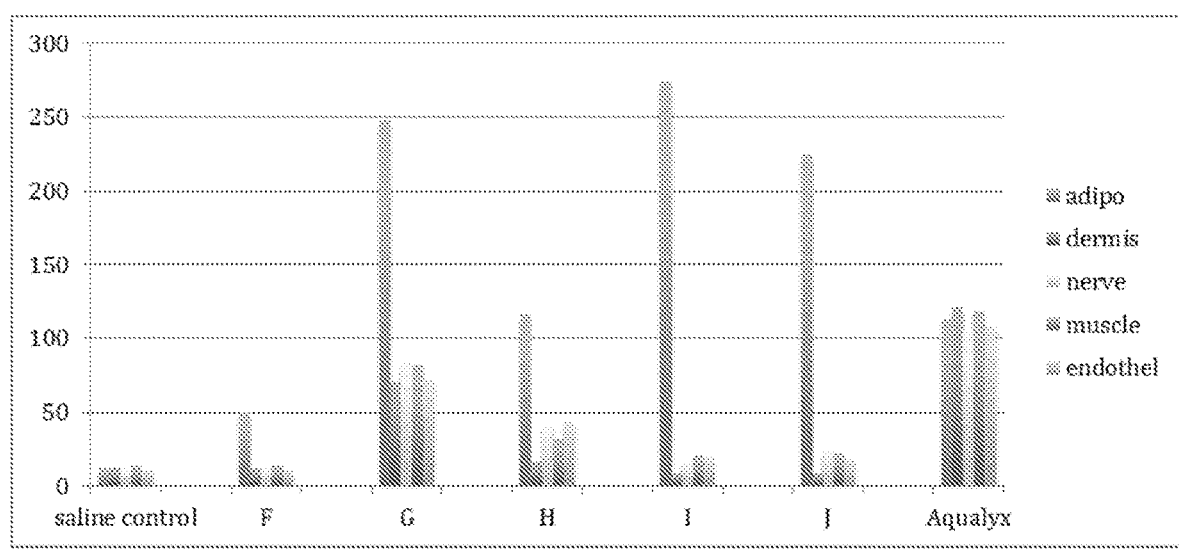
FIG. 13 shows the kill rate of adipocytes, dermal cells, nerve cells, muscle cells, and endothelial cells treated with test compounds F-J compared to Aqalyx, phosphatidylcholine plus deoxycholate, and saline controls.

FIG. 13 shows results for adipocytes, dermal cells, nerve cells, muscle cells, and endothelial cells for control compounds and test compounds. All the bars in FIG. 13 indicate kill rate (ethidium). As shown in FIG. 13, Compounds F, G, H, I, and J showed high specificity for adipocytes over dermal cells, nerve cells, muscle cells, and endothelial cells. There was no tissue preference for either control (saline and Aqualyx®).

Example 6

This example reports exemplary compounds reported in Example 1. A mouse study was performed to test compounds of the embodiments. Eight test compounds were injected. In addition to normal saline and compound diluent (DMSO plus excipients) (negative controls), positive controls included 1% sodium deoxycholate (DC, MasterPharm, Richmond Hill, N.Y.), phosphatidylcholine 25 mg/ml plus deoxycholate 12 mg/ml (PC/DC, PC25/DC 12, MasterPharm, Richmond Hill, N.Y.), and Aqualyx®, a sodium deoxycholate in a lactose carrier (Marllor International, Italy).

Seventy nude mice were chosen for a study of safety and efficacy of injectable lipolytic compounds. Human fat was harvested one hour prior to the injection procedure. 0.5 cc of fat was loaded into micro syringes. Engraftment took place under general anesthesia. Four weeks later, the fat pad size was measured and compounds injected precisely using a 6 mm meso needle in the center and 0.5 cm cephalad and caudad to the midpoint. Mice were sacrificed at one day, one week, two weeks and 4 weeks. One mouse died following injection. This same mouse exhibited SRP (sick rodent posture) following engraftment. Three mice developed SRP and were euthanized according to protocol.

Each fat pad was measured and weighed on the analytical balance at the time of sacrifice. Photos were taken and histology was performed. SEM was performed at two weeks and 4 weeks. Gross characteristics of the fat were documented.

At four weeks, clinical size reduction was just becoming visible with PC/DC and DC injectables. Visible and measurable fat reduction was noted with DC and three test compounds, although the number of mice with each compound sacrificed at 4 weeks could not give any statistically significant numbers. The two compounds that induced death or SRP were deleted, as clinical performance for either was not strong.

Details of injection of compounds into the mice and results are discussed below. Each mouse was given general anesthesia. Previous to injection of compounds, the fat pad was remeasured as not all fat takes as a graft. Mean graft take was 68%.

Size reduction after compound injection was measured against the measurement taken just previous to injection of compounds. The fat grafts migrated laterally in all but one case. Compound dose was calculated based on the average weight of each mouse and was based on the maximum safe dose of PC/DC. At 0.4 mg/gram, maximum dose was estimated to be 10 mg. Actual dose was 6 mg per mouse.

Three injections were performed and were perpendicularly given to a depth of 0.6 cm using a 30 gauge meso needle, spaced 0.5 cm apart. Eight test compounds were injected. Negative control was saline and the DMSO excipient. Two positive controls, Aqualyx® and PC25/DC12, were injected. Five mice exhibited small excoriations at the injection site. All had disappeared within one day.

Mice were given a special antibiotic diet. No mouse became infected. After the first 24 hours, all recovered well and seemed to ignore the fat pads. Sacrifice of mice took place as schedule. A limited postmortem at 24 hours showed no apparent systemic effects.

Figure 14:
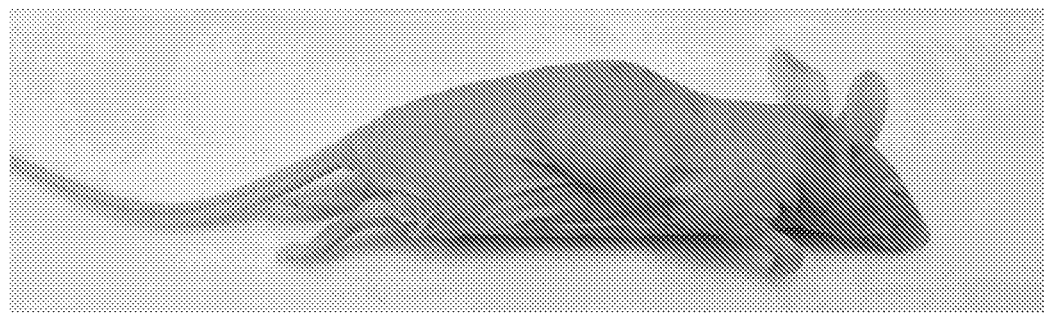
FIG. 14 shows the effect of a sample compound on a mouse fat pad graft one day after injection.

FIG. 14 shows a sample mouse at one day postinjection. No effect from the compound was noted. Neovascularization of the graft was visible beneath the thin skin of this mouse. No effect on adjacent tissue nor vital organs was noted.

Figure 15:
FIG. 15 shows the effect of Compound B on a mouse fat pad graft one week after injection.

FIG. 15 shows a mouse, injected with Compound B, which had a lobulated graft. The most cephalad pad was not injected. The central pad was injected with 0.1 cc or 1 mg of compound. The most caudal fat pad was injected with 0.2 cc or 2 mg of compound. As early as one week, fat necrosis had been induced with Compound B. FIG. 15 shows that fat necrosis occurred prevalently on the most caudal pad and to a lesser degree on the central pad.

Figure 16:
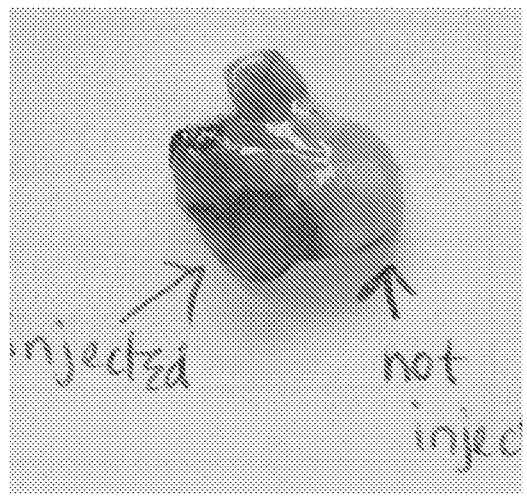
FIG. 16 shows the effect of deoxycholate on a mouse fat pad graft one day after injection.

FIG. 16 shows deoxycholate injected fat pad at Day 1. Immediate necrosis was apparent in the injected segment. The lack of dispersion was made clear in this specimen.

Figure 17:
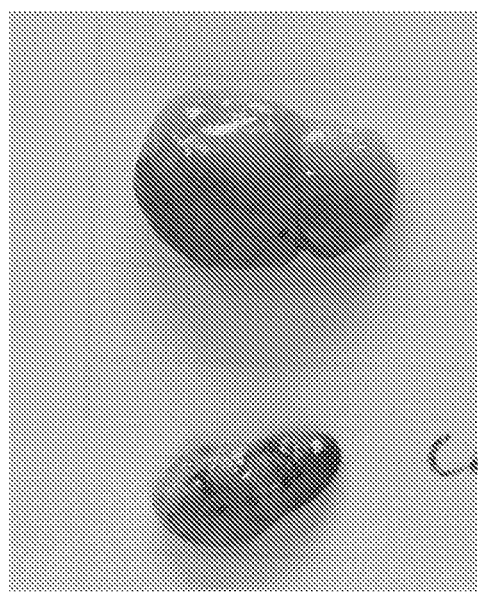
FIG. 17 shows the effect of Compound D (above) compared to excipient control (below) on a mouse fat pad graft one week after injection.

FIG. 17 shows gross appearance of Compound D (above) as compared to excipient control (below), at one week postinjection. Tested compounds of the embodiments appeared to induce some type of fat reaction. Visible gross changes included discoloration as early as one week. Some liquefaction was seen at two weeks. A soft granular appearance with size reduction was noted at 4 weeks.

Figure 18:
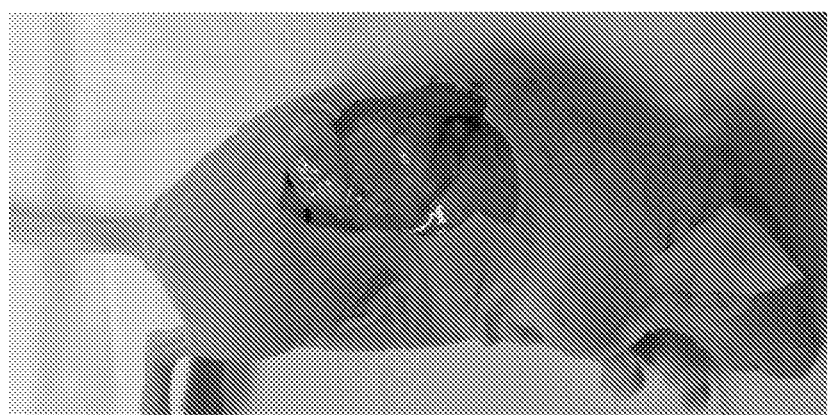
FIG. 18 shows the effect of Compound H on a mouse fat pad graft one week after injection.

FIG. 18 shows a mouse at one week postinjection. The mouse was treated with Compound H. There was discoloration and textural changes in the fat pad after injection of Compound H, as shown in FIG. 18.

Figure 19:
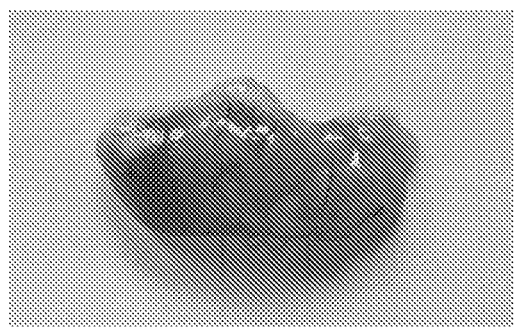
FIG. 19 shows the effect of Compound I on a mouse fat pad graft two weeks after injection.
Figure 20:
FIG. 20 shows the effect of Compound I on a fat pad graft four weeks after injection.

FIG. 19 shows the effect of Compound I at two weeks. There is some liquefaction and textural change. Definite fat necrosis was present. FIG. 20 shows the effect of Compound I at four weeks. Dispersion was good; the entire fat pad was been affected. A measured 33% reduction in fat pad size was noted. Compound I showed good results and is an excellent test compound in this study.

Figure 21:
FIG. 21 shows the effect of phosphatidylcholine plus deoxycholate on a mouse fat pad graft four weeks after injection.

FIG. 21 shows PC/DC treated fat pad at 4 weeks. There was almost no visible change from its original condition.

A clinical outcome view was taken to test compounds for fat killing potential. A final arbiter of success is visible reduction in the size of the fat pad following treatment. This endpoint is best observed by clinicians.

Example 7

Scanning electron microscopy (SEM) can provide images of a sample's topography and composition. SEM was performed on various adipose cells.

This example reports exemplary compounds reported in Example 1.

Figure 22:
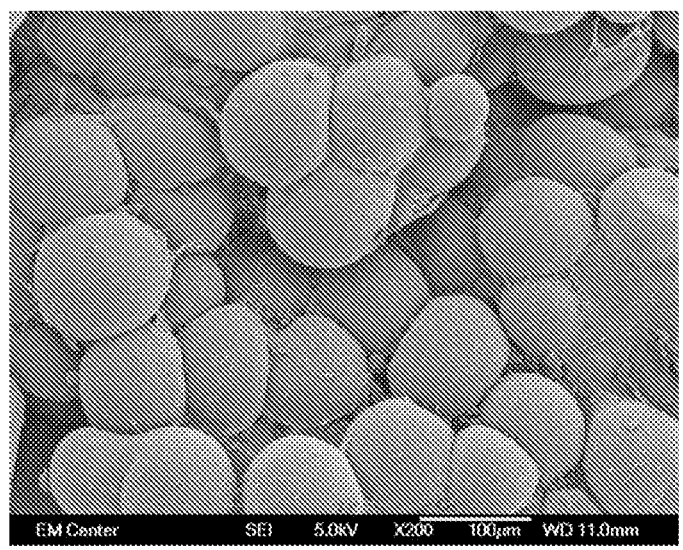
FIG. 22 shows a scanning electron micrograph of the effect of saline control on fat cells.
Figure 23:
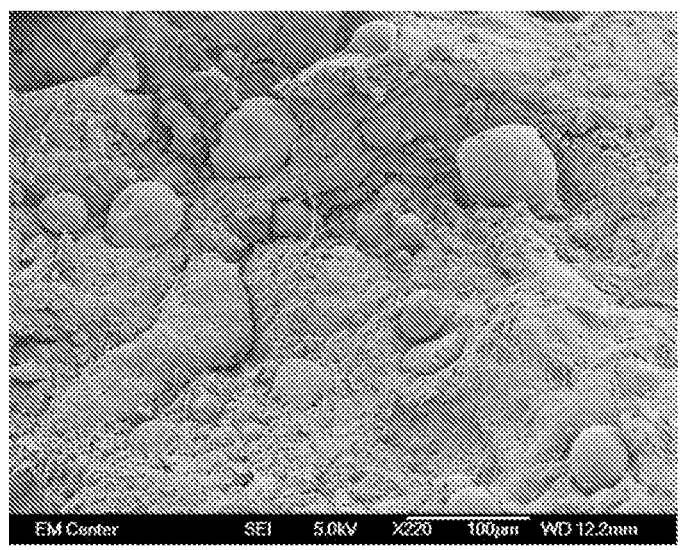
FIG. 23 shows a scanning electron micrograph of the effect of deoxycholate on fat cells.

FIG. 22 shows the appearance of normal fat cells with saline control. There was a very thin, fibrous "netting" that holds the cells together. As shown in FIG. 23, the fibrous scar response generated by deoxycholate was massive. There are very few live cells left in this tissue segment; most was fibrous scar response. An ideal response would be either an apoptotic response with little inflammation in cases where only fat reduction is needed, or a combination of fat reduction and moderate inflammation when tissue tightening is the desired response. The compounds of the embodiments can generate these desired responses.

Figure 24:
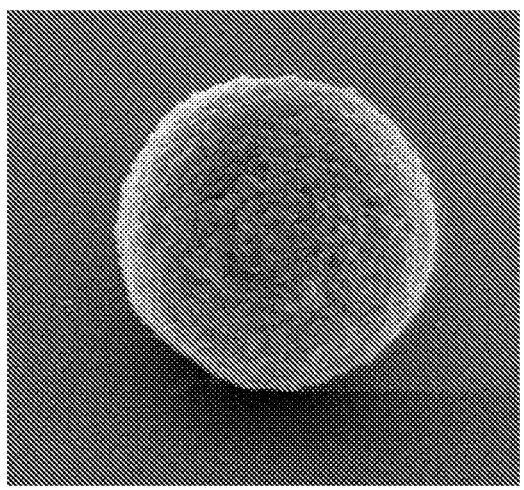
FIG. 24 shows a scanning electron micrograph of an untreated, cultured adipocyte.
Figure 25:
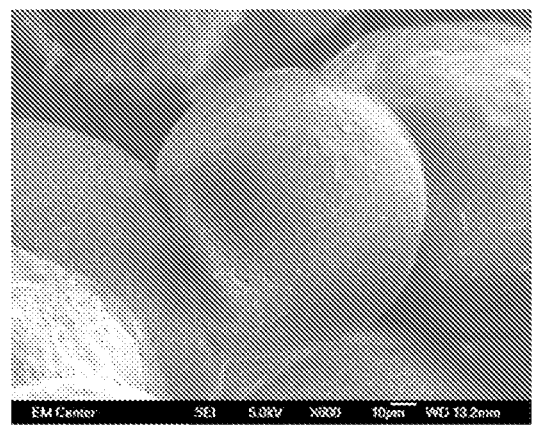
FIG. 25 shows a scanning electron micrograph of an intact adipocyte in vivo.

FIG. 24 shows SEM of an untreated cultured adipocyte. The physical characteristics of adipose cells were easily identified when cultured cells are treated. Intact adipocytes were round, with a mean diameter of about 100 microns. There was great variability in the size of adipocytes, which can range from 30 microns to over 200 microns. The surface of the cell membrane was not slick and smooth. FIG. 25 shows intact adipocytes in vivo. These were not perfectly round. Their shape was affected by its neighbors.

Figure 26:
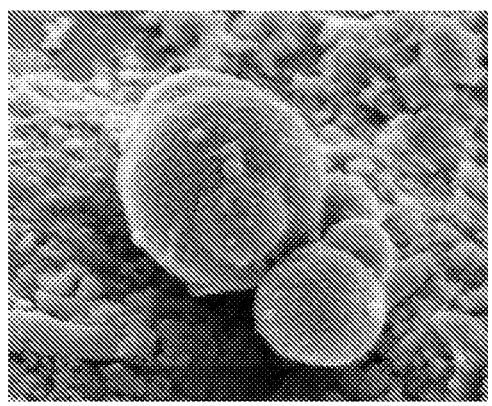
FIG. 26 shows a scanning electron micrograph of cultured adipocytes treated with phosphatidylcholine plus deoxycholate four hours after treatment.

FIG. 26 shows SEM of cultured adipocytes treated with PC/DC at four hours. There was blebbing, a hallmark of apoptosis. Bleb is an irregular bulge in the plasma membrane of a cell. Cell wall injuries can have two outcomes. If a large enough defect is created, the cell cannot repair itself and it undergoes necrosis, with the creation of lysozymes and egress of the cell contents. Clinically, this will result in swelling and inflammation of the treatment region. Smaller blebs may cause poration, which can induce programmed cell death.

Figure 27:
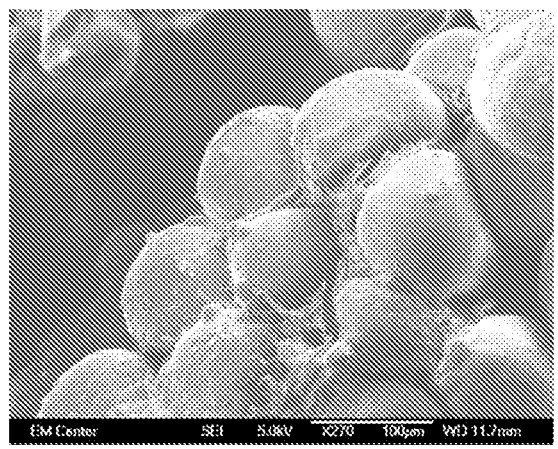
FIG. 27 shows a scanning electron micrograph of adipocytes treated in vivo with phosphatidylcholine plus deoxycholate four weeks after treatment.

FIG. 27 shows cultured adipocytes treated with PC/DC in vivo at 4 weeks. Blebbing was a prominent feature. Inflammation was denoted by the formation of a fibrous coating of the cells.

Figure 28:
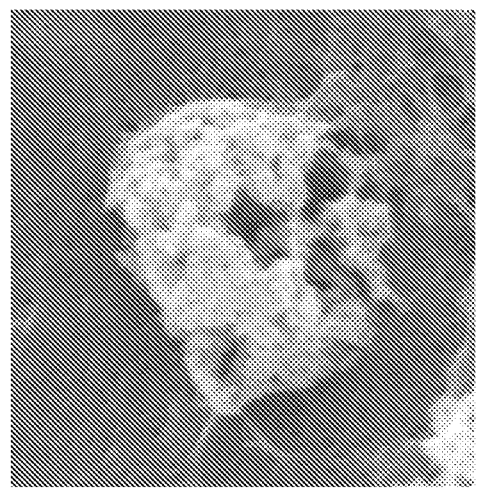
FIG. 28 shows a scanning electron micrograph of a single cultured adipocyte treated with deoxycholate after four hours of treatment.

FIG. 28 shows the effect of deoxycholate on a single cultured adipocyte after four hour incubation. The cell membrane has been disrupted at multiple sites.

Figure 29:
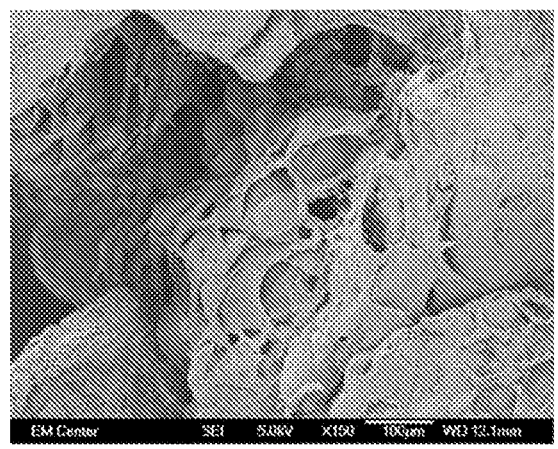
FIG. 29 shows a scanning electron micrograph of tissue treated with deoxycholate four weeks after treatment.

FIG. 29 shows a barren landscape of tissue treated with deoxycholate at 4 weeks. There were very few living adipocytes. Fibrous ingrowth was extensive. These SEM findings correlated with the histology seen in deoxycholate treated tissue. The inflammatory reaction was intense; all cells within millimeters of the treatment region died an acute necrotic death. This led to extensive scarring such that the "soft" tissue is no longer soft.

Figure 30:
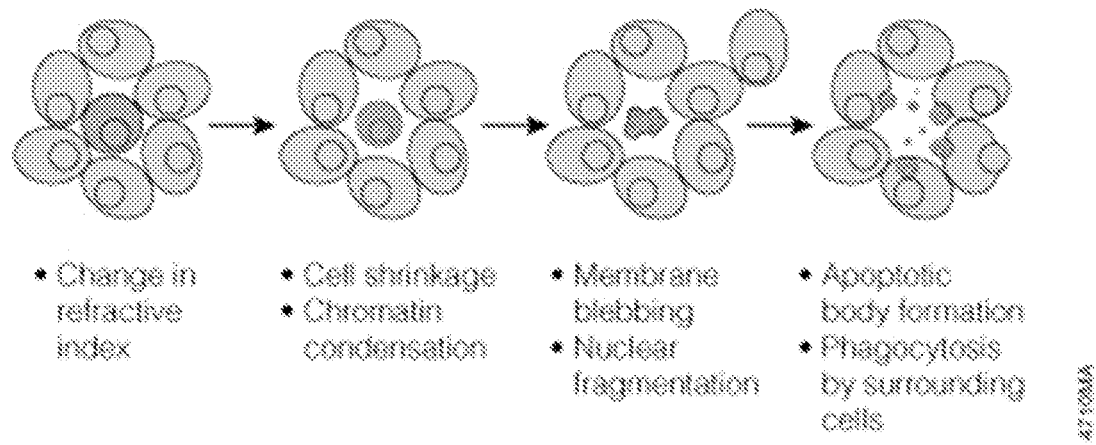
FIG. 30 shows a mechanism of action for adipocyte cell death.
Figure 31:
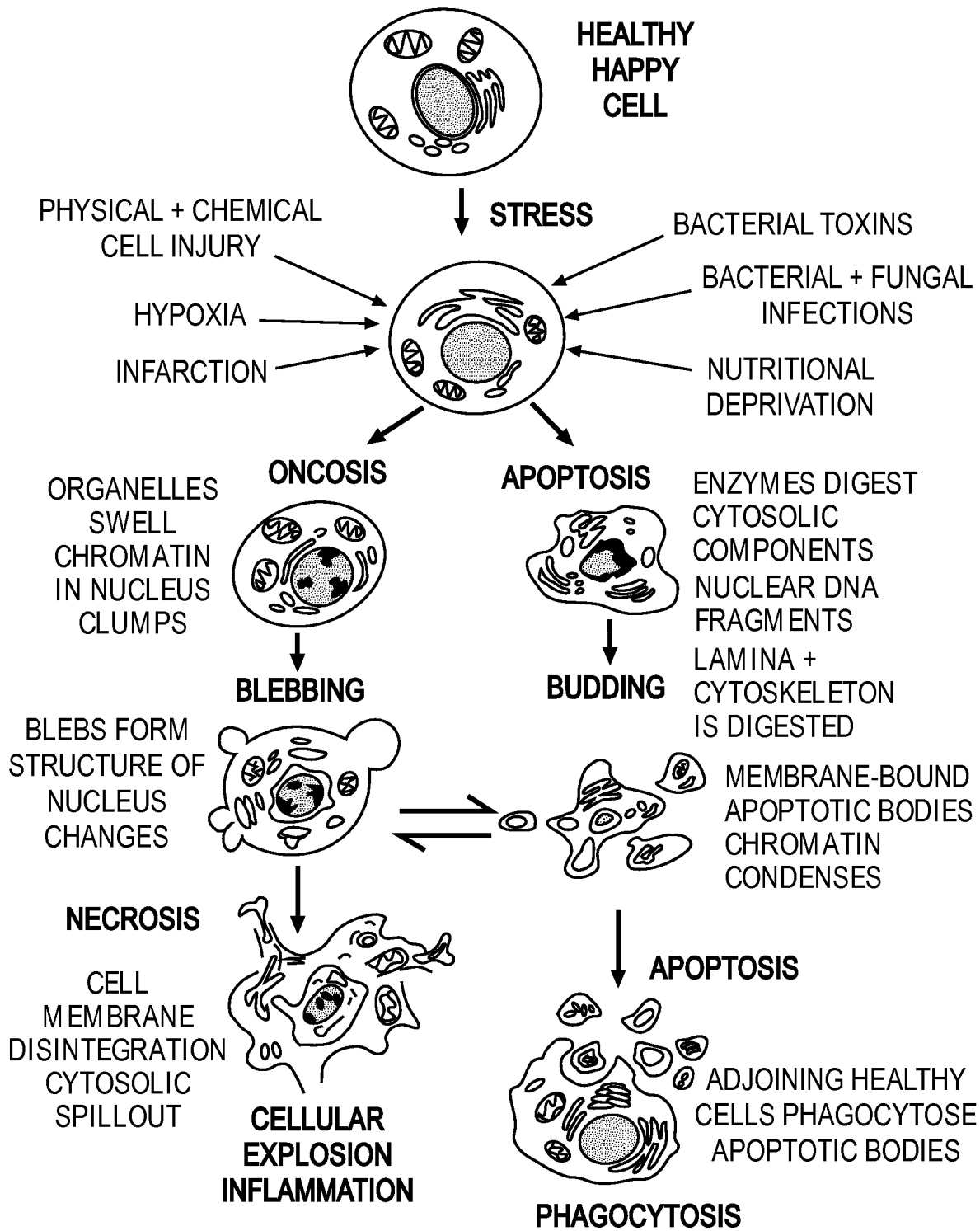
FIG. 31 shows a mechanism of action for adipocyte cell death.

Majno's description of the process of adipocyte cell death is either apoptosis or necrosis. (Majno et al., "Apoptosis, oncosis, and necrosis. An overview of cell death," Am J. Pathol. 1995 January; 146(1): 3-15.) FIGS. 30-31 shows diagrams of a mechanism of action of Majno.

The mechanism of action of injected sodium deoxycholate, is the causation of immediate cell necrosis in adipoctytes localized to a narrow radius of the injection. Phosphatidylcholine/deoxycholate (PC/DC) was much slower to act. PC/DC induced early apoptosis followed by a gradual, more diffuse induction of cell lysis over a period of 4 to 6 weeks.

However, the compounds of embodiments can be shown to follow a different mechanism of action. The mechanism of action includes poration and effusion. The mechanism of action of lipolytic indole compounds is a new one called chemoporation. SEM micrographs of the mechanism are shown in FIGS. 37-41. A compound of the embodiments was injected into the subcutaneous fat using either a depot or ray type serially repeated pattern. No cell necrosis took place. As the compounds of the embodiments are tissue preferential, no other tissues are affected. The reason no other tissues were affected is because this mechanism of action works for fat cells only. An initial response, seen as early as four hours post-treatment, was poration of the treated cells. Tiny openings in the adipocyte membrane became more prominent, and the cell wall surface began to appear "holey." (FIG. 37) Then, for example, hundreds, then thousands of lipid droplets collected immediately under the cell membrane. As other cells do not have intracellular lipid droplets, this mechanism does not affect them. (FIG. 38) As the pores became larger, lipid droplets diffused through the cell membrane and became extracellular. (FIG. 39) With time, thousands of lipid droplets collected on the surface of the cell wall. (FIG. 40) There was visible "crumpling" or loss of internal cell volume. (FIG. 41) Once a critical loss of volume occurred, the cell died. The steps in this process following drug injection or other type of application included poration, lipid droplet formation and collection just under the cell wall, diffusion through the cell membrane, exteriorization, and cell implosion with subsequent death.

FIGS. 32-36 below show examples of a mechanism of action with SEM of poration and effusion. FIGS. 37-41 below show examples of a mechanism of action with SEM of poration and effusion in close-up views.

Figure 32:
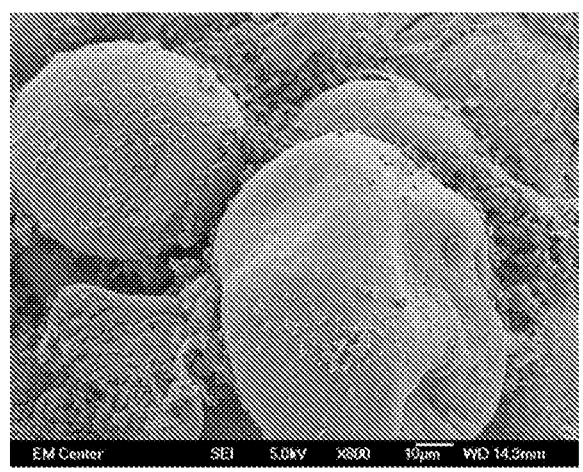
FIG. 32 shows a scanning electron micrograph of adipocytes treated with Compound A in vivo four weeks after treatment.

FIG. 32 shows the effect of Compound A on adipocytes in vivo at 4 weeks posttreatment. The cells underwent a process of lipolysis in which thousands of lipid droplets coalesce just under the cell membrane. Poration occurred, and the lipid droplets escaped. When cell volume depletion becomes critical, the cell signals its own death.

Figure 33:
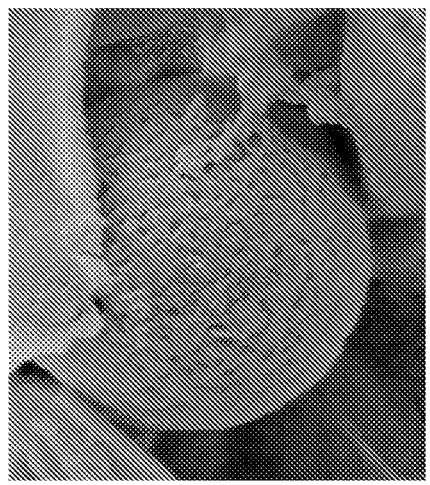
FIG. 33 shows a scanning electron micrograph of the effect of Compound B on a cultured adipocyte.

FIG. 33 shows poration of a cultured adipocyte caused by Compound B.

Figure 34:
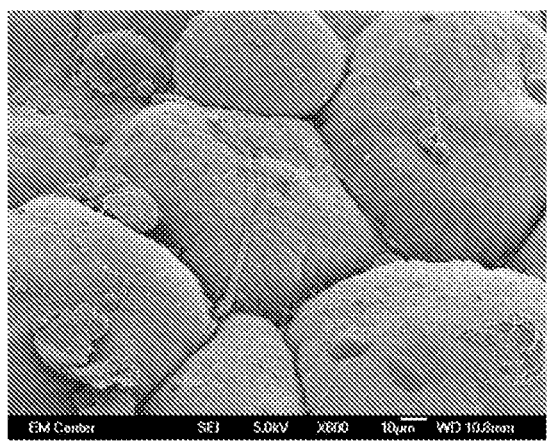
FIG. 34 shows a scanning electron micrograph of adipocytes treated with Compound B in vivo four weeks after treatment.

FIG. 34 shows the effect of Compound B at 4 weeks. There were platelets on cell at the lower right. Compound B elicited a vascular response, with platelets and white blood cells (WBCs) within the treatment region. There was also a lack of extensive scarring.

Figure 35:
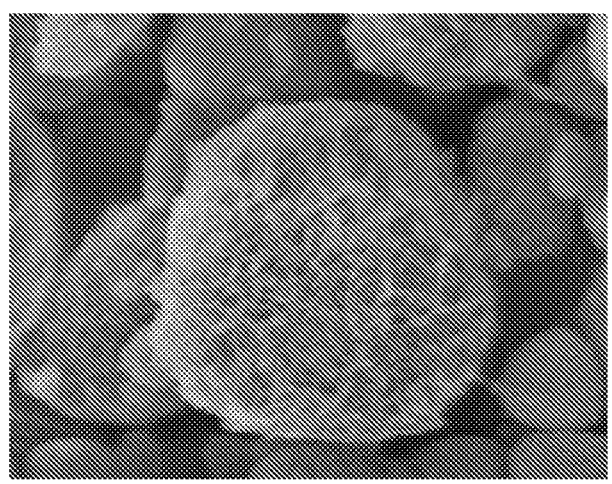
FIG. 35 shows a scanning electron micrograph of adipocytes treated with Compound C in vivo after four hours of treatment.

FIG. 35 shows severe spongiform poration of an isolated cultured adipocyte after a 4 hour exposure to Compound C. This type of pyroptotic cell death caused less inflammation than deoxycholate's necrotic process.

Figure 36:
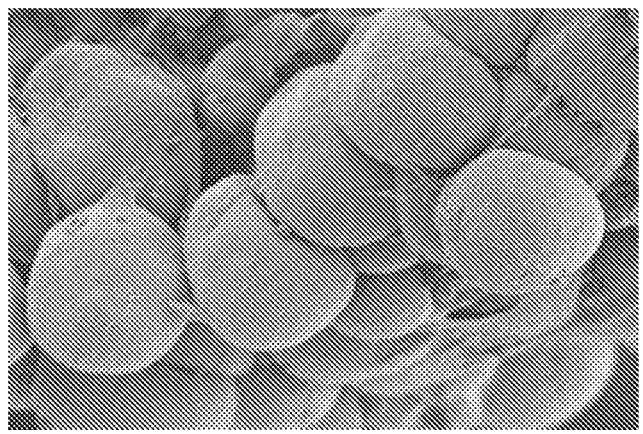
FIG. 36 shows a scanning electron micrograph of adipocytes treated with DMSO excipient in vivo four weeks after treatment.

FIG. 36 show a negative control with the effect of DMSO excipient at 4 weeks. There were cells that appear intact with slight fibrous adhesions.

Figure 37:
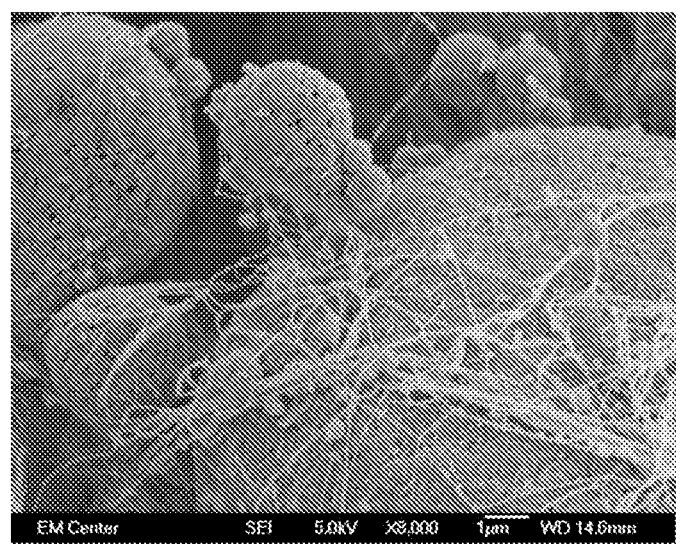
FIG. 37 shows a scanning electron micrograph of an adipocyte undergoing poration.
Figure 38:
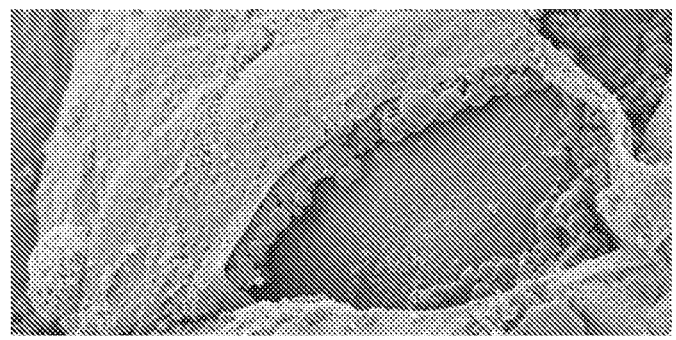
FIG. 38 shows a scanning electron micrograph of an adipocyte with lipid droplets underneath its cell membrane.
Figure 39:
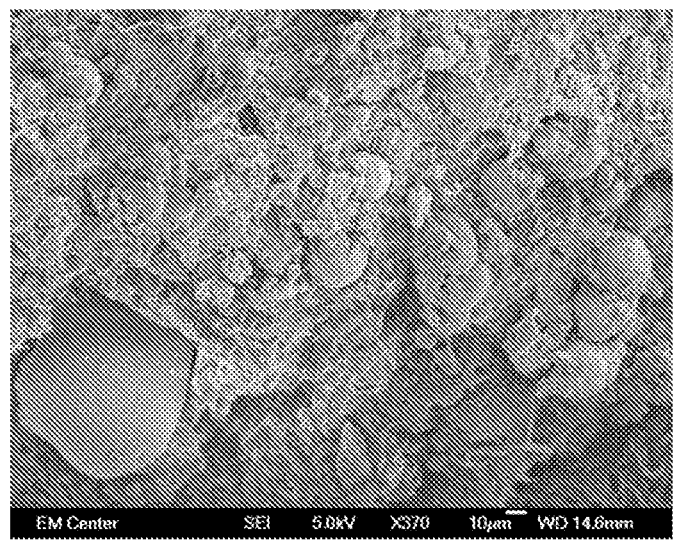
FIG. 39 shows a scanning electron micrograph of an adipocyte undergoing effusion.
Figure 40:
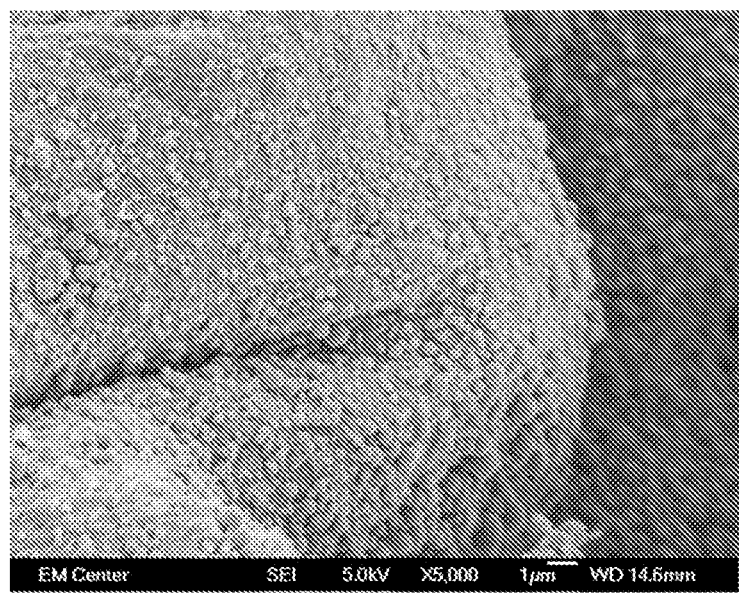
FIG. 40 shows a scanning electron micrograph of an adipocyte treated with Compound J four weeks after treatment.
Figure 41:
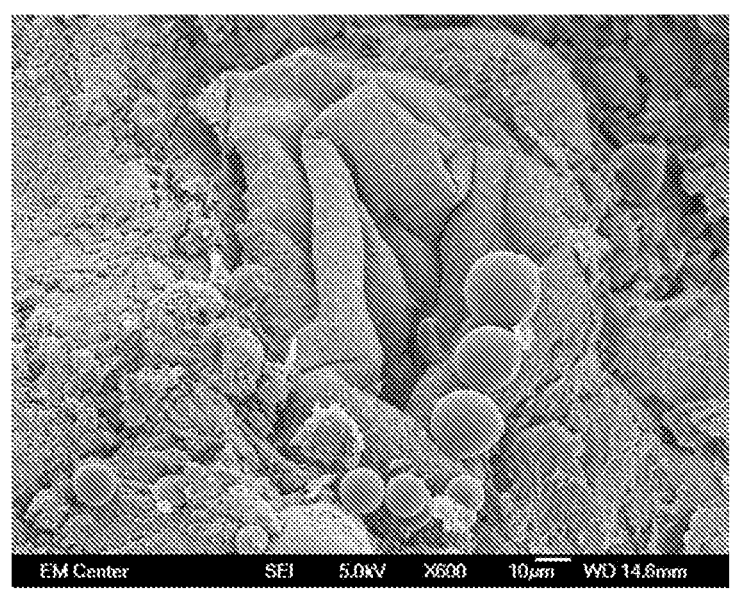
FIG. 41 shows a scanning electron micrograph of an adipocyte undergoing cell death.

As discussed above, FIGS. 37-41 show examples of a mechanism of action with an SEM of poration and effusion in close-up views. FIG. 37 shows SEM with a close-up view of poration of an adipocyte. FIG. 38 shows a collection of lipid droplets underneath the cell membrane. FIG. 39 shows an SEM with a close-up view of effusion of an adipocyte. This was a single cell. There were lipid droplets coming out of the pores. FIG. 40 shows a close-up view of a cell treated with Compound J at four weeks. There was extrusion of thousands of lipid droplets. FIG. 41 shows a close-up view of adipocyte death. With the tested compounds of the embodiments, the gradual process over a four week period took longer than deoxycholate's reaction, which was instantaneous. The tested compounds of the embodiments worked more quickly than PC/DC. Tissue treated with PC/DC was just beginning to react at four weeks.

Figure 42:
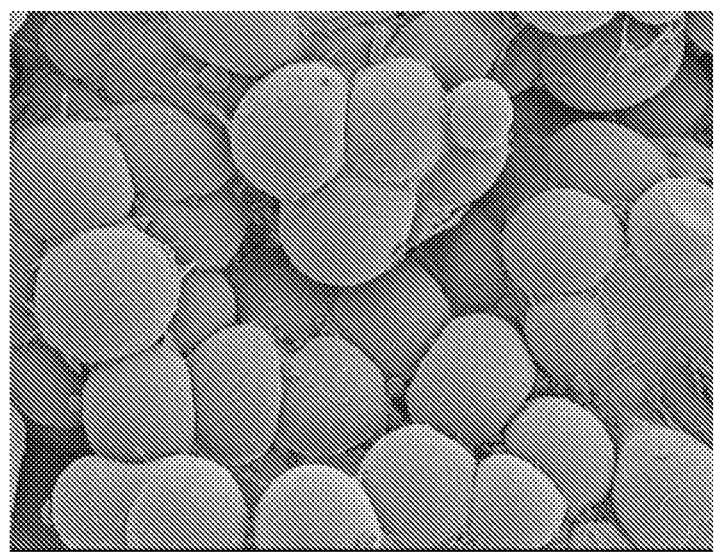
FIG. 42 shows a scanning electron micrograph of adipocytes treated with saline in vivo four weeks after treatment.
Figure 43:
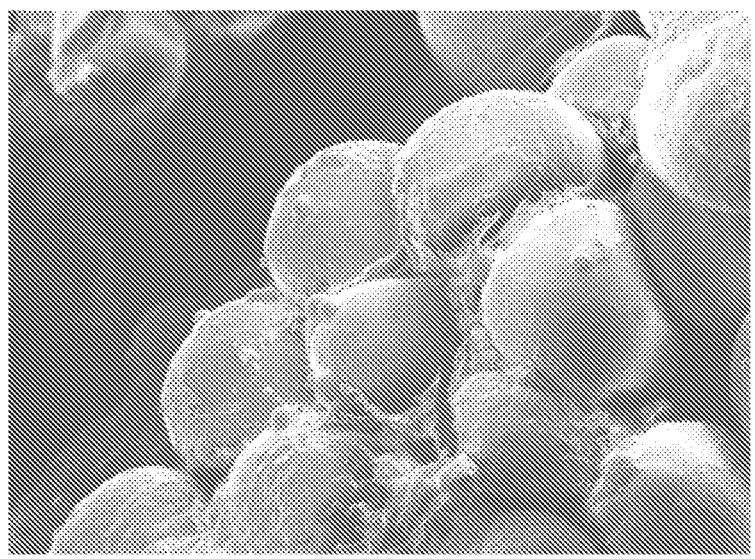
FIG. 43 shows a scanning electron micrograph of adipocytes treated with phosphatidyl choline and deoxycholate in vivo four weeks after treatment.
Figure 44:
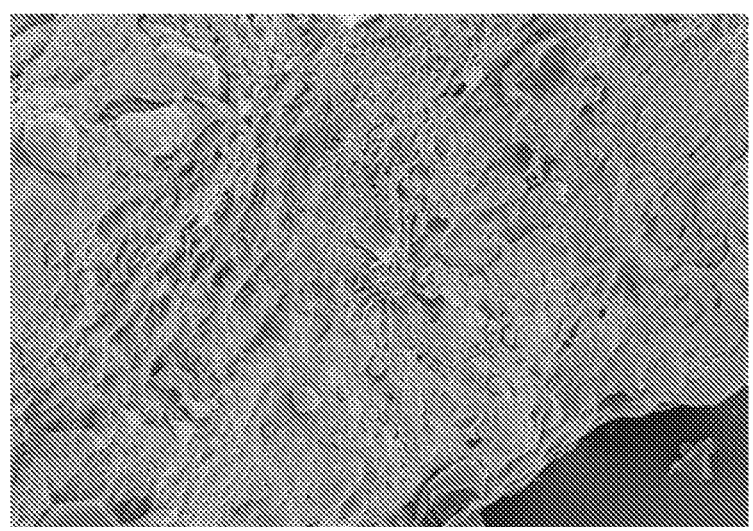
FIG. 44 shows a scanning electron micrograph of adipocytes treated with deoxycholate in vivo four weeks after treatment.
Figure 45:
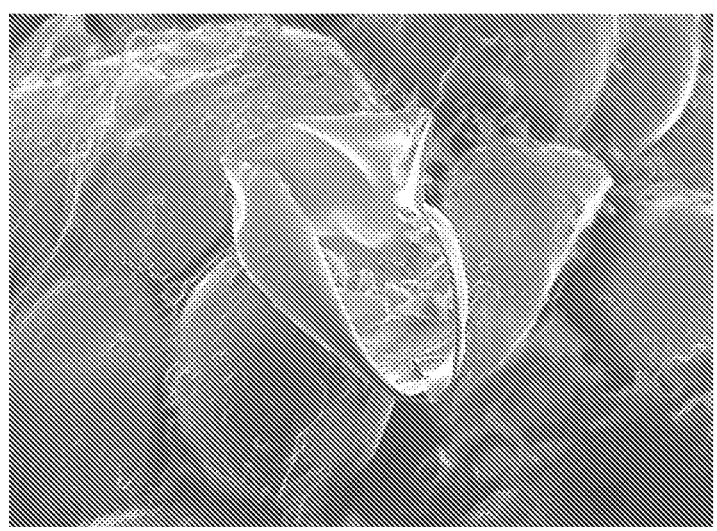
FIG. 45 shows a scanning electron micrograph of adipocytes treated with Compound J four weeks after treatment.

FIGS. 42-45 show comparison of the effect of Compound J with control compounds. FIG. 42 shows tissue injected with saline at four weeks. Cell sizes vary. The fibroseptal network is apparent. FIG. 43 shows SEM of tissue treated with PC/DC at four weeks. There is a blebbing mild fibrous reaction. The cells are still intact. FIG. 44 shows tissue treated with deoxycholate at four weeks. Massive fibrous replacement of normal tissue is apparent. FIG. 45 shows tissue treated with Compound J at four weeks. There are lipid droplets and a single lysed cell. Fibrous response with Compound J is modest.

Figure 46:
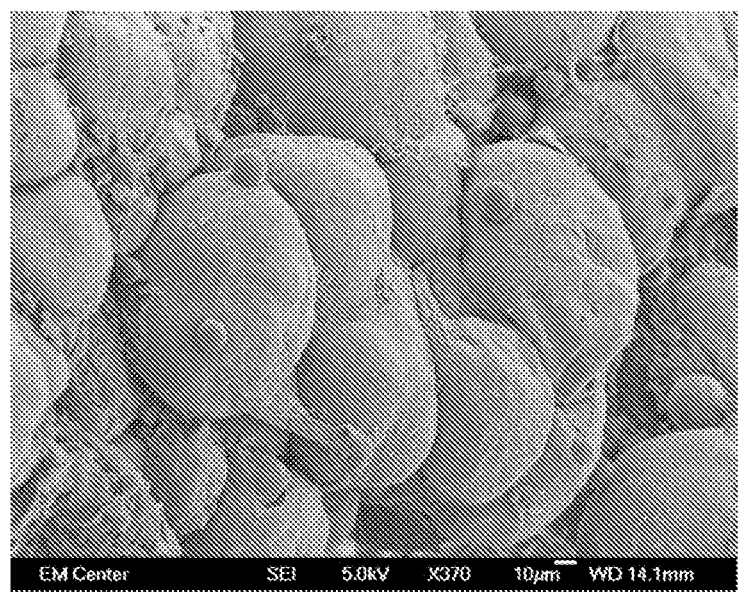
FIG. 46 shows a scanning electron micrograph of human fat treated with Compound D four weeks after treatment.

FIGS. 46-50 show the effects of tested compounds. FIG. 46 shows the effect of Compound D at 4 weeks following injection into human fat. This effect was similar to, but more profound than the effect of PC/DC. There was collapse of cell volume with round exteriorized lipid droplets. There were also lumpy shapes just under the cell membrane. These were hundreds of lipid droplets waiting to escape.

Figure 47:
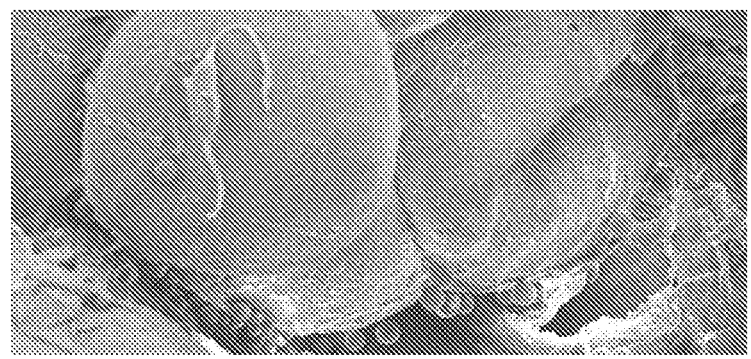
FIG. 47 shows a scanning electron micrograph of adipocytes treated with Compound E in vivo, four weeks after treatment.

FIG. 47 shows the effect of Compound E in vivo after 4 weeks. There are extracellular lipid droplets, and folding of a dying adipocyte. A disrupted cell is noted in the lower right of the figure. Some fibrous response is noted.

Figure 48:
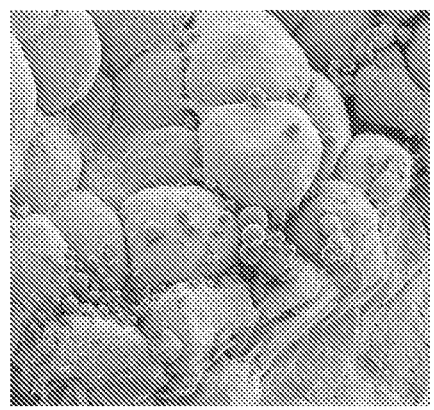
FIG. 48 shows a scanning electron micrograph of adipocytes treated with Compound I in vivo, four weeks after treatment.

FIG. 48 shows tissue treated with Compound I at 4 weeks. There were lipid droplets that have discharged through the cell wall. This mechanism was characteristic of the compounds of the embodiments.

Figure 49:
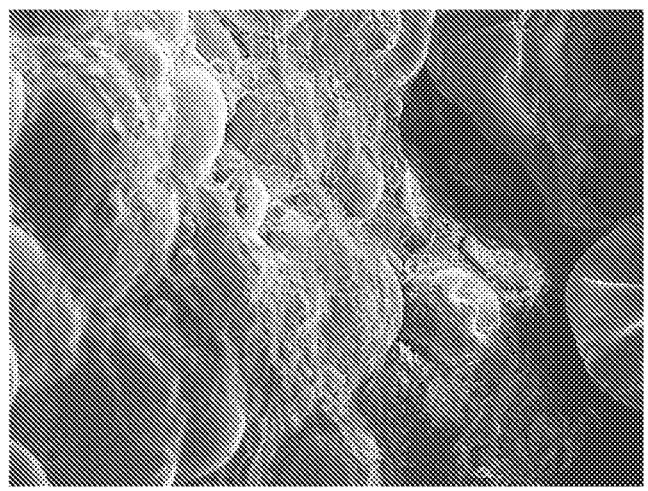
FIG. 49 shows a scanning electron micrograph of adipocytes treated with Compound H four weeks after treatment.

FIG. 49 shows the effect of Compound H at four weeks. There were crumpled cells, exteriorized lipid droplets, and more fibrous response than other tested compounds.

Figure 50:
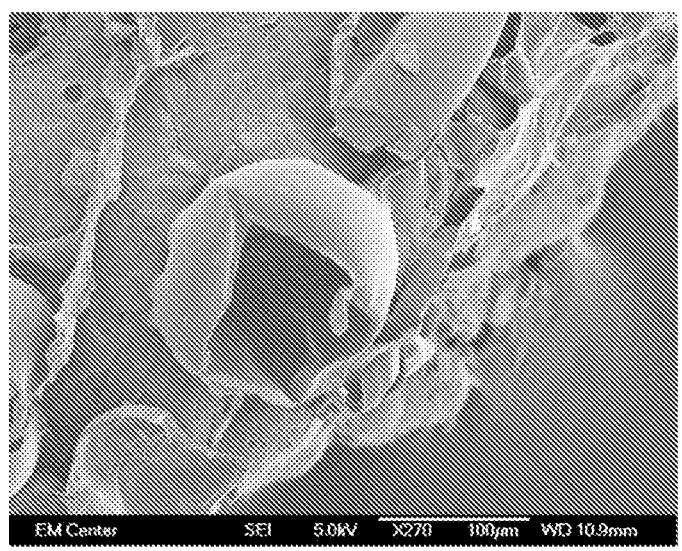
FIG. 50 shows a scanning electron micrograph of adipocytes treated with Compound I four hours after treatment.

FIG. 50 shows the effect on cultured cells that were treated with Compound I for four hours. Compound I induced an array of response including some cell lysis.

As shown in the figures, the steps in the adipocyte killing process appeared to be initial poration followed by collection of the lipid droplets under the cell membrane. The small pores became larger, and the lipid droplets underwent effusion. The cells lost volume and looked crumpled. Once a critical mass of volume was lost, cell signaling induced death.

The invention claimed is:

1. A method for non-surgical reduction or removal of one or more localized fat deposits in a subject having localized fat accumulation comprising administering to a target site in the fat deposit a compound of Formula (I-1), Formula (I-2), or Formula (I-3), wherein Formula (I-1) is represented by:

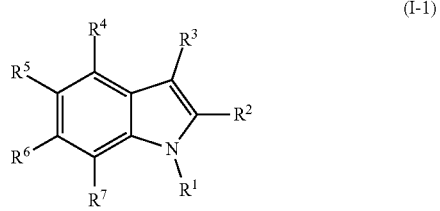

(I-1)

wherein
$R^1$ is hydrogen or $C_{1-6}$ alkyl;
$R^4$, $R^5$, $R^6$, and $R^7$ are independently selected from hydrogen, $C_{1-6}$alkyl, $C_{1-6}$alkoxy, halogen, and —OCH$_2$C$_6$H$_5$;
$R^2$ and $R^3$, together with the atoms they attach to, form

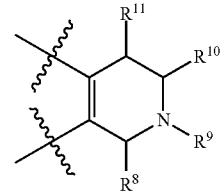

wherein $R^8$, $R^{10}$, and $R^{11}$ are independently selected from hydrogen, halogen, —(CH$_2$)$_x$—C(O)—OC$_{1-6}$ alkyl, —(CH$_2$)$_x$OH, —(CH$_2$)$_x$—CN, —OCH$_2$C$_6$H$_5$, —OCOCH$_3$, —(CH$_2$)$_x$—CONH$_2$, —CHO, —(CH$_2$)$_x$—COOH, —(CH$_2$)$_y$—CO—COOH, —(CH$_2$)$_y$—C(H)(OH)—COOH, phenyl, and substituted phenyl; wherein the substituted phenyl is substituted with 1-4 substituents selected from hydroxyl, $C_{1-6}$alkoxy, and $C_{1-6}$alkyl;
$R^9$ is hydrogen or $C_{1-6}$ alkyl;
x is a number from zero to six; and
y is zero;
or a pharmaceutically acceptable salt thereof;
Formula (I-2) is represented by:

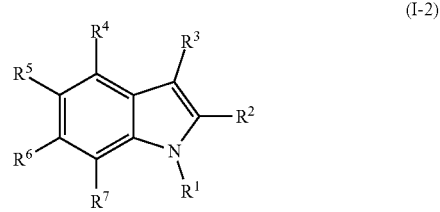

(I-2)

wherein
$R^1$ is hydrogen or $C_{1-6}$ alkyl;
$R^2$ and $R^3$ are independently hydrogen or $C_{1-6}$ alkyl;
$R^4$, $R^5$, $R^6$, and $R^7$ are independently selected from hydrogen, $C_{1-6}$alkyl, $C_{1-6}$alkoxy, —OCH$_2$C$_6$H$_5$, halogen, —CHO, and —(CH$_2$)$_x$—COOH; and
x is a number from zero to six;
or a pharmaceutically acceptable salt thereof;
provided that at least one of $R^4$, $R^5$, $R^6$, and $R^7$ is —CHO or —(CH$_2$)$_x$—COOH; and
Formula (I-3) is represented by:

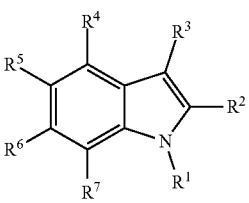

(I-3)

wherein
$R^1$ is hydrogen or $C_{1-6}$ alkyl;
$R^2$ is hydrogen or $C_{1-6}$ alkyl;

$R^3$ is —$(CH_2)_x$—COOH;
$R^4$, $R^5$, $R^6$, and $R^7$ are independently selected from hydrogen, $C_{1-6}$alkyl, $C_{1-6}$alkoxy, halogen, —$(CH_2)_x$—OH, and —$OCH_2C_6H_5$; and
x is a number from zero to six;
or a pharmaceutically acceptable salt thereof.

2. A method for reducing a subcutaneous fat deposit in a subject having subcutaneous fat deposit comprising administering to a target site in the subcutaneous fat deposit a compound of formula (I-1), formula (I-2), of formula (I-3), wherein formula (I-1) is represented by:

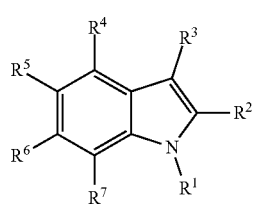

(I-1)

wherein
$R^1$ is hydrogen or $C_{1-6}$ alkyl;
$R^4$, $R^5$, $R^6$, and $R^7$ are independently selected from hydrogen, $C_{1-6}$alkyl, $C_{1-6}$alkoxy, halogen, and —$OCH_2C_6H_5$;
$R^2$ and $R^3$, together with the atoms they attach to, form

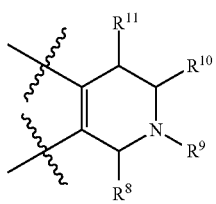

wherein $R^8$, $R^{10}$, and $R^{11}$ are independently selected from hydrogen, halogen, —$(CH_2)_x$—C(O)—$OC_{1-6}$ alkyl, —$(CH_2)_x$—OH, —$(CH_2)_x$—CN, —$OCH_2C_6H_5$, —$OCOCH_3$, —$(CH_2)_x$—$CONH_2$, —CHO, —$(CH_2)_x$—COOH, —$(CH_2)_y$—CO—COOH, —$(CH_2)_y$—C(H)(OH)—COOH, phenyl, and substituted phenyl; wherein the substituted phenyl is substituted with 1-4 substituents selected from hydroxyl, $C_{1-6}$alkoxy, and $C_{1-6}$alkyl;
$R^9$ is hydrogen or $C_{1-6}$ alkyl;
x is a number from zero to six; and
y is zero;
or a pharmaceutically acceptable salt thereof;
formula (I-2) is represented by:

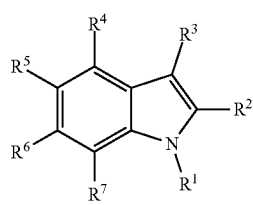

(I-2)

wherein
$R^1$ is hydrogen or $C_{1-6}$ alkyl;
$R^2$ and $R^3$ are independently hydrogen or $C_{1-6}$ alkyl;
$R^4$, $R^5$, $R^6$, and $R^7$ are independently selected from hydrogen, $C_{1-6}$alkyl, $C_{1-6}$alkoxy, —$OCH_2C_6H_5$, halogen, —CHO, and —$(CH_2)_x$—COOH; and
x is a number from zero to six;
or a pharmaceutically acceptable salt thereof;
provided that at least one of $R^4$, $R^5$, $R^6$, and $R^7$ is —CHO or —$(CH_2)_x$—COOH; and
formula (I-3) is represented by:

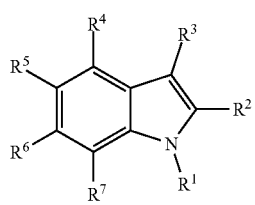

(I-3)

wherein
$R^1$ is hydrogen or $C_{1-6}$ alkyl;
$R^2$ is hydrogen or $C_{1-6}$ alkyl;
$R^3$ is —$(CH_2)_x$—COOH;
$R^4$, $R^5$, $R^6$, and $R^7$ are independently selected from hydrogen, $C_{1-6}$alkyl, $C_{1-6}$alkoxy, halogen, —$(CH_2)_x$—OH, and —$OCH_2C_6H_5$; and
x is a number from zero to six;
or a pharmaceutically acceptable salt thereof.

3. A method selected from:
(i) a method for treating an adipose tissue disorder or an adipose tissue tumor in a subject comprising locally administering to the subject a compound of Formula (I-1), Formula (I-2), or Formula (I-3), wherein Formula (I-1) is represented by:

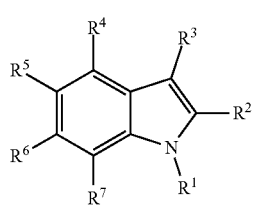

(I-1)

wherein
$R^1$ is hydrogen or $C_{1-6}$ alkyl;
$R^4$, $R^5$, $R^6$, and $R^7$ are independently selected from hydrogen, $C_{1-6}$alkyl, $C_{1-6}$alkoxy, halogen, and —$OCH_2C_6H_5$;
$R^2$ and $R^3$, together with the atoms they attach to, form

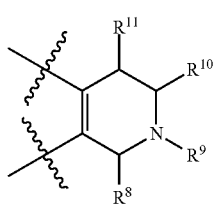

wherein $R^8$, $R^{10}$, and $R^{11}$ are independently selected from hydrogen, halogen, —$(CH_2)_x$—C(O)—$OC_{1-6}$ alkyl, —$(CH_2)_x$—OH, —$(CH_2)_x$—CN, —$OCH_2C_6H_5$, —$OCOCH_3$, —$(CH_2)_x$—$CONH_2$, —CHO, —$(CH_2)_x$—

COOH, —(CH$_2$)$_y$—CO—COOH, —(CH$_2$)$_y$—C(H)(OH)—COOH, phenyl, and substituted phenyl; wherein the substituted phenyl is substituted with 1-4 substituents selected from hydroxyl, C$_{1-6}$alkoxy, and C$_{1-6}$alkyl;

R$^9$ is hydrogen or C$_{1-6}$ alkyl;

x is a number from zero to six; and y is zero;

or a pharmaceutically acceptable salt thereof;

Formula (I-2) is represented by:

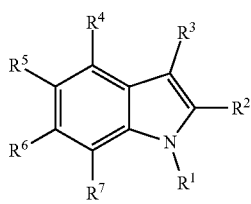

(I-2)

wherein

R$^1$ is hydrogen or C$_{1-6}$ alkyl;

R$^2$ and R$^3$ are independently hydrogen or C$_{1-6}$ alkyl;

R$^4$, R$^5$, R$^6$, and R$^7$ are independently selected from hydrogen, C$_{1-6}$alkyl, C$_{1-6}$alkoxy, —OCH$_2$C$_6$H$_5$, halogen, —CHO, and —(CH$_2$)$_x$—COOH; and x is a number from zero to six;

or a pharmaceutically acceptable salt thereof;

provided that at least one of R$^4$, R$^5$, R$^6$, and R$^7$ is —CHO or —(CH$_2$)$_x$—COOH; and Formula (I-3) is represented by:

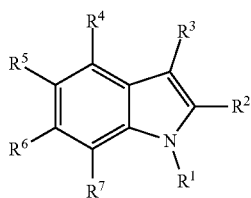

(I-3)

wherein

R$^1$ is hydrogen or C$_{1-6}$ alkyl;

R$^2$ is hydrogen or C$_{1-6}$ alkyl;

R$^3$ is —(CH$_2$)$_x$—COOH;

R$^4$, R$^5$, R$^6$, and R$^7$ are independently selected from hydrogen, C$_{1-6}$alkyl, C$_{1-6}$alkoxy, halogen, —(CH$_2$)$_x$—OH, and —OCH$_2$C$_6$H$_5$; and x is a number from zero to six;

or a pharmaceutically acceptable salt thereof; and (ii) a method for decreasing a submental fat deposit under a skin area in a subject comprising administering to a target site in the fat deposit a compound of Formula (I-1), Formula (I-2), or Formula (I-3), wherein Formula (I-1) is represented by:

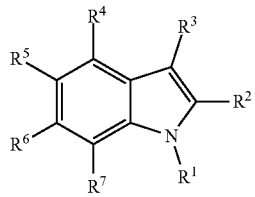

(I-1)

wherein

R$^1$ is hydrogen or C$_{1-6}$ alkyl;

R$^4$, R$^5$, R$^6$, and R$^7$ are independently selected from hydrogen, C$_{1-6}$alkyl, C$_{1-6}$alkoxy, halogen, and —OCH$_2$C$_6$H$_5$;

R$^2$ and R$^3$, together with the atoms they attach to, form

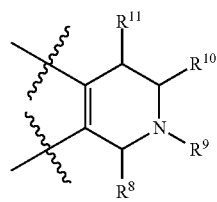

wherein R$^8$, R$^{10}$, and R$^{11}$ are independently selected from hydrogen, halogen, —(CH$_2$)$_x$—C(O)—OC$_{1-6}$ alkyl, —(CH$_2$)$_x$—OH, —(CH$_2$)$_x$—CN, —OCH$_2$C$_6$H$_5$, —OCOCH$_3$, —(CH$_2$)$_x$—CONH$_2$, —CHO, —(CH$_2$)$_x$—COOH, —(CH$_2$)$_y$—CO—COOH, —(CH$_2$)$_y$—C(H)(OH)—COOH, phenyl, and substituted phenyl; wherein the substituted phenyl is substituted with 1-4 substituents selected from hydroxyl, C$_{1-6}$alkoxy, and C$_{1-6}$alkyl;

R$^9$ is hydrogen or C$_{1-6}$ alkyl;

x is a number from zero to six; and y is zero;

or a pharmaceutically acceptable salt thereof;

Formula (I-2) is represented by:

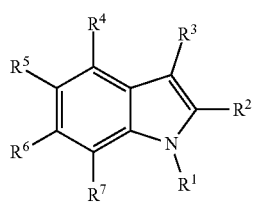

(I-2)

wherein

R$^1$ is hydrogen or C$_{1-6}$ alkyl;

R$^2$ and R$^3$ are independently hydrogen or C$_{1-6}$ alkyl;

R$^4$, R$^5$, R$^6$, and R$^7$ are independently selected from hydrogen, C$_{1-6}$alkyl, C$_{1-6}$alkoxy, —OCH$_2$C$_6$H$_5$, halogen, —CHO, and —(CH$_2$)$_x$—COOH; and x is a number from zero to six;

or a pharmaceutically acceptable salt thereof;

provided that at least one of R$^4$, R$^5$, R$^6$, and R$^7$ is —CHO or —(CH$_2$)$_x$—COOH; and Formula (I-3) is represented by:

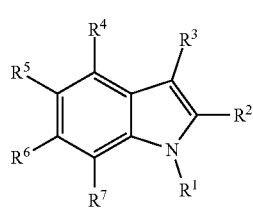

(I-3)

wherein
$R^1$ is hydrogen or $C_{1-6}$ alkyl;
$R^2$ is hydrogen or $C_{1-6}$ alkyl;
$R^3$ is —$(CH_2)_x$—COOH;
$R^4$, $R^5$, $R^6$, and $R^7$ are independently selected from hydrogen, $C_{1-6}$alkyl, $C_{1-6}$alkoxy, halogen, —$(CH_2)_x$—OH, and —$OCH_2C_6H_5$; and
x is a number from zero to six;
or a pharmaceutically acceptable salt thereof.

4. The method of claim 3, wherein the method is for decreasing a submental fat deposit under a skin area in a subject comprising administering to a target site in the fat deposit a compound of Formula (I-1), Formula (I-2), or Formula (I-3), wherein Formula (I-1) is represented by:

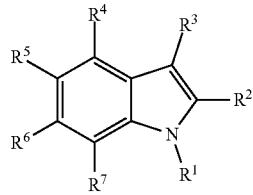

(I-1)

wherein
$R^1$ is hydrogen or $C_{1-6}$ alkyl;
$R^4$, $R^5$, $R^6$, and $R^7$ are independently selected from hydrogen, $C_{1-6}$alkyl, $C_{1-6}$alkoxy, halogen, and —$OCH_2C_6H_5$;
$R^2$ and $R^3$, together with the atoms they attach to, form

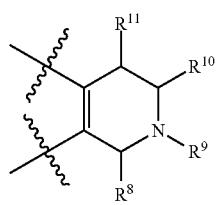

wherein $R^8$, $R^{10}$, and $R^{11}$ are independently selected from hydrogen, halogen, —$(CH_2)_x$—C(O)—$OC_{1-6}$ alkyl, —$(CH_2)_x$—OH, —$(CH_2)_x$—CN, —$OCH_2C_6H_5$, —$OCOCH_3$, —$(CH_2)_x$—$CONH_2$, —CHO, —$(CH_2)_x$—COOH, —$(CH_2)_y$—CO—COOH, —$(CH_2)_y$—C(H)(OH)—COOH, phenyl, and substituted phenyl; wherein the substituted phenyl is substituted with 1-4 substituents selected from hydroxyl, $C_{1-6}$alkoxy, and $C_{1-6}$alkyl;
$R^9$ is hydrogen or $C_{1-6}$ alkyl;
x is a number from zero to six; and
y is zero;
or a pharmaceutically acceptable salt thereof;

Formula (I-2) is represented by:

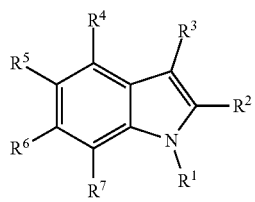

(I-2)

wherein
$R^1$ is hydrogen or $C_{1-6}$ alkyl;
$R^2$ and $R^3$ are independently hydrogen or $C_{1-6}$ alkyl;
$R^4$, $R^5$, $R^6$, and $R^7$ are independently selected from hydrogen, $C_{1-6}$alkyl, $C_{1-6}$alkoxy, —$OCH_2C_6H_5$, halogen, —CHO, and —$(CH_2)_x$—COOH; and
x is a number from zero to six;
or a pharmaceutically acceptable salt thereof;
provided that at least one of $R^4$, $R^5$, $R^6$, and $R^7$ is —CHO or —$(CH_2)_x$—COOH; and Formula (I-3) is represented by:

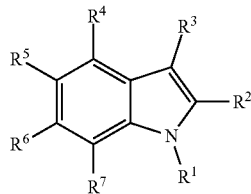

(I-3)

wherein
$R^1$ is hydrogen or $C_{1-6}$ alkyl;
$R^2$ is hydrogen or $C_{1-6}$ alkyl;
$R^3$ is —$(CH_2)_x$—COOH;
$R^4$, $R^5$, $R^6$, and $R^7$ are independently selected from hydrogen, $C_{1-6}$alkyl, $C_{1-6}$alkoxy, halogen, —$(CH_2)_x$—OH, and —$OCH_2C_6H_5$; and
x is a number from zero to six;
or a pharmaceutically acceptable salt thereof.

5. The method of claim 1, wherein the compound is of Formula (II):

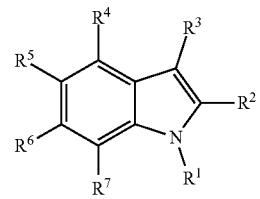

(II)

wherein
$R^1$ is hydrogen or $C_{1-6}$ alkyl;
$R^2$ and $R^3$ are independently hydrogen or $C_{1-6}$ alkyl;
$R^4$ is —CHO or —$(CH_2)_x$—COOH;
$R^5$, $R^6$, and $R^7$ are independently selected from hydrogen, $C_{1-6}$alkyl, $C_{1-6}$alkoxy, halogen, and —$OCH_2C_6H_5$; and
x is a number from zero to six;
or a pharmaceutically acceptable salt thereof.

6. The method of claim 1, wherein the compound is of Formula (IV):

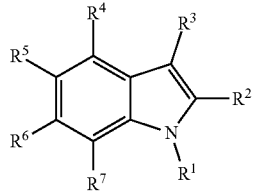

wherein
R$^1$ is hydrogen or C$_{1-6}$ alkyl;
R$^2$ and R$^3$ are independently hydrogen or C$_{1-6}$ alkyl;
R$^4$, R$^6$, and R$^7$ are independently selected from hydrogen, C$_{1-6}$alkyl, C$_{1-6}$alkoxy, halogen, and —OCH$_2$C$_6$H$_5$,
R$^5$ is —CHO or —(CH$_2$)$_x$—COOH; and
x is a number from zero to six;
or a pharmaceutically acceptable salt thereof.

7. The method of claim 1, wherein the compound is of Formula (V):

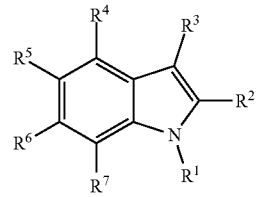

wherein
R$^1$ is hydrogen or C$_{1-6}$ alkyl;
R$^2$ is hydrogen or C$_{1-6}$ alkyl;
R$^3$ is —(CH$_2$)$_x$—COOH;
R$^4$, R$^5$, R$^6$, and R$^7$ are independently selected from hydrogen, C$_{1-6}$alkyl, C$_{1-6}$alkoxy, —OCH$_2$C$_6$H$_5$, and halogen; and
x is a number from zero to six;
or a pharmaceutically acceptable salt thereof.

8. The method of claim 1, wherein the compound is of Formula (VI):

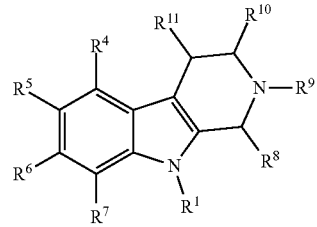

wherein
R$^1$ is hydrogen or C$_{1-6}$ alkyl;
R$^4$, R$^5$, R$^6$, and R$^7$ are independently selected from hydrogen, C$_{1-6}$alkyl, C$_{1-6}$alkoxy, halogen, and —OCH$_2$C$_6$H$_5$;
R$^8$, R$^{10}$, and R$^{11}$ are independently selected from hydrogen, halogen, —(CH$_2$)$_x$—C(O)—OC$_{1-6}$ alkyl, —OCH$_2$C$_6$H$_5$, —OCOCH$_3$, —(CH$_2$)$_x$—CONH$_2$, —CHO, —(CH$_2$)$_x$—COOH, phenyl, and substituted phenyl; wherein the substituted phenyl is substituted with 1-4 substituents selected from hydroxyl, C$_{1-6}$alkoxy, and C$_{1-6}$alkyl;
R$^9$ is hydrogen or C$_{1-6}$ alkyl; and
x is zero;
or a pharmaceutically acceptable salt thereof.

9. The method of claim 1, wherein the compound is a compound in Table 1A below, or a pharmaceutically acceptable salt thereof:

TABLE 1A

| Compound | Structure | Chemical Name |
|---|---|---|
| 10 | 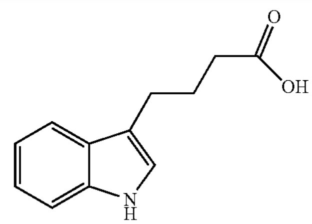 [SMILES: O=C(O)CCCc1c[nH]c2ccccc12] | 4-(1H-indol-3-yl)butanoic acid |
| 30 | 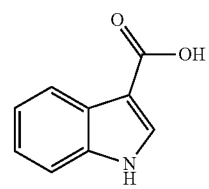 [SMILES: O=C(O)c1c[nH]c2ccccc12] | 1H-indole-2-carboxylic acid. |

10. The method of claim 1, wherein the compound is a compound in Table 1B below, or a pharmaceutically acceptable salt thereof:

TABLE 1B

| | | |
|---|---|---|
| 3 | | 1H-indole-5-carbaldehyde |
| 4 | | 1H-indole-7-carbaldehyde |
| 5 | | 1H-indole-4-carbaldehyde |
| 6 | | 1H-indole-6-carbaldehyde |

TABLE 1B-continued

| 27 | [1H-indole-4-carboxylic acid structure] | 1H-indole-4-carboxylic acid |
| 28 | [1H-indole-5-carboxylic acid structure] | 1H-indole-5-carboxylic acid. |

11. The method of claim 1, wherein the compound is a compound in Table 1C below, or a pharmaceutically acceptable salt thereof:

TABLE 1C

| 78 | [structure] | (1R,3R)-1-(2,4-dihydroxyphenyl)-2,3,4,9-tetrahydro-1H-pyrido[3,4-b]indole-3-carboxylic acid. |

12. The method of claim 1, wherein the administering step is by injection, transdermal pump, transdermal patch, or a subdermal depot.

13. The method of claim 1, wherein the administering step is by subcutaneous injection or intradermal injection.

14. The method of claim 1, wherein the subject is a mammal.

15. The method of claim 1, wherein the subject is a human.

16. The method of claim 1, further comprising administering to the subject a second therapeutic agent.

17. The method of claim 1, wherein the compound is of Formula (IV-1):

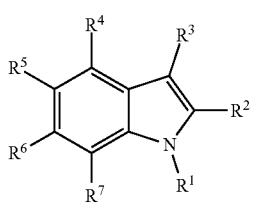

(IV-1)

wherein
R$^1$ is hydrogen or C$_{1-6}$ alkyl;
R$^2$ and R$^3$ are independently hydrogen or C$_{1-6}$ alkyl; and
R$^4$, R$^5$, R$^6$, and R$^7$ are independently selected from hydrogen, C$_{1-6}$alkyl, C$_{1-6}$alkoxy, halogen, —OCH$_2$C$_6$H$_5$, and —CHO;

or a pharmaceutically acceptable salt thereof;
provided that at least one of R$^4$, R$^5$, R$^6$, and R$^7$ is —CHO.

18. The method of claim 1, wherein the compound is of Formula (IV-2):

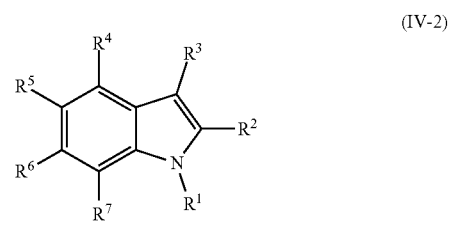

(IV-2)

wherein
R$^1$ is hydrogen or C$_{1-6}$ alkyl;
R$^2$ and R$^3$ are independently hydrogen or C$_{1-6}$ alkyl;
R$^4$, R$^5$, R$^6$, and R$^7$ are independently selected from hydrogen, C$_{1-6}$alkyl, C$_{1-6}$alkoxy, halogen, —OCH$_2$C$_6$H$_5$, and —(CH$_2$)$_x$—COOH; and
x is a number from zero to six;
or a pharmaceutically acceptable salt thereof;
provided that at least one of R$^4$, R$^5$, R$^6$, and R$^7$ is —(CH$_2$)$_x$—COOH.

19. The method of claim 1, wherein the compound is a compound in Table 1D below, or a pharmaceutically acceptable salt thereof:

TABLE 1D

| 3 | [structure] | 1H-indole-5-carbaldehyde |
| 4 | [structure] | 1H-indole-7-carbaldehyde |
| 5 | [structure] | 1H-indole-4-carbaldehyde |
| 6 | [structure] | 1H-indole-6-carbaldehyde. |

20. The method of claim 1, wherein the compound is a compound in Table 1E below, or a pharmaceutically acceptable salt thereof:

TABLE 1E
| | | | |
|---|---|---|---|
| 27 | 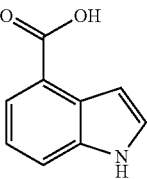 | 1H-indole-4-carboxylic acid | |
| 28 | 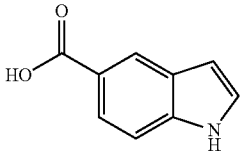 | 1H-indole-5-carboxylic acid. | |
* * * * *